(12) United States Patent
Kittleson et al.

(10) Patent No.: US 11,858,971 B2
(45) Date of Patent: *Jan. 2, 2024

(54) ELASTOMERIC PROTEINS

(71) Applicant: Bolt Threads, Inc., Emeryville, CA (US)

(72) Inventors: Joshua Kittleson, Berkeley, CA (US); Michael Lee, Berkeley, CA (US); David N. Breslauer, San Francisco, CA (US); Daniel M. Widmaier, San Francisco, CA (US)

(73) Assignee: BOLT THREADS, INC., Emeryville, CA (US)

( * ) Notice: Subject to any disclaimer, the term of this patent is extended or adjusted under 35 U.S.C. 154(b) by 156 days.

This patent is subject to a terminal disclaimer.

(21) Appl. No.: 17/219,277

(22) Filed: Mar. 31, 2021

(65) Prior Publication Data

US 2021/0340194 A1 Nov. 4, 2021

Related U.S. Application Data

(63) Continuation of application No. 16/477,133, filed as application No. PCT/US2018/013839 on Jan. 16, 2018, now Pat. No. 10,988,515.

(51) Int. Cl.
*C07K 14/435* (2006.01)
*C12P 21/02* (2006.01)

(52) U.S. Cl.
CPC .... *C07K 14/43563* (2013.01); *C07K 14/4359* (2013.01); *C07K 14/43577* (2013.01); *C07K 14/43581* (2013.01); *C12P 21/02* (2013.01)

(58) Field of Classification Search
None
See application file for complete search history.

(56) References Cited

U.S. PATENT DOCUMENTS

| | | | |
|---|---|---|---|
| 9,074,098 B2 | 7/2015 | Tew et al. | |
| 10,988,515 B2 * | 4/2021 | Kittleson | C07K 14/43577 |
| 2007/0275408 A1 | 11/2007 | Elvin | |
| 2008/0264867 A1 | 10/2008 | Mika et al. | |
| 2014/0206022 A1 | 7/2014 | Nuti et al. | |
| 2016/0114075 A1 | 4/2016 | Brownlee et al. | |
| 2016/0222174 A1 | 8/2016 | Widmaier et al. | |
| 2016/0252505 A1 | 9/2016 | Braun et al. | |

FOREIGN PATENT DOCUMENTS

| | | | |
|---|---|---|---|
| JP | S63-044899 A | 2/1988 | |
| JP | H05-076371 A | 3/1993 | |
| JP | 2013-509180 A | 3/2013 | |
| JP | 2020-503882 | 2/2020 | |
| WO | 2006/026325 A2 | 3/2006 | |
| WO | 2008/019183 A2 | 2/2008 | |
| WO | WO-2011/053541 A1 | 5/2011 | |
| WO | 2015/068160 A1 | 5/2015 | |
| WO | WO-2016/183163 A1 | 11/2016 | |
| WO | 2018/132821 A2 | 7/2018 | |

OTHER PUBLICATIONS

Secretion and Production of Proteins in Yeasts, Kagaku to Seibutsu (Chemistry and Biology), vol. 33, No. 7, pp. 427-436 (1995).
Secretion of Foreign Proteins in Yeast, Kagaku to Seibutsu (Chemistry and Biology), vol. 26, No. 9, pp. 568-576 (1988).
Azam, A., et al., "Type III Secretion as a Generalizable Strategy for the Production of Full-Lenth Biopolymer-Forming Proteins", Biotechnology and Bioenginering 113: 2313-2320 (Year: 2016).
Qin, G., et al., "Mechanism of resilin elasticity", Nature Commnications, published Aug. 14, 2012, 9 pages.
Elvin, C., et al., "Synthesis and properties of crosslinked recombinant pro-resilin", Nature, vol. 437, Oct. 13, 2015, 4 pages.
UniProtKB—Q9V7U0 (Resil_Drome): ORF Names: CG15920, 5 pages.
Kim, M., et al., "High yield expression of recombinant pro-resilin: Lactose-induced fermentation in E. coli and facile purification", Elsevier, 2006, 7 pages.
Charati, M., et al., "Hydophilic elastomeric biomaterials based on reilin-like polypeptides", Soft Matter. 2009; 5(18): 3412-3416.
International Search Report and The Written Opinion for PCT/US2018/013829, received Jul. 3, 2018, 24 pages.
Ghazinezhad, M., et al., "Preparation of Hydrogels Via Cross-Linking of Partially Hydrolyzed Polyacrylamides with Potassium Persulfate at Moderate Temperatures", Der Chemica Sinica. 2014, vol. 5, No. 5, pp. 19-26.
International Search Report and The Written Opinion for PCT/US19/42387, received Oct. 22, 2019, 30 pages.
Database UniProt [Online], Jun. 28, 2011, "SubName: Full=Pro-resilin {ECO:0000313 | EMBL: EGI57805.1};", XP55746686, retreived from EBI accession No. Uniprot: F4X6M3 Database accession No. F4X6M3.
Extended European Search Report for Application No. 18739425.9, received Dec. 11, 2020, 8 pages.

* cited by examiner

*Primary Examiner* — Anand U Desai
(74) *Attorney, Agent, or Firm* — MARSHALL, GERSTEIN & BORUN LLP

(57) ABSTRACT

This invention relates to elastomeric protein and elastomeric protein production. In particular, the invention is directed to elastomeric protein sequences, including methods and compositions for production of elastomeric protein sequences, such as expression constructs, and host cells, and including compositions generated from the elastomeric protein sequences.

21 Claims, 12 Drawing Sheets
Specification includes a Sequence Listing.

*MRFPSIFTAVLFAASSALAAPVNTTTEDETAQIPAEAVIGYSDLEGDFDVAVLPFSNSTNNGLLFIN TTIASIAAKEEGVSLEKR*EAEAgrpeppvnsylppsdsygapgqsgaggrpsdtygapgggnggrps dsygapggggggyggkpsdsygapggngnggrpsssygapggnggrpsdtygapgggng grpsdtygapgggnggrpsssygapgggnggrpsdtygapgggng grpsdtygapgggnggrpsssygapgggnggrpsdtygapgggnggrpsssygapaqggggf ggrpsdsygapgqnqkpsdsygapgsgngsagrpsssygapgsgpggrpsdsygppasgsgaggagg sgpggadydndepakyefnyqvedapsglsfghsemrdgfttgqynvllpdgrkqiveyeadqggy rpqiryegdandgsgpsgpsgpggpggqnlgadgyssgrpgngngngyssgrpgggdlgpsgys ggrpgggdlgaggysnvkpgggdlpggysgrpgggdlgrdgysgrpgggdlgagaysngrpggn gnggsdggrviiggrviiggqdgggdqgysgpgggrpgggqdlgrdgyssgrpggrpggngqdsqdggyssg rpgqggrngfgpggqngdndgsgyrySGDYKDDDDKDYKDDDDKDYKDDDDK (SEQ ID NO: 63)

FIGURE 10

ELASTOMERIC PROTEINS

CROSS REFERENCE TO RELATED APPLICATIONS

This application is a continuation of U.S. application Ser. No. 16/477,133, filed Jul. 10, 2019, which is a 371 national phase application of International Application No. PCT/US18/13839, filed Jan. 16, 2018, which claims the benefit of U.S. Provisional Application No. 62/446,230, filed Jan. 13, 2017, the entire disclosure of which is hereby incorporated by reference, in its entirety, for all purposes.

SEQUENCE LISTING

The instant application contains a Sequence Listing which has been submitted electronically in ASCII format and is hereby incorporated by reference in its entirety. Said ASCII copy, created on Mar. 31, 2021, is named BTT-007C1_CRF_sequencelisting.txt and is 167,578 bytes in size.

TECHNICAL FIELD

The present disclosure relates generally to elastomeric protein and elastomeric protein production. Specifically, the present disclosure relates to elastomeric protein sequences, expression constructs, host cells, and solids.

BACKGROUND

Elastomeric proteins are polypeptides that exhibit viscoelastic mechanical properties, and include elastin, resilin, abductin, and octopus arterial elastomers. Resilin is a particularly interesting elastomeric protein because it dissipates very little energy during loading and unloading. Resilin is found in many insects, and the low energy dissipation enables the extraordinary ability of many insect species to jump or pivot their wings very efficiently. The unique properties of resilin make it an interesting elastomeric material that could have many industrial applications. However, resilin exists in only very small quantities in nature, and therefore cannot be cost-effectively farmed by raising insects.

Variations of natural resilins and resilin-like proteins (based on resilin sequences) have been recombinantly produced by a number of groups in *E. coli* cultures, and have been isolated by lysing the cells to extract recombinantly expressed proteins, and using affinity chromatography techniques to purify (Elvin et al., 2005; Charati et al.; 2009, McGann et al., 2013). The recombinantly produced resilin and resilin-like proteins have been cross-linked targeting the tyrosine residues that also form the cross-links in natural resilin (see, for example, Elvin et al., 2005; Qin et al., 2011). Recombinantly produced resilin has also been cross-linked targeting lysine residues (Li et al., 2011) or cysteine residues (McGann et al., 2013). Cross-linked recombinantly produced resilin and resilin-like proteins have shown mechanical properties similar to those of natural resilin, with resilience values in excess of 90% (Elvin et al., 2005, Qin et al., 2011, Li et al., 2011).

In one study, 70-80 mg of recombinant resilin-like protein were produced per liter of *E. coli* culture, and the resilin-like protein was purified by Ni-NTA affinity chromatography (Charati et al., 2009). More efficient expression systems have been developed, which have produced 300-450 mg/L of recombinant resilin-like proteins from *E. coli* host cells (Lyons, et al., 2009). More efficient methods have also been developed for purifying the resilin-like proteins from lysed *E. coli* host cells, based on salt precipitation followed by heating (Qin et al., 2011; Lyons et al., 2009). However, improved systems for expressing and purifying elastomeric proteins (e.g., resilin and resilin-like proteins) with greater productivity are desired to provide more efficient protein production at larger scales.

At least one drawback of recovering expressed proteins by lysing cells followed by simple precipitation-based purification techniques is that the resulting proteins tend to have low purity due to cellular proteins from the lysed cells contaminating the target protein. Low purity can result in a variety of product defects, including low resilience. Furthermore, intracellular accumulation of protein can lead to toxicity and therefore decreased efficiency of production of recombinant elastomeric proteins. What is needed, therefore, are improved methods for expression and purification of recombinant elastomeric proteins that include methods to recover elastomeric proteins from extracellular portions. What is also needed are improved methods for expression and purification of recombinant elastomeric proteins (e.g., resilin and resilin-like proteins) that have a greater production efficiency.

SUMMARY OF THE INVENTION

According to some embodiments, provided herein is a method for producing a composition comprising a recombinant resilin protein, the method comprising: culturing a population of recombinant host cells in a fermentation, wherein said recombinant host cells comprise a vector comprising a secreted resilin coding sequence, and wherein said recombinant host cells secrete a recombinant resilin protein encoded by said secreted resilin coding sequence; and purifying said recombinant resilin protein from said fermentation.

In some embodiments, the recombinant resilin protein is a full-length or truncated native resilin. In some embodiments, the native resilin is from an organism selected from the group consisting of: *Drosophila sechellia, Acromyrmex echinatior, Aeshna, Haematobia irritans, Ctenocephalides felis, Bombus terrestris, Tribolium castaneum, Apis mellifera, Nasonia vitripennis, Pediculus humanus corporis, Anopheles gambiae, Glossina morsitans, Atta cephalotes, Anopheles darlingi, Acyrthosiphon pisum, Drosophila virilis, Drosophila erecta, Lutzomyia longipalpis, Rhodnius prolixus, Solenopsis invicta, Culex quinquefasciatus, Bactrocera cucurbitae,* and *Trichogramma pretiosum*. In some embodiments, the recombinant resilin protein comprises SEQ ID NO: 1. In some embodiments, the recombinant resilin protein comprises SEQ ID NO: 4.

In some embodiments, the recombinant resilin protein comprises an alpha mating factor secretion signal. In some embodiments, the recombinant resilin protein comprises a FLAG-tag. In some embodiments, the vector comprises more than one secreted resilin coding sequence.

In some embodiments, the recombinant host cells are yeast cells. In some embodiments, the yeast cells are methylotrophic yeast cells. In some embodiments, the recombinant host cells are a species selected from the group consisting of: *Pichia (Komagataella) pastoris, Hansenula polymorpha, Arxula adeninivorans, Yarrowia lipolytica, Pichia (Scheffersomyces) stipitis, Pichia methanolica, Saccharomyces cerevisiae,* and *Kluyveromyces lactis*.

In some embodiments, the recombinant host cells produce the recombinant resilin at a rate of greater than 2 mg resilin/g dry cell weight/hour. In some embodiments, the recombinant host cells produce a secreted fraction of the recombinant resilin that is greater than 50% as compared to the total recombinant resilin protein expressed by the recombinant host cells. In some embodiments, the recombinant host cells secrete the recombinant resilin at a rate of greater than 2 mg resilin/g dry cell weight/hour. In some embodiments, greater than 80% of the recombinant resilin is outside of the recombinant host cells in said fermentation. In some embodiments, the fermentation comprises at least 2 g recombinant resilin/L.

In some embodiments, purifying said recombinant resilin protein comprises: generating a first pellet fraction and a first supernatant fraction by centrifuging the fermentation; and isolating the recombinant resilin protein from the first pellet fraction. In some embodiments, purifying said recombinant resilin protein further comprises: adding a chaotrope to the first pellet fraction to generate a solution in which the recombinant resilin protein is soluble; generating a second supernatant fraction and a second pellet fraction by centrifuging the first pellet fraction comprising said chaotrope; and isolating the soluble full-length resilin from the second supernatant fraction.

In some embodiments, provided herein is a vector comprising a secreted resilin coding sequence. In some embodiments, the secreted resilin coding sequence encodes a full-length or truncated native resilin. In some embodiments, the secreted resilin coding sequence encodes a modified full-length or truncated native resilin. In some embodiments, the modified resilin comprises an addition, subtraction, replacement, or change in position of an amino acid residue capable of cross-linking to another resilin.

In some embodiments, the full-length or truncated native resilin is from an organism selected from the group consisting of: *Drosophila sechellia, Acromyrmex echinatior, Aeshna, Haematobia irritans, Ctenocephalides felis, Bombus terrestris, Tribolium castaneum, Apis mellifera, Nasonia vitripennis, Pediculus humanus corporis, Anopheles gambiae, Glossina morsitans, Atta cephalotes, Anopheles darlingi, Acyrthosiphon pisum, Drosophila virilis, Drosophila erecta, Lutzomyia longipalpis, Rhodnius prolixus, Solenopsis invicta, Culex quinquefasciatus, Bactrocera cucurbitae,* and *Trichogramma pretiosum.*

In some embodiments, the secreted resilin coding sequences encodes a polypeptide comprising SEQ ID NO: 1. In some embodiments, the secreted resilin coding sequence encodes a polypeptide comprising SEQ ID NO: 4. In some embodiments, the secreted resilin coding sequence encodes a recombinant resilin comprising one or more A-repeats or quasi-A-repeats. In some embodiments, the secreted resilin coding sequence encodes a recombinant resilin comprising one or more B-repeats or quasi-B-repeats. In some embodiments, the secreted resilin coding sequence encodes a recombinant resilin comprising either one or more A-repeats or quasi-A-repeats or one or more B-repeats or quasi-B repeats but not both. In some embodiments, the secreted resilin coding sequence encodes a recombinant resilin comprising one or more A-repeats or quasi-A-repeats and one or more B-repeats or quasi-B-repeats.

In some embodiments, the recombinant resilin further comprises a chitin binding domain. In some embodiments, the secreted resilin coding sequence encodes a polypeptide comprising an alpha mating factor secretion signal. In some embodiments, the secreted resilin coding sequence comprises a FLAG-tag.

In some embodiments, the vector comprises more than one secreted resilin coding sequence. In some embodiments, the vector comprises 3 secreted resilin coding sequences. In some embodiments, the secreted resilin coding sequence is operatively linked to a constitutive or inducible promoter.

Also provided herein, according to some embodiments, is a recombinant host cell comprising one or more vectors comprising a secreted resilin coding sequence. In some embodiments, the recombinant host cell is a yeast cell. In some embodiments, the yeast cell is a methylotrophic yeast cell. In some embodiments, the recombinant host cell is a species selected from the group consisting of: *Pichia (Komagataella) pastoris, Hansenula polymorpha, Arxula adeninivorans, Yarrowia lipolytica, Pichia (Scheffersomyces) stipitis, Pichia methanolica, Saccharomyces cerevisiae,* and *Kluyveromyces lactis.*

In some embodiments, the recombinant host cell comprises 3 vectors comprising a secreted resilin coding sequence.

In some embodiments, the recombinant host cell produces recombinant resilin at a rate of greater than 2 mg resilin/g dry cell weight/hour. In some embodiments, the recombinant host cell has a secreted fraction of recombinant resilin that is greater than 50%. In some embodiments, the recombinant host cell secretes resilin at a rate of greater than 2 mg resilin/g dry cell weight/hour.

Also provided herein, according to some embodiments, is a fermentation comprising a recombinant host cell comprising one or more vectors comprising a secreted resilin coding sequence and a culture medium suitable for growing the recombinant host cell.

In some embodiments, the fermentation comprises at least 2 g recombinant resilin/L.

In some embodiments of the fermentation, greater than 80% of recombinant resilin is outside of the recombinant host cells.

In some embodiments of the fermentation, the recombinant resilin is full-length recombinant resilin.

Also provided herein, according to some embodiments, is a composition comprising recombinant resilin derived from a fermentation comprising a recombinant host cell comprising one or more vectors comprising a secreted resilin coding sequence and a culture medium suitable for growing the recombinant host cell. In some embodiments, the composition comprises at least 60% by weight of recombinant resilin.

In some embodiments, the composition has similar properties compared to compositions comprising similar amounts of native resilins. In some embodiments, the composition has different properties compared to compositions comprising similar amounts of native resilins.

In some embodiments, the composition comprises a resilience of greater than 50%. In some embodiments, the composition comprises has a compressive elastic modulus of less than 10 MPa. In some embodiments, the composition has a tensile elastic modulus of less than 10 MPa. In some embodiments, the composition has a shear modulus of less than 1 MPa. In some embodiments, the composition has an extension to break of greater than 1%. In some embodiments, the composition has a maximum tensile strength of greater than 0.1 kPa. In some embodiments, the composition has a Shore 00 Hardness of less than 90. In some embodiments, the composition comprises full-length resilin.

Also provided herein, according to some embodiments, is a method for producing a composition comprising recombinant resilin, the method comprising the step of culturing a recombinant host cell comprising one or more vectors comprising a secreted resilin coding sequence to produce a fermentation under conditions that promote secretion of recombinant resilin from the recombinant host cell.

In some embodiments, the method for producing a composition comprising recombinant resilin further comprises the step of purifying said recombinant resilin to produce full-length native resilin. In some embodiments, purifying said recombinant resilin to produce full-length native resilin comprises: generating a first pellet fraction and a first supernatant fraction by centrifuging the fermentation; and isolating the recombinant resilin protein from the first pellet fraction. In some embodiments, isolating the recombinant resilin protein from the first pellet fraction comprises: adding a chaotrope to the first pellet fraction to generate a solution in which the recombinant resilin protein is soluble; generating a second supernatant fraction and a second pellet fraction by centrifuging the first pellet fraction comprising said chaotrope; and isolating the recombinant resilin protein from the second supernatant fraction.

In some embodiments, the method for producing a composition comprising recombinant resilin further comprises the step of cross-linking a plurality of said recombinant resilins. In some embodiments, said cross-linking is enzymatic cross-linking. In some embodiments, said cross-linking is photochemical cross-linking. In some embodiments, the recombinant resilin protein comprises a full-length resilin protein.

Also provided herein, according to some embodiments, is a fermentation comprising a culture medium and a recombinant host cell, wherein the recombinant host cell comprises a vector, wherein the vector comprises a secreted resilin coding sequence, and wherein the recombinant host cell secretes recombinant resilin at a rate of at least 2 mg/g dry cell weight/hour.

BRIEF DESCRIPTION OF THE DRAWINGS

FIG. 10 is the full-length *Drosophila sechellia* resilin sequence (Ds_ACB) (SEQ ID NO: 1, corresponding to the lower case letters) that is expressed along with signal sequences that are later cleaved, according to some embodiments of the invention.

Figure 1:
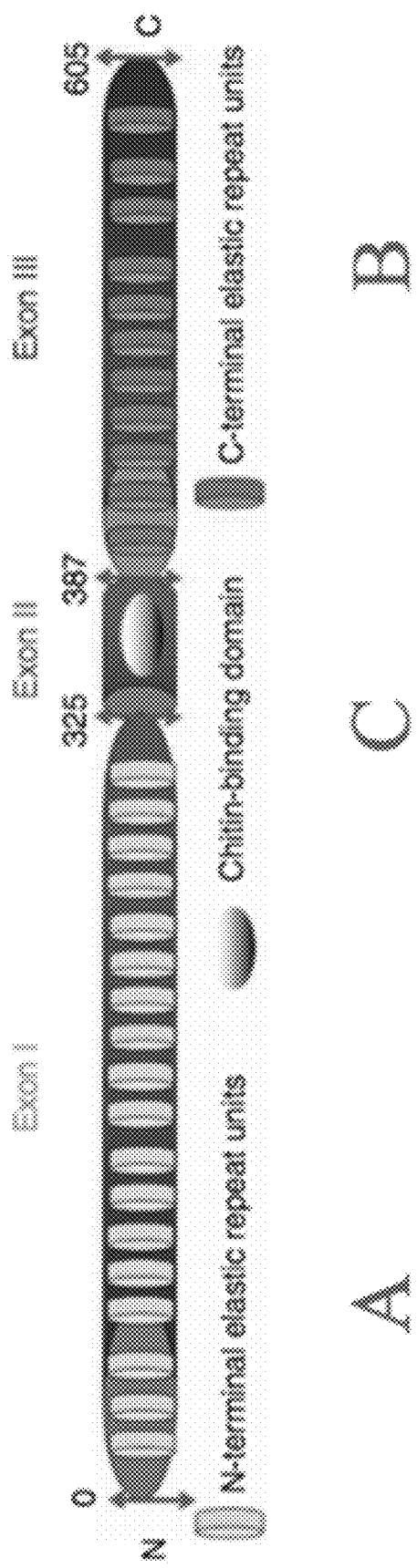
FIG. 1 schematically illustrates the structure of an exemplary resilin.

The figures depict various embodiments of the present disclosure for purposes of illustration only. One skilled in the art will readily recognize from the following discussion that alternative embodiments of the structures and methods illustrated herein may be employed without departing from the principles described herein.

Definitions

Unless defined otherwise, all technical and scientific terms used herein have the same meaning as is commonly understood by one of ordinary skill in the art to which this disclosure pertains.

The terms "a" and "an" and "the" and similar referents as used herein refer to both the singular and the plural, unless otherwise indicated herein or clearly contradicted by context.

The term "about," "approximately," or "similar to" means within an acceptable error range for the particular value as determined by one of ordinary skill in the art, which can depend in part on how the value is measured or determined, or on the limitations of the measurement system. It should be understood that all ranges and quantities described below are approximations and are not intended to limit the invention. Where ranges and numbers are used these can be approximate to include statistical ranges or measurement errors or variation. In some embodiments, for instance, measurements could be plus or minus 10%.

Amino acids can be referred to by their single-letter codes or by their three-letter codes. The single-letter codes, amino acid names, and three-letter codes are as follows: G—Glycine (Gly), P—Proline (Pro), A—Alanine (Ala), V—Valine (Val), L—Leucine (Leu), I—Isoleucine (Ile), M—Methionine (Met), C—Cysteine (Cys), F—Phenylalanine (Phe), Y—Tyrosine (Tyr), W—Tryptophan (Trp), H—Histidine (His), K—Lysine (Lys), R—Arginine (Arg), Q—Glutamine (Gln), N—Asparagine (Asn), E—Glutamic Acid (Glu), D—Aspartic Acid (Asp), S—Serine (Ser), T—Threonine (Thr).

The terms "including," "includes," "having," "has," "with," or variants thereof are intended to be inclusive in a manner similar to the term "comprising".

The term "microbe" as used herein refers to a microorganism, and refers to a unicellular organism. As used herein, the term includes all bacteria, all archaea, unicellular protista, unicellular animals, unicellular plants, unicellular fungi, unicellular algae, all protozoa, and all chromista.

The term "native" as used herein refers to compositions found in nature in their natural, unmodified state.

The terms "optional" or "optionally" mean that the feature or structure may or may not be present, or that an event or circumstance may or may not occur, and that the description includes instances where a particular feature or structure is present and instances where the feature or structure is absent, or instances where the event or circumstance occurs and instances where the event or circumstance does not occur.

The term "secreted fraction" as used herein refers to the fraction of recombinant resilins that are secreted from cells compared to the total resilins produced by the cells.

The term "secretion signal" as used herein refers to a short peptide that when fused to a polypeptide mediates the secretion of that polypeptide from a cell.

The term "secreted resilin coding sequence" as used herein refers to a nucleotide sequence that encodes a resilin as provided herein fused at its N-terminus to a secretion signal and optionally at its C-terminus to a tag peptide or polypeptide.

The term "recombinant" as used herein in reference to a polypeptide (e.g., resilin) refers to a polypeptide that is produced in a recombinant host cell, or to a polypeptide that is synthesized from a recombinant nucleic acid.

The term "recombinant host cell" as used herein refers to a host cell that comprises a recombinant nucleic acid.

The term "recombinant nucleic acid" as used herein refers to a nucleic acid that is removed from its naturally occurring environment, or a nucleic acid that is not associated with all or a portion of a nucleic acid abutting or proximal to the nucleic acid when it is found in nature, or a nucleic acid that is operatively linked to a nucleic acid that it is not linked to in nature, or a nucleic acid that does not occur in nature, or a nucleic acid that contains a modification that is not found in that nucleic acid in nature (e.g., insertion, deletion, or point mutation introduced artificially, e.g., by human intervention), or a nucleic acid that is integrated into a chromosome at a heterologous site. The term includes cloned DNA isolates and nucleic acids that comprise chemically-synthesized nucleotide analog.

The term "vector" as used herein refers to a nucleic acid molecule capable of transporting another nucleic acid to which it has been linked. One type of vector is a "plasmid," which generally refers to a circular double stranded DNA loop into which additional DNA segments can be ligated, but also includes linear double-stranded molecules such as those resulting from amplification by the polymerase chain reaction (PCR) or from treatment of a circular plasmid with a restriction enzyme. Other vectors include bacteriophages, cosmids, bacterial artificial chromosomes (BAC), and yeast artificial chromosomes (YAC). Another type of vector is a viral vector, wherein additional DNA segments can be ligated into the viral genome. Certain vectors are capable of autonomous replication in a cell into which they are introduced (e.g., vectors having an origin of replication that functions in the cell). Other vectors can be integrated into the genome of a cell upon introduction into the cell, and are thereby replicated along with the cell genome.

The term "repeat" as used herein, in reference to an amino acid or nucleic acid sequence, refers to a sub-sequence that is present more than once in a polynucleotide or polypeptide (e.g., a concatenated sequence). A polynucleotide or polypeptide can have a direct repetition of the repeat sequence without any intervening sequence, or can have non-consecutive repetition of the repeat sequence with intervening sequences. The term "quasi-repeat" as used herein, in reference to amino acid or nucleic acid sequences, is a sub-sequence that is inexactly repeated (i.e., wherein some portion of the quasi-repeat subsequence is variable between quasi-repeats) across a polynucleotide or polypeptide. Repeating polypeptides and DNA molecules (or portions of polypeptides or DNA molecules) can be made up of either repeat sub-sequences (i.e., exact repeats) or quasi-repeat sub-sequences (i.e., inexact repeats).

The term "native resilin" as used herein refers to an elastomeric polypeptide or protein produced by insects. GenBank Accession Nos. of non-limiting examples of native resilin includes the following NCBI sequence numbers: NP 995860 (*Drosophila melanogaster*), NP 611157 (*Drosophila melanogaster*), Q9V7U0 (*Drosophila melanogaster*), AAS64829, AAF57953 (*Drosophila melanogaster*), XP 001817028 (*Tribolium castaneum*) and XP001947408 (*Acyrthosiphon pisum*).

The term "modified" as used herein refers to a protein or polypeptide sequence that differs in composition from a native protein or polypeptide sequence, where the functional properties are preserved to within 10% of the native protein or polypeptide properties. In some embodiments, the difference between the modified protein or polypeptide and the native protein or polypeptide can be in primary sequence (e.g., one or more amino acids are removed, inserted or substituted) or post-translation modifications (e.g., glycosylation, phosphorylation). Amino acid deletion refers to removal of one or more amino acids from a protein. Amino acid insertion refers to one or more amino acid residues being introduced in a protein or polypeptide. Amino acid insertions may comprise N-terminal and/or C-terminal fusions as well as intra-sequence insertions of single or multiple amino acids. Amino acid substitution includes non-conservative or conservative substitution, where conservative amino acid substitution tables are well known in the art (see for example Creighton (1984) Proteins. W. H. Freeman and Company (Eds)). In some embodiments, the modified protein or polypeptide and the native protein or polypeptide amino acid or nucleotide sequence identity is at least 60%, at least 65%, at least 70%, at least 75%, at least 80%, at least 85%, at least 90%, at least 95%, or at least 98% of the amino acids or nucleotide bases.

The term "truncated" as used herein refers to a protein or polypeptide sequence that is shorter in length than a native protein or polypeptide. In some embodiments, the truncated protein or polypeptide can be greater than 10%, or greater than 20%, or greater than 30%, or greater than 40%, or greater than 50%, or greater than 60%, or greater than 70%, or greater than 80%, or greater than 90% of the length of the native protein or polypeptide.

The term "homolog" or "substantial similarity," as used herein, when referring to a polypeptide, nucleic acid or fragment thereof, indicates that, when optimally aligned with appropriate amino acid or nucleotide insertions or deletions with another amino acid or nucleic acid (or its complementary strand), there is amino acid or nucleotide sequence identity in at least 60%, at least 65%, at least 70%, at least 75%, at least 80%, at least 85%, at least 90%, at least 95%, or at least 98% of the amino acids or nucleotide bases, as measured by any well-known algorithm of sequence identity, such as FASTA, BLAST or Gap, as discussed above.

The term "resilin" as used herein refers to a protein or a polypeptide, capable of cross-linking to form an elastomer, where the protein or polypeptide is a native resilin, or a native resilin that is modified, or a native resilin that is truncated. Resilins of the present invention are preferably recombinant resilins. In some embodiments, recombinant resilins comprise a natural or modified (e.g., truncated or concatenated) nucleotide sequence coding for resilin or resilin fragments (e.g., isolated from insects), heterologously expressed and secreted from a host cell. In preferred embodiments, the secreted recombinant resilin protein is collected from a solution extracellular to the host cell.

As used herein, the term "elastomer" refers to a polymer with viscoelasticity and typically weak inter-molecular forces (except for covalent cross-links between molecules, if they are present). Viscoelasticity is a property of materials that exhibit both viscous and elastic characteristics when undergoing deformation, and therefore exhibit time-dependent strain. Elasticity is associated with bond stretching along crystallographic planes in an ordered solid, and viscosity is the result of the diffusion of atoms or molecules inside an amorphous material. Elastomers that are viscoelastic, therefore, generally have low Young's modulus and high failure strain compared with other materials. Due to the viscous component of the material, viscoelastic materials dissipate energy when a load is applied and then removed. This phenomenon is observed as hysteresis in the stress-strain curve of viscoelastic materials. As a load is applied there is a particular stress-strain curve, and as the load is removed the stress-strain curve upon unloading is different than that of the curve during loading. The energy dissipated is the area between the loading and unloading curves.

Recitation of ranges of values herein are merely intended to serve as a shorthand method of referring individually to each separate value inclusively falling within the range, unless otherwise indicated herein, and each separate value is incorporated into the specification as if it were individually recited herein.

DETAILED DESCRIPTION

Provided herein are compositions comprising recombinant resilins, and methods for their production.

Resilins have many unique properties compared to petroleum-based elastomers. Most notably, resilin has an extreme elastic efficiency, where very little of the energy input into deformation is lost as heat. Other desirable properties of resilin include, for example, desirable resilience, compressive elastic modulus, tensile elastic modulus, shear modulus, extension to break, maximum tensile strength, hardness, rebound, and compression set. Moreover, resilin is a protein, and therefore can be biodegraded, which makes it more environmentally friendly than petroleum-based polymers. Also, resilin is biocompatible and can therefore be used in applications that involve contact with humans or animals. Lastly, the mechanical properties of recombinant resilins can be tuned through varying protein sequence, protein structure, amount of intermolecular cross-linking and processing variables to produce elastomers designed for a universe of specific applications.

In some embodiments, the methods and compositions provided herein provide efficient means for producing large quantities of recombinant resilins. In some embodiments, large quantities of resilin and resilin-like polypeptides are obtained using recombinant host cells that secrete recombinant resilins via their secretory pathways. Such secretion of recombinant resilins a) avoids toxicity from intracellular accumulation of recombinant resilins, b) simplifies purification by eliminating cell disruption or protein refolding processes, and c) provides opportunities for post-translational events (e.g., proteolytic maturation, glycosylation, disulfide bond formation) that can modulate the properties of the recombinant resilins.

Compositions Comprising Recombinant Resilins

In some embodiments, the compositions provided herein comprise recombinant resilins.

FIG. 1 illustrates an example of a native resilin, which contains an N-terminal A-domain comprising a plurality of repeat units comprising the consensus amino acid sequence YGXP ("A-repeat"), where X is any amino acid; a chitin-binding type RR-2 (C) domain (Pfam reference PF00379; Rebers J E & Willis, J H. A conserved domain in anthropod cuticular proteins binds chitin. Insect Biochem Mol Biol 31:1083-1093); and a C-terminal B-domain comprising a plurality of repeat units comprising the consensus amino acid sequence UYZXZ ("B-repeat"), where U is glycine or serine; Z is serine, glycine, arginine, or proline; and X is any amino acid. Not all naturally occurring resilins have A-, C-, and B-domains. Native resilins produced by various insects typically have inexact repeats (i.e., quasi-repeats) within the A- and/or B-domains with some amino acid variation between the quasi-repeats.

In some embodiments, the recombinant resilins provided herein comprise one or more A-repeats. In some embodiments, the recombinant resilins comprise N-terminal A-domains comprising a plurality of blocks of A-repeat and/or quasi-A-repeat amino acid sub-sequences each with the consensus sequence SXXYGXP, where S is serine, X is an amino acid, Y is tyrosine, G is glycine, and P is proline.

In some embodiments, the recombinant resilins provided herein comprise one or more B-repeats. In some embodiments, the recombinant resilins comprise a C-terminal B-domain comprising a plurality of blocks of B-repeat and/or quasi-B-repeat amino acid sub-sequences each with the consensus sequence GYZXZZX and/or SYZXZZX, where G is glycine; Y is tyrosine; Z is serine, glycine, proline, or arginine; S is serine; and X is any amino acid.

In some embodiments, the recombinant resilins provided herein comprise one or more A-repeats. In some such embodiments, the recombinant resilins comprise between 1 and 100 A-repeats, or from 2 to 50 A-repeats, or from 5 to 50 A-repeats, or from 5 to 20 A-repeats.

In some embodiments, the recombinant resilins comprise one or more consensus sequences described by the formula, $$(X_1-X_2-X_3-X_4)_n \qquad (1)$$

wherein the brackets delineate a repeat or quasi-repeat of the consensus sequence;
wherein n describes the number of A-repeats or quasi-A-repeats, and is from 1 to 100, or from 2 to 50, or from 5 to 50, or from 5 to 20;
wherein $X_1$ is a motif that is 4 amino acids in length, wherein the first amino acid of $X_1$ is Y, and wherein the remaining amino acids of $X_1$ are GAP, GLP, GPP, GTP, or GVP;
wherein $X_2$ is a motif that is from 3 to 20 amino acids in length;
wherein $X_2$ comprises GGG, GGGG, N, NG, NN, NGN, NGNG, GQGG, GQGN, GQGQ, GQGQG, or 3 or more glycine residues, or wherein 50% or more of the residues of $X_2$ are either glycine or asparagine, or wherein 60% or more of the residues of $X_2$ are either glycine or asparagine, or wherein 70% or more of the residues of $X_2$ are either glycine or asparagine, or
wherein 80% or more of the residues of $X_2$ are either glycine or asparagine;
wherein $X_3$ is a motif that is from 2 to 6 amino acids in length, wherein $X_3$ is GG, LS, APS, GAG, GGG, KPS, RPS, or GGGG; and wherein $X_4$ is a motif that is from 1 to 2 amino acids in length, wherein $X_4$ is S, D, T, N, L, DS, DT, LS, SS, ST, TN, or TS.

In some such embodiments, the recombinant resilins comprise motifs $X_1$, $X_2$, $X_3$, and $X_4$ whereas in other embodiments, the recombinant resilins comprise motifs $X_1$, $X_2$, $X_3$, or $X_4$, or combinations thereof.

In some embodiments, the recombinant resilins provided herein comprise one or more B-repeats. In some such embodiments, the recombinant resilins comprise between 1 and 100 B-repeats, or from 2 to 50 A-repeats, or from 5 to 50 A-repeats, or from 5 to 20 A-repeats.

In some embodiments, the recombinant resilins comprise one or more consensus sequences described by the formula, $$(X_{11}-X_{12}-X_{13})_m \quad (2)$$

wherein the brackets delineate a repeat or quasi-repeat of the consensus sequence;
wherein m describes the number of B-repeats or quasi-B-repeats, and is from 1 to 100;
wherein $X_{11}$ is a motif that is from 1 to 5 amino acids in length, the first amino acid is Y, and where the remaining amino acids can comprise GAP, GPP, SSG, or SGG;
wherein $X_{12}$ is a motif that is from 2 to 5 amino acids in length and comprises GQ, GN, RPG, RPGGQ, RPGGN, SSS, SKG, or SN; and
wherein $X_{13}$ is a motif that is from 4 to 30 amino acids in length and comprises GG, DLG, GFG, GGG, RDG, SGG, SSS, GGSF, GNGG, GGAGG, or 3 or more glycine residues, or 30% or more of the residues are glycine, or 40% or more of the residues are glycine, or 50% or more of the residues are glycine, or 60% or more of the residues are glycine.

In some such embodiments, the recombinant resilins comprise motifs $X_{11}$, $X_{12}$, and $X_{13}$ whereas in other such embodiments, the recombinant resilins comprise motifs $X_{11}$, $X_{12}$, or $X_{13}$, or combinations thereof.

In some embodiments, the recombinant resilins provided herein comprise one or more A-repeats, one or more B-repeats, and/or one or more C-domain. In some embodiments, the recombinant resilins comprise one or more A-repeats or one or more B-repeats but not both. In some embodiments, the recombinant resilins comprise one or more A-repeats but not B-repeats or C-domains. In some embodiments, the recombinant resilins comprise one or more B-repeats but not A-repeats or C-domains. In embodiments in which the recombinant resilins comprise a C-domain, the C-domain can be situated either on the N-terminal or the C-terminal sides of the A-repeats or B-repeats, or between the A-repeats and the B-repeats.

In some embodiments, the recombinant resilins further comprise the sequence XXEPPVSYLPPS, where X is any amino acid. In some such embodiments, the sequence is located on the N-terminal side of an A-repeat or B-repeat.

In some embodiments, the recombinant resilins are full-length native resilins expressed in a non-native environment. In some embodiments, the recombinant resilins comprise a truncated version of native resilins. In some embodiments, the truncated native resilins comprise at least one A-repeat. In some embodiments, the truncated native resilins comprise at least one B-repeat. Non-limiting examples of full-length and truncated native resilins are provided as SEQ ID NOs: 1 through 44. In some embodiments, the recombinant resilins are full-length *Drosophila sechellia* resilin (SEQ ID NO: 1). In some embodiments, the recombinant resilins are truncated *Acromyrmex echinatior* resilin (SEQ ID NO: 4). In some embodiments, the recombinant resilins are full-length or truncated native resilins that are cross-linked in a non-native manner (e.g., less or more cross-linking, cross-linking via different amino acid residues).

In some embodiments, the recombinant resilins are modified full-length or truncated native resilins. In some embodiments, the recombinant resilins are at least 60%, at least 65%, at least 70%, at least 75%, at least 80%, at least 85%, at least 90%, at least 95%, or at least 98% identical to a full-length or truncated native resilin. In some embodiments, the recombinant resilins are at least 60%, at least 65%, at least 70%, at least 75%, at least 80%, at least 85%, at least 90%, at least 95%, or at least 98% identical to full-length *Drosophila sechellia* resilin (SEQ ID NO: 1). In some embodiments, the recombinant resilins are at least 60%, at least 65%, at least 70%, at least 75%, at least 80%, at least 85%, at least 90%, at least 95%, or at least 98% identical to truncated *Acromyrmex echinatior* resilin (SEQ ID NO: 4).

There are a number of different algorithms known in the art which can be used to measure nucleotide sequence or protein sequence identity. For instance, polynucleotide sequences can be compared using FASTA, Gap, or Bestfit, which are programs in Wisconsin Package Version 10.0, Genetics Computer Group (GCG), Madison, Wis. FASTA provides alignments and percent sequence identity of the regions of the best overlap between the query and search sequences. See, e.g., Pearson, Methods Enzymol. 183:63-98, 1990 (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., J. Mol. Biol. 215:403-410, 1990; Gish and States, Nature Genet. 3:266-272, 1993; Madden et al., Meth. Enzymol. 266:131-141, 1996; Altschul et al., Nucleic Acids Res. 25:3389-3402, 1997; Zhang and Madden, Genome Res. 7:649-656, 1997, especially blastp or tblastn (Altschul et al., Nucleic Acids Res. 25:3389-3402, 1997.

In some embodiments, the modified resilins differ from full-length or truncated native resilins in amino acid residues that are post-translationally modified (e.g., glycosylated, phosphorylated) such that the modified resilins have one or more different locations and/or different amounts and/or different types of post-translational modifications than the full-length or truncated native resilins. In some embodiments, the modified resilins differ from full-length or truncated native resilins in amino acid residues that are involved in cross-linking such that the modified resilins have one or more different locations and/or different amounts and/or different types of amino acids that are involved in cross-linking than full-length or truncated native resilins. In some such embodiments, the modified resilins differ from the full-length or truncated native resilin in comprising one or more additional or fewer tyrosine residues, one or more additional or fewer lysine residues, and/or one or more additional or fewer cysteine residues.

In some embodiments, the recombinant resilins comprise concatenated native or truncated native resilins or concatenated modified resilins. In some embodiments, the concatenated native or truncated native resilins or concatenated modified resilins comprise at least 2 A-repeats (e.g., 2, 3, 4, 5, 6, 7, 8, 9, 10, or more). In some embodiments, the concatenated truncated native resilins or concatenated modified resilins comprise at least 2 B-repeats (e.g., 2, 3, 4, 5, 6, 7, 8, 9, 10, or more).

The compositions provided herein comprise at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%; between 10% and 100%, 90%, 80%, 70%, 60%, 50%, 40%, 30%, or 20%; between 20% and 100%, 90%, 80%, 70%, 60%, 50%, 40%, or 30%; between 30% and 100%, 90%, 80%, 70%, 60%, 50%, or 40%; between 40% and 100%, 90%, 80%, 70%, 60%, or 50%; between 50% and 100%, 90%, 80%, 70%, or 60%; between 60% and 100%, 90%, 80%, or 70%; between 70% and 100%, 90%, or 80%;

between 80% and 100%, or 90%; or between 90% and 100% by weight of recombinant resilins. The recombinant resilins can be identical recombinant resilins or mixtures of recombinant resilins having at least 2 different amino acid sequences.

In some embodiments, the compositions provided herein have similar properties compared to compositions comprising native resilins. In other embodiments, the compositions provided herein have different properties compared to compositions comprising native resilins. Non-limited examples of such properties include resilience, compressive elastic modulus, tensile elastic modulus, shear modulus, extension to break, maximum tensile strength, hardness, rebound, and compression set. Parameters that can be modified to obtain compositions with specific mechanical properties include, for example, the length and/or sequence of the recombinant resilins, the extent and/or type of post-translational modifications of the recombinant resilins, and/or the extent and/or type of cross-linking of the recombinant resilins.

In some embodiments, mechanical properties such as maximum tensile strength, compressive elastic modulus, tensile elastic modulus, shear modulus, extension to break and resilience can be measured using many different types of tensile and compression systems that conduct stress-strain measurements on elastomeric samples. The resulting stress-strain curves, including curves with hysteresis, can be measured in tension or compression. In some embodiments, tension and compression test systems can apply a strain to a sample and measure the resulting force using a load cell. In some embodiments, the mechanical properties can be measured at the macroscopic scale (e.g., using macroscopic compression testers), microscopic, or nanoscopic scale (e.g., using atomic-force microscopy (AFM) or nanoindentation measurements). In some embodiments, the compressive mechanical properties of elastomers can be measured according to the standard ASTM D575-91(2012) Standard Test Methods for Rubber Properties in Compression. Mechanical measurements of elastomers in tension can be performed using ASTM D412-15a Standard Test Methods for Vulcanized Rubber and Thermoplastic Elastomers—Tension. In some embodiments, tear strength of elastomers can be performed using ASTM D624-00 Standard Test Method for Tear Strength of Conventional Vulcanized Rubber and Thermoplastic Elastomers. In some embodiments, mechanical properties of slab, bonded, and molded elastomers can be performed using ASTM D3574-11 Standard Test Methods for Flexible Cellular Materials—Slab, Bonded, and Molded Urethane Foams. In some embodiments, the mechanical properties of elastomers can be measured using ASTM D5992-96(2011) Standard Guide for Dynamic Testing of Vulcanized Rubber and Rubber-Like Materials Using Vibratory Methods.

In some embodiments, the compositions provided herein have a resilience of greater than 50%, greater than 60%, greater than 70%, greater than 80%, greater than 90%, or greater than 95%; from 50% to 100%, 90%, 80%, 70%, or 60%; from 60% to 100%, 90%, 80%, or 70%; from 70% to 100%, 90%, or 80%; from 80% to 100%, or 90%; from 90% to 100%; from 95% to 100%, from 90% to 99%, or from 95% to 99%.

In some embodiments, the compositions provided herein have a compressive elastic modulus of less than 10 MPa, less than 7 MPa, less than 5 MPa, less than 2 MPa, less than 1 MPa, less than 0.5 MPa, or less than 0.1 MPa; from 0.01 MPa to 10 MPa, 7 MPa, 5 MPa, 2 MPa, 1 MPa, 0.5 MPa, or 0.1 MPa; from 0.1 MPa to 10 MPa, 7 MPa, 5 MPa, 2 MPa, 1 MPa, or 0.5 MPa; from 0.5 MPa to 10 MPa, 7 MPa, 5 MPa, 2 MPa, or 1 MPa; from 1 MPa to 10 MPa, 7 MPa, 5 MPa, or 2 MPa; from 2 MPa to 10 MPa, 7 MPa, or 5 MPa; from 5 MPa to 10 MPa, or 7 MPa; or from 7 MPa to 10 MPa. In some embodiments, the compressive elastic modulus of a composition can be measured as defined by the ASTM D575-91(2012) Standard Test Methods for Rubber Properties in Compression.

In some embodiments, the compositions provided herein have a tensile elastic modulus of less than 10 MPa, less than 7 MPa, less than 5 MPa, less than 2 MPa, less than 1 MPa, less than 0.5 MPa, or less than 0.1 MPa; from 0.01 MPa to 10 MPa, 7 MPa, 5 MPa, 2 MPa, 1 MPa, or 0.5 MPa; from 0.5 MPa to 10 MPa, 7 MPa, 5 MPa, 2 MPa, or 1 MPa; from 1 MPa to 10 MPa, 7 MPa, 5 MPa, or 2 MPa; from 2 MPa to 10 MPa, 7 MPa, or 5 MPa; from 5 MPa to 10 MPa, or 7 MPa; or from 7 MPa to 10 MPa.

In some embodiments, the compositions provided herein have a shear modulus of less than 1 MPa, less than 100 kPa, less than 50 kPa, less than 20 kPa, less than 10 kPa, or less than 1 kPa; from 0.1 kPa to 1 MPa, 100 kPa, 50 kPa, 20 kPa, 10 kPa, or 1 kPa; from 1 kPa to 1 MPa, 100 kPa, 50 kPa, 20 kPa, or 10 kPa; from 10 kPa to 1 MPa, 100 kPa, 50 kPa, or 20 kPa; from 20 kPa to 1 MPa, 100 kPa, or 50 kPa; from 50 kPa to 1 MPa, or 100 kPa; or from 100 kPa to 1 MPa.

In some embodiments, the compositions provided herein have an extension to break of greater than 1%, greater than 10%, greater than 50%, greater than 100%, greater than 300%, or greater than 500%; from 1% to 500%, 300%, 100%, 50%, or 10%; from 10% to 500%, 300%, 100%, or 50%; from 50% to 500%, 300%, or 100%; from 100% to 500%, or 300%; or from 300% to 500%.

In some embodiments, the compositions provided herein have a maximum tensile strength of greater than 0.1 kPa, greater than 1 kPa, greater than 2 kPa, greater than 5 kPa, or greater than 10 kPa; from 0.1 kPa to 100 kPa, 10 kPa, 5 kPa, 2 kPa, or 1 kPa; from 1 kPa to 100 kPa, 10 kPa, 5 kPa, or 2 kPa; from 2 kPa to 100 kPa, 10 kPa, or 5 kPa; from 5 kPa to 100 kPa, or 10 kPa; or from 10 kPa to 100 kPa.

In some embodiments, mechanical properties such as hardness and compressive elastic modulus can be measured using indentation and nanoindentation measurement systems. In some embodiments, indentation measurements utilizing a tip to indent the sample to a given amount of strain are used to measure the hardness and compressive elastic modulus of resilin, and the resulting force is measured using a load cell. In some embodiments, different tip shapes can be used including Vickers and Berkovich shaped tips. In some embodiments, the hardness measured by indentation techniques is characterized by the relation, Hardness=(Peak Force)/(Contact Area).

In some embodiments, the hardness in polymers, elastomers, and rubbers can be measured using a durometer. In some embodiments the hardness of an elastomer can be measured using the standard ASTM D2240, which recognizes twelve different durometer scales using combinations of specific spring forces and indentor configurations. The most common scales are the Shore 00, A and D Hardness Scales. Hardness scales range from 0 to 100, where 0 is softer material and 100 is harder material.

In some embodiments, the compositions provided herein have a Shore 00 Hardness of less than 90, less than 80, less than 70, less than 60, less than 50, less than 40, less than 30, or less than 20; from 10 to 90, 80, 70, 60, 50, 40, 30, or 20; from 20 to 90, 80, 70, 60, 50, 40, or 30; from 30 to 90, 80, 70, 60, 50, or 40; from 40 to 90, 80, 70, 60, or 50; from 50 to 90, 80, 70, or 60; from 60 to 90, 80, or 70; from 70 to 90, or 80; or from 80 to 90. In some embodiments, hardness measurements in resilin are performed according to ASTM D2240.

As used here, the term "rebound" refers to a particular measure of resilience. In some embodiments, rebound can be measured with a number of different tools including pendulum tools and dropped balls. In the pendulum type measurements, RB, commonly called percentage rebound, is determined from the equation:

$$RB = \frac{[1 - \cos(\text{angle of rebound})]}{[1 - \cos(\text{originial angle})]} \times 100$$

The rebound resilience can be calculated as:

$$R = \frac{h}{H}$$

where h=apex height of the rebound, and H=initial height. The rebound resilience can also be determined by the measurement of the angle of rebound. Some examples of test methods for determining rebound in elastomers are ASTM D2632-15 and ASTM D7121-05(2012).

In some embodiments, the compositions provided herein have a rebound greater than 50%, greater than 60%, greater than 70%, greater than 80%, greater than 90%, or greater than 95%; from 50% to 100%, 90%, 80%, 70%, or 60%; from 60% to 100%, 90%, 80%, or 70%; from 70% to 100%, 90%, or 80%; from 80% to 100%, or 90%; from 90% to 100%; from 95% to 100%, from 90% to 99%, or from 95% to 99%. In some embodiments, rebound measurements in resilin are performed according to ASTM D2632-15, or ASTM D7121-05(2012).

As used herein, the term "compression set" refers to a measure of the permanent deformation remaining after an applied force is removed. In some embodiments, compression set can be measured in different ways, including compression set under constant force in air (referred to as Compression Set A), compression set under constant deflection in air (referred to as Compression Set B), and compression set under constant deflection in air considering material hardness (referred to as Compression Set C). Compression Set A ($C_A$) is calculated by the following expression: $C_A = [(t_o-t_i)/t_o] \times 100$, where $t_o$ is the original specimen thickness, and $t_i$ is the specimen thickness after testing). Compression set B ($C_B$) is given by $C_B = [(t_o-t_i)/(t_o-t_n)]100$, where $t_o$ is the original specimen thickness, $t_i$ is the specimen thickness after testing, and $t_o$ is the spacer thickness or the specimen thickness during the test. Some examples of test methods for determining compression set in elastomers are ASTM D3574-11 and ASTM D395-16.

In some embodiments, the compositions provided herein have a Compression Set A or a Compression Set B of greater than 50%, greater than 60%, greater than 70%, greater than 80%, greater than 90%, or greater than 95%; from 50% to 100%, 90%, 80%, 70%, or 60%; from 60% to 100%, 90%, 80%, or 70%; from 70% to 100%, 90%, or 80%; from 80% to 100%, or 90%; from 90% to 100%; from 95% to 100%, from 90% to 99%, or from 95% to 99%. In some embodiments, compression set measurements in resilin are performed according to ASTM D3574-11 and ASTM D395-16.

The processing and forming of resilin into products can take many forms for different applications. Accordingly, the compositions provided herein can have any shape and form, including but not limited to gels, porous sponges, films, machinable solids, cast forms, molded forms, and composites.

The compositions provided herein have a number of uses, including but not limited to applications in aerospace, automotive, sporting equipment, vibration isolation, footwear, and clothing among others. Some applications from these categories are listed as non-limiting examples. Due to the desirable elastic efficiency, resilin can be used as an energy storage device (e.g., a rubber band) for storing and recovering mechanical energy. Automobile suspension systems can be improved by application of resilin bushings to keep more tire contact on the road when going over bumps and through potholes at speed. Additionally, there are a number of sporting equipment applications for resilin with differently tuned mechanical properties including cores of golf balls, tennis racket grips, golf club grips, and table tennis paddles.

An application of particular interest is footwear due to the unique properties of resilin compositions provided herein. As an insole or midsole, resilin can improve the comfort and bioefficiency of shoes by cushioning the foot strike and restoring more of the energy from that footstrike as forward momentum. As a midsole, resilin can make up the entire midsole or be encapsulated within another material to complement its properties (e.g., an abrasion or wear resistant material, or a material tuned for traction). The resilin midsole can also contain a plurality of resilin materials with differently tuned mechanical properties that work in concert to provide enhanced performance (e.g., softer heel strike area and firmer arch support).

As used herein, the term "density" refers to the mass of the sample divided by the volume. In some embodiments, the density of an elastomer can be determined using a pycnometer with alcohol in place of water to eliminate air bubbles. In some embodiments, the density of an elastomer can be determined using a hydrostatic method. As used herein, the term "compressed volume density" refers to the ratio of the sample mass to the compressed volume of the sample, where the "compressed volume" is defined as the final equilibrium volume attained by an elastomeric sample when it is subjected to a compressive force sufficient to cause it to flow until it fully conforms to the surrounding shape of the piston-cylinder test chamber enclosure. In some embodiments, the compressed volume density of an elastomer can be determined using a compressed volume densimeter.

In some embodiments, the compositions provided herein have a density or a compressed volume density are from 0.5 mg/cm$^3$ to 2.0 mg/cm$^3$, or from 1.0 mg/cm$^3$ to 1.5 mg/cm$^3$, or from 1.1 mg/cm$^3$ to 1.4 mg/cm$^3$, or from 1.2 mg/cm$^3$ to 1.35 mg/cm$^3$. In some embodiments, the determination of the density or the compressed volume density of elastomers can be performed using ASTM D297-15 Standard Test Methods for Rubber Products—Chemical Analysis.

Recombinant Resilin Vectors, Recombinant Host Cells, and Fermentations

Further provided herein are vectors encoding recombinant resilins, recombinant host cells comprising such vectors, and fermentations comprising such recombinant host cells and recombinant resilins.

In some embodiments, the vectors provided herein comprise secreted resilin coding sequences, which encode a resilin polypeptide fused at its N-terminus to a secretion signal and optionally at its C-terminus to a tag peptide or polypeptide. In some embodiments, the vectors comprise secreted resilin coding sequences that are codon-optimized for expression in a particular host cell.

Suitable secretion signals are secretion signals that mediate secretion of polypeptides in the recombinant host cells provided herein. Non-limiting examples of suitable secretion signals are the secretion signals of the alpha mating factor (α-MF) of *Saccharomyces cerevisiae*, acid phosphatase (PHO1) of *Pichia pastoris*, and phytohemagglutinin (PHA-E) from the common bean *Phaseolus vulgaris*. Additional secretion signals are known in the art, or can be identified by identification of proteins secreted by a host cell followed by genomic analysis of the secreted proteins and identification of the non-translated N-terminal sequences (see, for example, Huang et al. A proteomic analysis of the *Pichia pastoris* secretome in methanol-induced cultures. Appl Microbiol Biotechnol. 2011 April; 90(1):235-47).

The resilins encoded by the secreted resilin coding sequences can be further fused to tag peptides or polypeptides. Non-limiting examples of tag peptides or polypeptides include affinity tags (i.e., peptides or polypeptides that bind to certain agents or matrices), solubilization tags (i.e., peptides or polypeptides that assist in proper folding of proteins and prevent precipitation), chromatography tags (i.e., peptides or polypeptides that alter the chromatographic properties of a protein to afford different resolution across a particular separation techniques), epitope tags (i.e., peptides or polypeptides that are bound by antibodies), fluorescence tags (i.e., peptides or polypeptides that upon excitation with short-wavelength light emit high-wavelength light), chromogenic tags (i.e., peptides or polypeptides that absorb specific segments of the visible light spectrum), enzyme substrate tags (i.e., peptides or polypeptides that are the substrates for specific enzymatic reactions), chemical substrate tags (i.e., peptides or polypeptides that are the substrates for specific chemical modifications), or combinations thereof. Non-limiting examples of suitable affinity tags include maltose binding protein (MBP), glutathione-S-transferase (GST), poly(His) tag, SBP-tag, Strep-tag, and calmodulin-tag. Non-limiting examples of suitable solubility tags include thioredoxin (TRX), poly(NANP), MBP, and GST. Non-limiting examples of chromatography tags include polyanionic amino acids (e.g., FLAG-tag [GDYKDDDDKDYKDDDDKDYKDDDDK (SEQ ID NO: 45)]) and polyglutamate tag. Non-limiting examples of epitope tags include V5-tag, VSV-tag, Myc-tag, HA-tag, E-tag, NE-tag, and FLAG-tag. Non-limiting examples of fluorescence tags include green fluorescent protein (GFP), blue fluorescent protein (BFP), cyan fluorescent protein (CFP), yellow fluorescent protein (YFP), orange fluorescent protein (OFP), red fluorescent protein (RFP), and derivatives thereof. Non-limiting examples of chromogenic tags include non-fluorescent members of the GFP-like family of proteins (e.g., BlitzenBlue, DonnerMagenta; DNA2.0, Neward, CA). Non-limiting examples of enzyme substrate tags include peptides or polypeptides comprising a lysine within a sequence suitable for biotinilation (e.g., AviTag, Biotin Carboxyl Carrier Protein [BCCP]). Non-limiting examples of chemical substrate tags include substrates suitable for reaction with FIAsH-EDT2. The fusion of the C-terminal peptide or polypeptide to the resilin can be cleavable (e.g., by TEV protease, thrombin, factor Xa, or enteropeptidase) on non-cleavable.

In some embodiments, the vectors comprise single secreted resilin coding sequences. In other embodiments, the vectors comprise 2 or more (e.g., 3, 4, or 5) secreted resilin coding sequences. In some such embodiments, the secreted resilin coding sequences are identical. In other such embodiments, at least 2 of the secreted resilin coding sequences are not identical. In embodiments in which at least 2 of the secreted resilin coding sequences are not identical, the at least 2 secreted resilin coding sequences can differ from each other in the resilins and/or in the secretion signals and/or the optional tag peptides or polypeptides they encode.

In some embodiments, the vectors comprise promoters that are operably linked to the secreted resilin coding sequences such that they drive the expression of the secreted resilin coding sequences. The promotors can be constitutive promoters or inducible promoters. In some embodiments, induction of the inducible promoter occurs via glucose repression, galactose induction, sucrose induction, phosphate repression, thiamine repression, or methanol induction. Suitable promoters include promoters that mediate expression of proteins in the recombinant host cells provided herein. Non-limiting examples of suitable promoters include the AOX1 promoter, GAP promoter, LAC4-PBI promoter, T7 promoter, TAC promoter, GCW14 promoter, GAL1 promoter, λPL promoter, λPR promoter, beta-lactamase promoter, spa promoter, CYC1 promoter, TDH3 promoter, GPD promoter, TEF1 promoter, ENO2 promoter, PGL1 promoter, SUC2 promoter, ADH1 promoter, ADH2 promoter, HXT7 promoter, PHO5 promoter, and CLB1 promoter. Additional promoters that can be used to facilitate expression of the secreted resilin coding sequences are known in the art.

In some embodiments, the vectors comprise terminators that are operably linked to the secreted resilin coding sequences such that they effect termination of transcription of the secreted resilin coding sequences. Suitable terminators include terminators that terminate transcription in the recombinant host cells provided herein. Non-limiting examples of suitable terminators include the AOX1 terminator, PGK1 terminator, and TPS1 terminator. Additional terminators that effect termination of transcription of the secreted resilin coding sequences are known in the art.

In embodiments in which the vectors comprise 2 or more resilin coding sequences, the 2 or more resilin coding sequences can be operably linked to the same promoters and/or terminators or to 2 or more different promoters and/or terminators.

The vectors provided herein can further comprise elements suitable for propagation of the vectors in recombinant host cells. Non-limiting examples of such elements include bacterial origins of replication and selection markers (e.g., antibiotic resistance genes, auxotrophic markers). Bacterial origins of replication and selection markers are known in the art. In some embodiments, the selection marker is a drug resistant marker. A drug resistant maker enables cells to detoxify an exogenously added drug that would otherwise kill the cell. Illustrative examples of drug resistant markers include but are not limited to those for resistance to antibiotics such as ampicillin, tetracycline, kanamycin, bleomycin, streptomycin, hygromycin, neomycin, Zeocin™, and the like. In some embodiments, the selection marker is an auxotrophic marker. An auxotrophic marker allows cells to synthesize an essential component (usually an amino acid) while grown in media that lacks that essential component. Selectable auxotrophic gene sequences include, for example, hisD, which allows growth in histidine-free media in the presence of histidinol. Other selection markers suitable for the vectors of the present invention include a bleomycin-resistance gene, a metallothionein gene, a hygromycin B-phosphotransferase gene, the AURI gene, an adenosine deaminase gene, an aminoglycoside phosphotransferase gene, a dihydrofolate reductase gene, a thymidine kinase gene, and a xanthine-guanine phosphoribosyltransferase gene.

The vectors of the present invention can further comprise targeting sequences that direct integration of the secreted resilin coding sequences to specific locations in the genome of host cells. Non-limiting examples of such targeting sequences include nucleotide sequences that are identical to nucleotide sequences present in the genome of a host cell. In some embodiments, the targeting sequences are identical to repetitive elements in the genome of host cells. In some embodiments, the targeting sequences are identical to transposable elements in the genome of host cells.

In some embodiments, recombinant host cells are provided herein that comprise the vectors described herein. In some embodiments, the vectors are stably integrated within the genome (e.g., a chromosome) of the recombinant host cells, e.g., via homologous recombination or targeted integration. Non-limiting examples of suitable sites for genomic integration include the Ty1 loci in the *Saccharomyces cerevisiae* genome, the rDNA and HSP82 loci in the *Pichia pastoris* genome, and transposable elements that have copies scattered throughout the genome of the recombinant host cells. In other embodiments, the vectors are not stably integrated within the genome of the recombinant host cells but rather are extrachromosomal.

Recombinant host cells can be of mammalian, plant, algae, fungi, or microbe origin. Non-limiting examples of suitable fungi include methylotrophic yeast, filamentous yeast, *Arxula adeninivorans, Aspergillus niger, Aspergillus niger* var. *awamori, Aspergillus oryzae, Candida etchellsii, Candida guilliermondii, Candida humilis, Candida lipolytica, Candida pseudotropicalis, Candida utilis, Candida versatilis, Debaryomyces hansenii, Endothia parasitica, Eremothecium ashbyii, Fusarium moniliforme, Hansenula polymorpha, Kluyveromyces lactis, Kluyveromyces marxianus, Kluyveromyces thermotolerans, Morteirella vinaceae* var. *raffinoseutilizer, Mucor miehei, Mucor miehei* var. Cooney et Emerson, *Mucor pusillus Lindt, Penicillium roquefortii, Pichia methanolica, Pichia pastoris (Komagataella phaffii), Pichia (Scheffersomyces) stipitis, Rhizopus niveus, Rhodotorula* sp., *Saccharomyces bayanus, Saccharomyces beticus, Saccharomyces cerevisiae, Saccharomyces chevalieri, Saccharomyces diastaticus, Saccharomyces ellipsoideus, Saccharomyces exiguus, Saccharomyces florentinus, Saccharomyces fragilis, Saccharomyces pastorianus, Saccharomyces pombe, Saccharomyces sake, Saccharomyces uvarum, Sporidiobolus johnsonii, Sporidiobolus salmonicolor, Sporobolomyces roseus, Trichoderma reesi, Xanthophyllomyces dendrorhous, Yarrowia lipolytica, Zygosaccharomyces rouxii*, and derivatives and crosses thereof.

Non-limiting examples of suitable microbes include *Acetobacter* suboxydans, *Acetobacter xylinum, Actinoplane missouriensis, Arthrospira platensis, Arthrospira maxima, Bacillus cereus, Bacillus coagulans, Bacillus licheniformis, Bacillus stearothermophilus, Bacillus subtilis, Escherichia coli, Lactobacillus acidophilus, Lactobacillus bulgaricus, Lactobacillus reuteri, Lactococcus lactis, Lactococcus lactis* Lancefield Group N, *Leuconostoc citrovorum, Leuconostoc dextranicum, Leuconostoc mesenteroides* strain NRRL B-512(F), *Micrococcus lysodeikticus, Spirulina, Streptococcus cremoris, Streptococcus lactis, Streptococcus lactis* subspecies *diacetylactis, Streptococcus thermophilus, Streptomyces chattanoogensis, Streptomyces griseus, Streptomyces natalensis, Streptomyces olivaceus, Streptomyces olivochromogenes, Streptomyces rubiginosus, Xanthomonas campestris*, and derivatives and crosses thereof. Additional strains that can be used as recombinant host cells are known in the art. It should be understood that the term "recombinant host cell" is intended to refer not only to the particular subject cell but to the progeny of such a cell. Because certain modifications may occur in succeeding generations due to either mutation or environmental influences, such progeny may not, in fact, be identical to the parent cell, but is still included within the scope of the term "recombinant host cell" as used herein.

In some embodiments, the recombinant host cells comprise genetic modifications that improve production of the recombinant resilins provided herein. Non-limiting examples of such genetic modifications include altered promoters, altered kinase activities, altered protein folding activities, altered protein secretion activities, altered gene expression induction pathways, and altered protease activities.

The recombinant host cells provided herein are generated by transforming cells of suitable origin with vectors provided herein. For such transformation, the vectors can be circularized or be linear. Recombinant host cell transformants comprising the vectors can be readily identified, e.g., by virtue of expressing drug resistance or auxotrophic markers encoded by the vectors that permit selection for or against growth of cells, or by other means (e.g., detection of light emitting peptide comprised in vectors, molecular analysis of individual recombinant host cell colonies, e.g., by restriction enzyme mapping, PCR amplification, or sequence analysis of isolated extrachromosomal vectors or chromosomal integration sites).

In some embodiments, the recombinant host cells provided herein can produce high titers of the recombinant resilins provided herein. In some such embodiments, the recombinant host cells produce the recombinant resilins at a rate of greater than 2 mg resilin/g dry cell weight/hour, 4 mg resilin/g dry cell weight/hour, 6 mg resilin/g dry cell weight/hour, 8 mg resilin/g dry cell weight/hour, 10 mg resilin/g dry cell weight/hour, 12 mg resilin/g dry cell weight/hour, 14 mg resilin/g dry cell weight/hour, 16 mg resilin/g dry cell weight/hour, 18 mg resilin/g dry cell weight/hour, 20 mg resilin/g dry cell weight/hour, 25 mg resilin/g dry cell weight/hour, or 30 mg resilin/g dry cell weight/hour; from 2 to 40, 30, 20, 10, or 5 mg resilin/g dry cell weight/hour; from 5 to 40, 30, 20, or 10 mg resilin/g dry cell weight/hour; from 10 to 40, 30, or 20 mg resilin/g dry cell weight/hour; from 20 to 40, or 30 mg resilin/g dry cell weight/hour; or from 30 to 40 mg resilin/g dry cell weight/hour. In other such embodiments, the recombinant host cells secrete the recombinant resilins at a rate of greater than 2 mg resilin/g dry cell weight/hour, 4 mg resilin/g dry cell weight/hour, 6 mg resilin/g dry cell weight/hour, 8 mg resilin/g dry cell weight/hour, 10 mg resilin/g dry cell weight/hour, 12 mg resilin/g dry cell weight/hour, 14 mg resilin/g dry cell weight/hour, 16 mg resilin/g dry cell weight/hour, 18 mg resilin/g dry cell weight/hour, 20 mg resilin/g dry cell weight/hour, 25 mg resilin/g dry cell weight/hour, or 30 mg resilin/g dry cell weight/hour; from 2 to 40, 30, 20, 10, or 5 mg resilin/g dry cell weight/hour; from 5 to 40, 30, 20, or 10 mg resilin/g dry cell weight/hour; from 10 to 40, 30, or 20 mg resilin/g dry cell weight/hour; from 20 to 40, or 30 mg resilin/g dry cell weight/hour; or from 30 to 40 mg resilin/g dry cell weight/hour. The identities of the recombinant resilins produced can be confirmed by HPLC quantification, Western blot analysis, polyacrylamide gel electrophoresis, and 2-dimensional mass spectroscopy (2D-MS/MS) sequence identification.

In some embodiments, the recombinant host cells provided herein have high secreted fractions of the recombinant resilins provided herein. In some such embodiments, the recombinant host cells have secreted fractions of recombinant resilient that is greater than 50%, 60%, 70%, 80%, or 90%; from 50% to 100%, 90%, 80%, 70%, or 60%; from 60% to 100%, 90%, 80%, or 70%; from 70% to 100%, 90%, or 80%; from 90% to 100%, or 90%; or from 90% to 100%.

Production and secretion of recombinant resilins can be influenced by the number of copies of the secreted resilin coding sequences comprised in the recombinant host cells and/or the rate of transcription of the secreted resilin coding sequences comprised in the recombinant host cells. In some embodiments, the recombinant host cells comprise a single secreted resilin coding sequence. In other embodiments, the recombinant host cells comprise 2 or more (e.g., 3, 4, 5, or more) secreted resilin coding sequences. In some embodiments, the recombinant host cells comprise secreted resilin coding sequences that are operably linked to strong promoters. Non-limiting examples of strong promoters include the pGCW14 promoter of *Pichia pastoris*. In some embodiments, the recombinant host cells comprise secreted resilin coding sequences that are operably linked to medium promoters. Non-limiting examples of such medium promoters include the pGAP promoter of *Pichia pastoris*. In some embodiments, the recombinant host cells comprise coding sequences encoding resilins under the control of weak promoters.

The fermentations provided herein comprise recombinant host cells described herein and a culture medium suitable for growing the recombinant host cells.

The fermentations are obtained by culturing the recombinant host cells in culture media that provide nutrients needed by the recombinant host cells for cell survival and/or growth, and for secretion of the recombinant resilins. Such culture media typically contain an excess carbon source. Non-limiting examples of suitable carbon sources include monosaccharides, disaccharides, polysaccharides, and combinations thereof. Non-limiting examples of suitable monosaccharides include glucose, galactose, mannose, fructose, ribose, xylose, arabinose, ribose, and combinations thereof. Non-limiting examples of suitable disaccharides include sucrose, lactose, maltose, trehalose, cellobiose, and combinations thereof. Non-limiting examples of suitable polysaccharides include raffinose, starch, glycogen, glycan, cellulose, chitin, and combinations thereof.

In some embodiments, the fermentations comprise recombinant resilins in amounts of at least 1%, 5%, 10%, 20%, or 30%; from 1% to 100%, 90%, 80%, 70%, 60%, 50%, 40%, 30%, 20%, or 10%; from 10% to 100%, 90%, 80%, 70%, 60%, 50%, 40%, 30%, or 20%; from 20% to 100%, 90%, 80%, 70%, 60%, 50%, 40%, or 30%; from 30% to 100%, 90%, 80%, 70%, 60%, 50%, or 40%; from 40% to 100%, 90%, 80%, 70%, 60%, or 50%; from 50% to 100%, 90%, 80%, 70%, or 60%; from 60% to 100%, 90%, 80%, or 70%; from 70% to 100%, 90%, or 80%; from 80% to 100%, or 90%; or from 90% to 100% by weight of the total fermentation.

In some embodiments, the fermentations comprise recombinant resilin in an amount of at least 2 g/L, 5 g/L, 10 g/L, 15 g/L, 20 g/L, 25 g/L, or 30 g/L; from 2 g/L to 300 g/L, 200 g/L, 100 g/L, 90 g/L, 80 g/L, 70 g/L, 60 g/L, 50 g/L, 40 g/L, 30 g/L, 20 g/L, or 10 g/L; from 10 g/L to 300 g/L, 200 g/L, 100 g/L, 90 g/L, 80 g/L, 70 g/L, 60 g/L, 50 g/L, 40 g/L, 30 g/L, or 20 g/L; from 20 g/L to 300 g/L, 200 g/L, 100 g/L, 90 g/L, 80 g/L, 70 g/L, 60 g/L, 50 g/L, 40 g/L, or 30 g/L; from 30 g/L to 300 g/L, 200 g/L, 100 g/L, 90 g/L, 80 g/L, 70 g/L, 60 g/L, 50 g/L, or 40 g/L; from 40 g/L to 300 g/L, 200 g/L, 100 g/L, 90 g/L, 80 g/L, 70 g/L, 60 g/L, or 50 g/L; from 50 g/L to 300 g/L, 200 g/L, 100 g/L, 90 g/L, 80 g/L, 70 g/L, or 60 g/L; from 60 g/L to 300 g/L, 200 g/L, 100 g/L, 90 g/L, 80 g/L, or 70 g/L; from 70 g/L to 300 g/L, 200 g/L, 100 g/L, 90 g/L, or 80 g/L; from 80 g/L to 300 g/L, 200 g/L, 100 g/L, or 90 g/L; from 90 g/L to 300 g/L, 200 g/L, or 100 g/L; from 100 g/L to 300 g/L, or 200 g/L; or from 200 g/L to 300 g/L.

Methods

Further provided herein are methods for the production of the recombinant resilins described herein.

The methods are generally performed according to conventional methods well known in the art and as described in various general and more specific references that are cited and discussed throughout the present specification unless otherwise indicated. See, e.g., Sambrook et al., Molecular Cloning: A Laboratory Manual, 2d ed., Cold Spring Harbor Laboratory Press, Cold Spring Harbor, N.Y., 1989; Ausubel et al., Current Protocols in Molecular Biology, Greene Publishing Associates, 1992, and Supplements to 2002); Harlow and Lane, Antibodies: A Laboratory Manual, Cold Spring Harbor Laboratory Press, Cold Spring Harbor, N.Y., 1990; Taylor and Drickamer, Introduction to Glycobiology, Oxford Univ. Press, 2003; Worthington Enzyme Manual, Worthington Biochemical Corp., Freehold, N.J.; Handbook of Biochemistry: Section A Proteins, Vol I, CRC Press, 1976; Handbook of Biochemistry: Section A Proteins, Vol II, CRC Press, 1976; Essentials of Glycobiology, Cold Spring Harbor Laboratory Press, 1999.

In some embodiments, a novel method is utilized to secrete resilin extracellularly from a host cell. In some embodiments, the method comprises constructing a vector comprising a secreted resilin coding sequence (step 1001 in FIG. 2), transforming the vector into a host cell (step 1002 in FIG. 2), and then culturing the recombinant host cells to secrete resilin extracellularly (step 1003 in FIG. 2). In some embodiments, the method includes secreting the resilin extracellularly at a rate greater than 2 mg resilin/g dry cell weight/hour, 4 mg resilin/g dry cell weight/hour, 6 mg resilin/g dry cell weight/hour, 8 mg resilin/g dry cell weight/hour, 10 mg resilin/g dry cell weight/hour, 12 mg resilin/g dry cell weight/hour, 14 mg resilin/g dry cell weight/hour, 16 mg resilin/g dry cell weight/hour, 18 mg resilin/g dry cell weight/hour, 20 mg resilin/g dry cell weight/hour, 25 mg resilin/g dry cell weight/hour, or 30 mg resilin/g dry cell weight/hour; from 2 to 40, 30, 20, 10, or 5 mg resilin/g dry cell weight/hour; from 5 to 40, 30, 20, or 10 mg resilin/g dry cell weight/hour; from 10 to 40, 30, or 20 mg resilin/g dry cell weight/hour; from 20 to 40, or 30 mg resilin/g dry cell weight/hour; or from 30 to 40 mg resilin/g dry cell weight/hour. In some embodiments, the secreted resilin is then purified (step 1004 in FIG. 2), and the purified resilin is cross-linked to form an elastomer (step 1005 in FIG. 2). In some embodiments, the methods provided herein comprise the step of transforming cells with vectors provided herein to obtain recombinant host cells provided herein (step 1002 in FIG. 2). Methods for transforming cells with vectors are well-known in the art. Non-limiting examples of such methods include calcium phosphate transfection, dendrimer transfection, liposome transfection (e.g., cationic liposome transfection), cationic polymer transfection, electroporation, cell squeezing, sonoporation, optical transfection, protoplast fusion, impalefection, hydrodynamic delivery, gene gun, magnetofection, and viral transduction. One skilled in the art is able to select one or more suitable methods for transforming cells with vectors provided herein based on the knowledge in the art that certain techniques for introducing vectors work better for certain types of cells.

Figure 2:
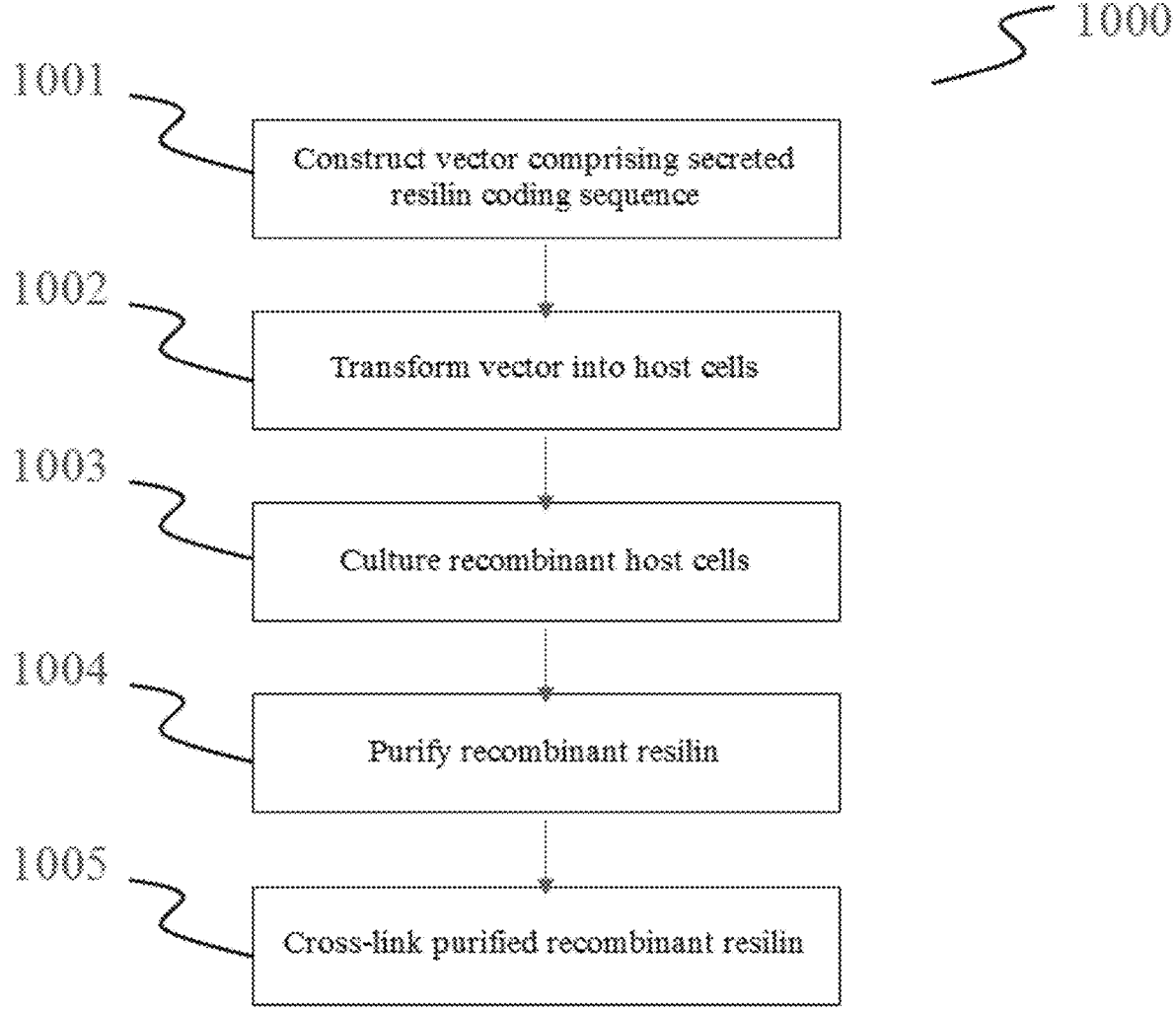
FIG. 2 is a flow diagram of methods for the production of compositions comprising recombinant resilins.

In some embodiments, the methods further comprise the step of culturing the recombinant host cells provided herein in culture media under conditions suitable for obtaining the fermentations provided herein (step 1003 in FIG. 2). In some embodiments, the conditions and culture media are suitable to facilitate secretion of the recombinant proteins from the recombinant host cells into the culture media. Suitable culture media for use in these methods are known in the art, as are suitable culture conditions. Exemplary details of culturing yeast host cells are described in Idiris et al., Appl. Microbiol. Biotechnol. 86:403-417, 2010; Zhang et al., Biotechnol. Bioprocess. Eng. 5:275-287, 2000; Zhu, Biotechnol. Adv. 30:1158-1170, 2012; Li et al., MAbs 2:466-477, 2010.

In some embodiments, the methods further comprise the step of purifying secreted recombinant resilins from the fermentations provided herein to obtain the recombinant resilins provided herein (step 1004 in FIG. 2). Purification can occur by a variety of methods known in the art for purifying secreted proteins from fermentations. Common steps in such methods include centrifugation (to remove cells) followed by precipitation of the proteins using precipitants or other suitable cosmotropes (e.g., ammonium sulfate). The precipitated protein can then be separated from the supernatant by centrifugation, and resuspended in a solvent (e.g., phosphate buffered saline [PBS]). The suspended protein can be dialyzed to remove the dissolved salts. Additionally, the dialyzed protein can be heated to denature other proteins, and the denatured proteins can be removed by centrifugation. Optionally, the purified recombinant resilins can be coacervated.

In various embodiments, methods of purifying the secreted recombinant proteins from the fermentation can include various centrifugation steps in conjunction with solubilizing protein in a whole cell broth or cell pellet with known chaotropes such as urea or guanidine thiocyanate.

In some embodiments, the methods provided herein further comprise the step of cross-linking the recombinant resilins to obtain the recombinant resilin compositions provided herein (step 1005 in FIG. 2). Methods for cross-linking proteins are known in the art. In some embodiments, cross-linking is achieved via enzymatic cross-linking (e.g., using horseradish peroxidase). In other embodiments, cross-linking is achieved via photochemical cross-linking (see, for example, Elvin C M, Carr A G, Huson M G, Maxwell J M, Pearson R D, Vuocolo T, Liyou N E, Wong D C C, Merritt D J, Dixon N E. Nature 2005, 437, 999-1002; Whittaker J L, Dutta N K, Elvin C M, Choudhury N R. Journal of Materials Chemistry B 2015, 3, 6576-79; Degtyar E, Mlynarczyk B, Fratzl P, Harrington M J. Polymer 2015, 69, 255-63). In some embodiments, cross-linking is achieved via chemical cross-linking (see, for example, Renner J N, Cherry K M, Su R S C, Liu J C. Biomacromolecules 2012, 13, 3678-85; Charanti, M B, Ifkovits, J L, Burdick, J A, Linhardt J G, Kiick, K L. Soft Matter 2009, 5, 3412-16; Li L Q, Tong Z X, Jia X Q, Kiick K L. Soft Matter 2013, 9, 665-73; Li L, Mahara A, Tong Z, Levenson E A, McGann C L, Jia X, Yamaoka T, Kiick K L. Advanced Healthcare Materials 2016, 5, 266-75). In some embodiments, cross-linking is achieved via tyrosine residues. In other embodiments, cross linking is achieved via lysine residues. In some embodiments, cross linking is achieved via cysteine residues. In some embodiments, cross-linking employs transglutaminase (see, for example, Kim Y, Gill E E, Liu J C. Enzymatic Cross-Linking of Resilin-Based Proteins for Vascular Tissue Engineering Applications. Biomacromolecules. 17(8):2530-9). In some embodiments, cross-linking employs poly(ethylene glycol) (PEG) (McGann C L, Levenson E A, Kiick K L. Macromol. Chem. Phys. 2013, 214, 203-13; McGann C L, Akins R E, Kiick K L. Resilin-PEG Hybrid Hydrogels Yield Degradable Elastomeric Scaffolds with Heterogeneous Microstructure. Biomacromolecules. 2016; 17(1): 128-40). In some embodiments, cross-linking occurs in vessels or molds such that the recombinant resilin compositions obtained have specific shapes or forms.

EXAMPLES

Example 1: Generation of *Pichia pastoris* Recombinant Host Cells that Secrete Recombinant Resilin

*Pichia pastoris* recombinant host cells that secrete recombinant resilin were generated by transforming a HIS+ derivative of GS115 (NRRL Y15851) *Pichia pastoris* (*Komagataella phaffii*) with vectors comprising secreted resilin coding sequences.

Figure 3:
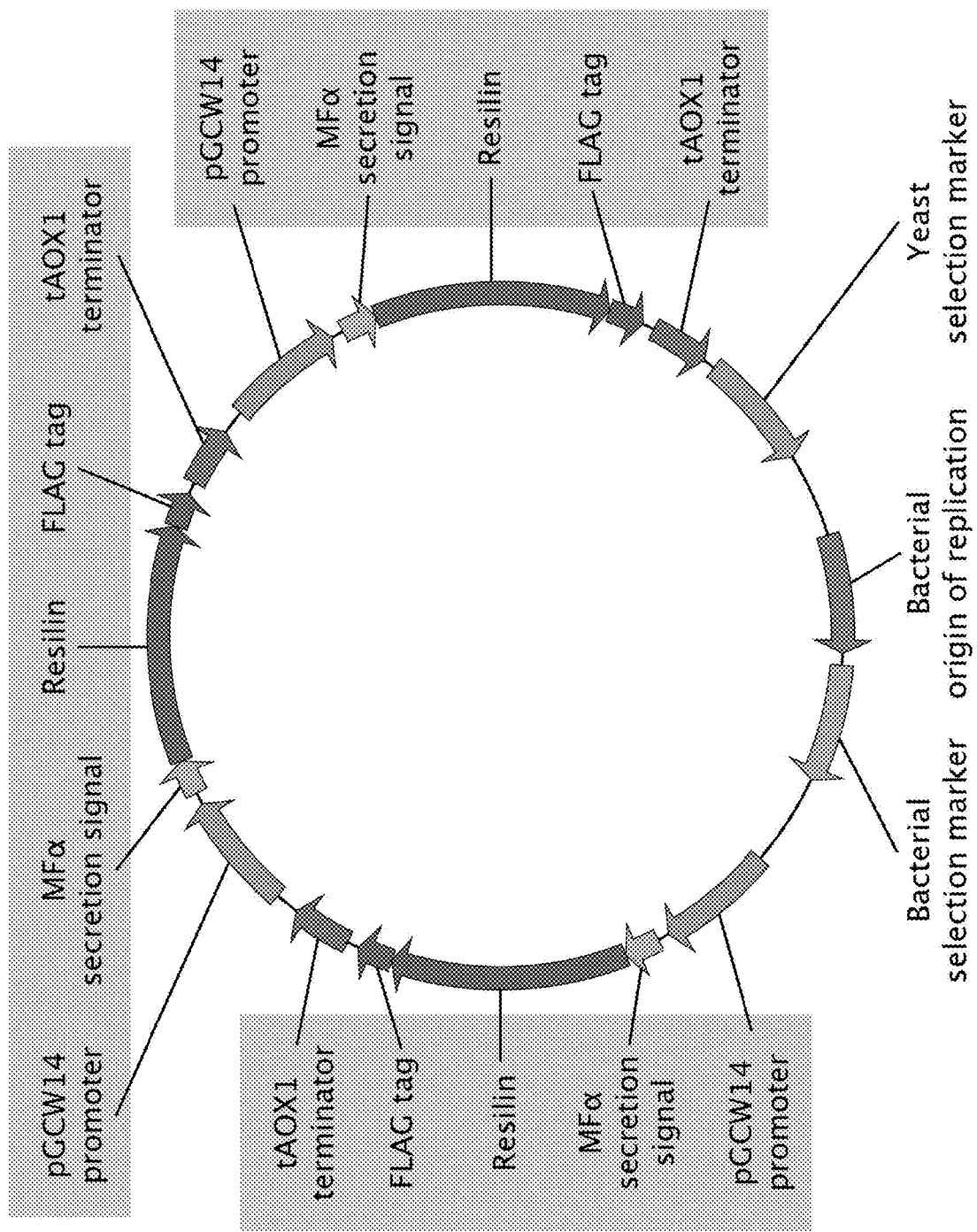
FIG. 3 is an illustrative map of a vector that comprises 3 secreted resilin coding sequences.

The vectors each comprised 3 resilin coding sequences fused in frame to an N-terminal secretion signal (alpha mating factor leader and pro sequence), and in some instances a C-terminal 3xFLAG tag (SEQ ID NO: 45) (see FIG. 3). Each of the secreted resilin coding sequences was flanked by a promoter (pGCW14) and a terminator (tAOX1 pA signal). The vectors further comprised a targeting region that can direct integration of the 3 secreted resilin coding sequences to the HSP82 locus of the *Pichia pastoris* genome, dominant resistance markers for selection of bacterial and yeast transformants, as well as a bacterial origin of replication.

The resilin coding sequences were obtained from scientific literature and from searching public sequence databases. The nucleotide sequences were translated into amino acid sequences and then codon-optimized. Both full length and truncated resilin sequences were chosen. Selected secreted resilin coding sequences are listed in Table 1.

TABLE 1

Exemplary full-length and truncated resilin amino acid sequences and recombinant host strains

| Species | Type | Short Name | Amino Acid SEQ ID NO: | With FLAG tag | | Without FLAG tag | |
| --- | --- | --- | --- | --- | --- | --- | --- |
| | | | | Plasmid | Strain | Plasmid | Strain |
| *Drosophila sechellia* | Full length | Ds_ACB | 1 | RMp4830 | RMs1209 | RMp4842 | RMs1221 |
| *Drosophila sechellia* | A repeats + Chitin binding domain | Ds_AC | 2 | RMp4831 | RMs1210 | RMp4843 | RMs1222 |

TABLE 1-continued

Exemplary full-length and truncated resilin amino acid sequences and recombinant host strains

| Species | Type | Short Name | Amino Acid SEQ ID NO: | With FLAG tag Plasmid | With FLAG tag Strain | Without FLAG tag Plasmid | Without FLAG tag Strain |
|---|---|---|---|---|---|---|---|
| Drosophila sechellia | A repeats only | Ds_A | 3 | RMp4832 | RMs1211 | RMp4844 | RMs1223 |
| Acromyrmex echinatior | A repeats only | Ae_A | 4 | RMp4833 | RMs1212 | RMp4845 | RMs1224 |
| Aeshna sp. | B repeats only | As_B | 5 | RMp4834 | RMs1213 | RMp4846 | RMs1225 |
| Aeshna sp. | Full length | As_ACB | 6 | RMp4835 | RMs1214 | RMp4847 | RMs1226 |
| Haematobia irritans | A repeats only | Hi_A | 7 | RMp4836 | RMs1215 | RMp4848 | RMs1227 |
| Haematobia irritans | Full length | Hi_ACB | 8 | RMp4837 | RMs1216 | RMp4849 | RMs1228 |
| Ctenocephalides felis | A repeats only | Cf_A | 9 | RMp4838 | RMs1217 | RMp4850 | RMs1229 |
| Ctenocephalides felis | B repeats only | Cf_B | 10 | RMp4839 | RMs1218 | RMp4851 | RMs1230 |
| Bombus terrestris | A repeats only | Bt_A | 11 | RMp4840 | RMs1219 | RMp4852 | RMs1231 |
| Tribolium castaneum | A repeats only | Tc_A | 12 | RMp4841 | RMs1220 | RMp4853 | RMs1232 |

The vectors were transformed into *Pichia pastoris* using electroporation to generate host strains comprising 3 integrated copies of each secreted resilin coding sequence. Transformants were plated on YPD agar plates supplemented with an antibiotic, and incubated for 48 hours at 30° C.

Clones from each final transformation were inoculated into 400 μL of Buffered Glycerol-complex Medium (BMGY) in 96-well blocks, and incubated for 24 hours at 30° C. with agitation at 1,000 rpm. A sample was removed, the recombinant host cells were pelleted via centrifugation, and the supernatant was recovered and run on a SDS-PAGE gel for analysis of resilin content via Coomassie gel and Western blot analysis (for polypeptides comprising the 3×FLAG tag). For FLAG-tagged proteins, the remaining cultures were used to inoculate minimal media cultures in duplicate for ELISA measurements. One duplicate was pelleted and the supernatant was measured directly. The second duplicate was extracted with guanidine thiocyanate and both the intra- and extra-cellular fractions were measured.

Figure 4A:
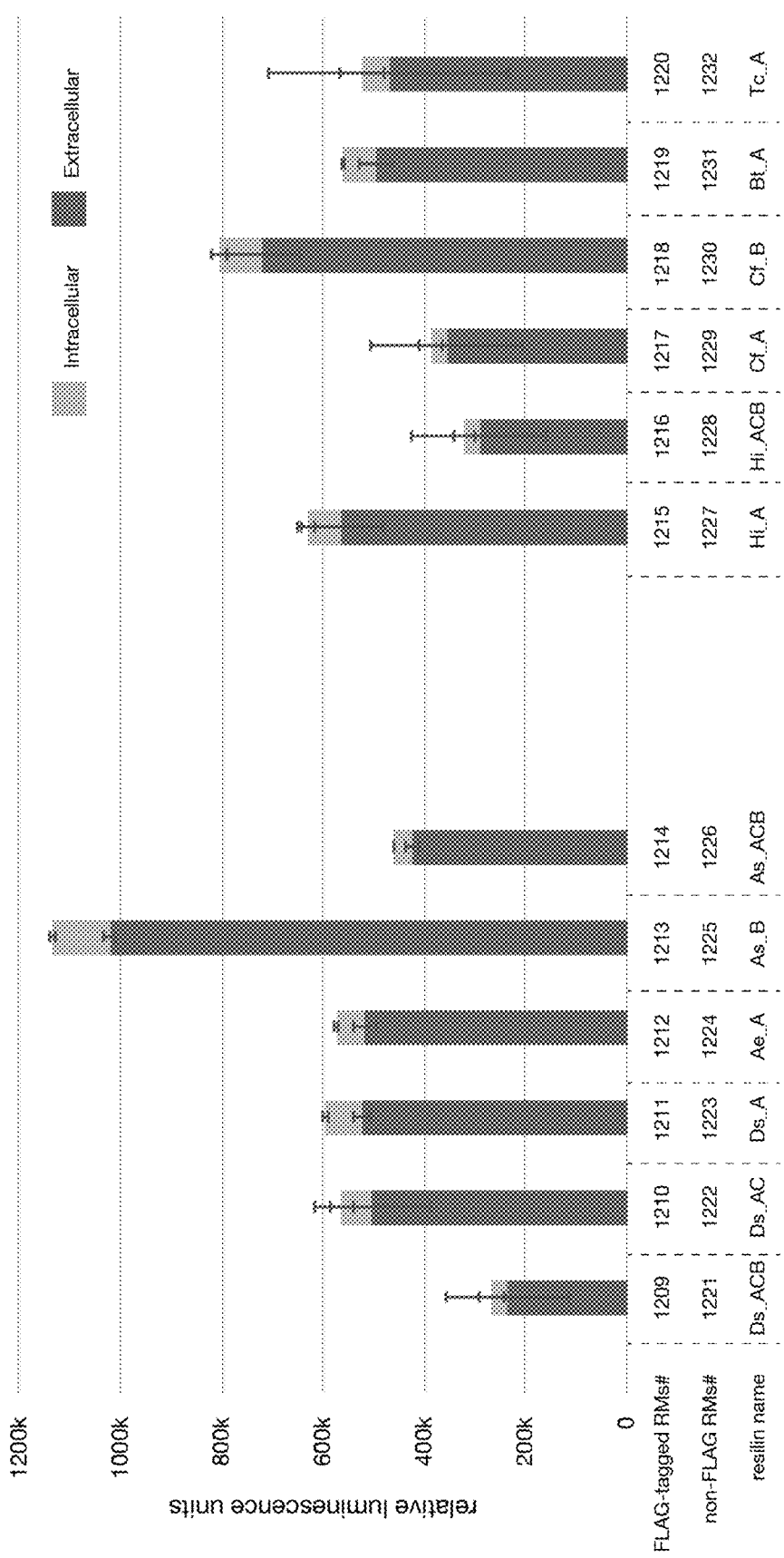
FIG. 4A shows expression and secretion of 3× FLAG-tagged recombinant resilins in *Pichia pastoris* (*Komagataella phaffii*) recombinant host cells as assayed by ELISA.
Figure 4B:
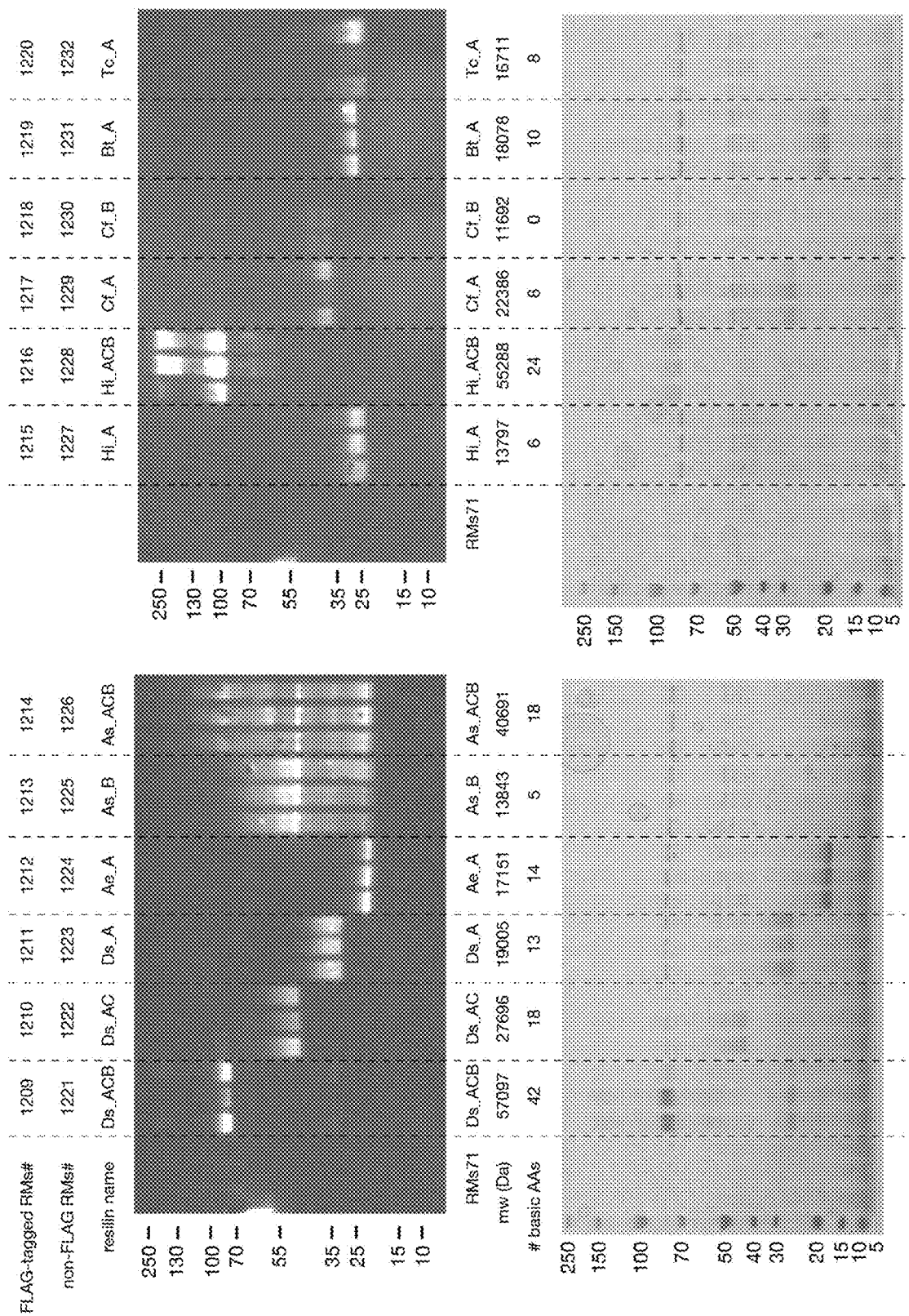
FIG. 4B shows expression of recombinant resilins in *Pichia pastoris* (*Komagataella phaffii*) recombinant host cells as assayed by Western blot (top; 3×FLAG-tagged recombinant resilins), and Coomassie (bottom; untagged recombinant resilins).

As shown in FIG. 4B and FIG. 4C, recombinant resilin from numerous species expressed successfully in the *Pichia pastoris* recombinant host cells. (Note: Some proteins have very few basic residues, and are therefore difficult to detect by Coomassie, though they have a signal on Western.) As shown in FIG. 4A, recombinant host cells secreted up to 90% of the recombinant resilin produced.

Figure 5A:
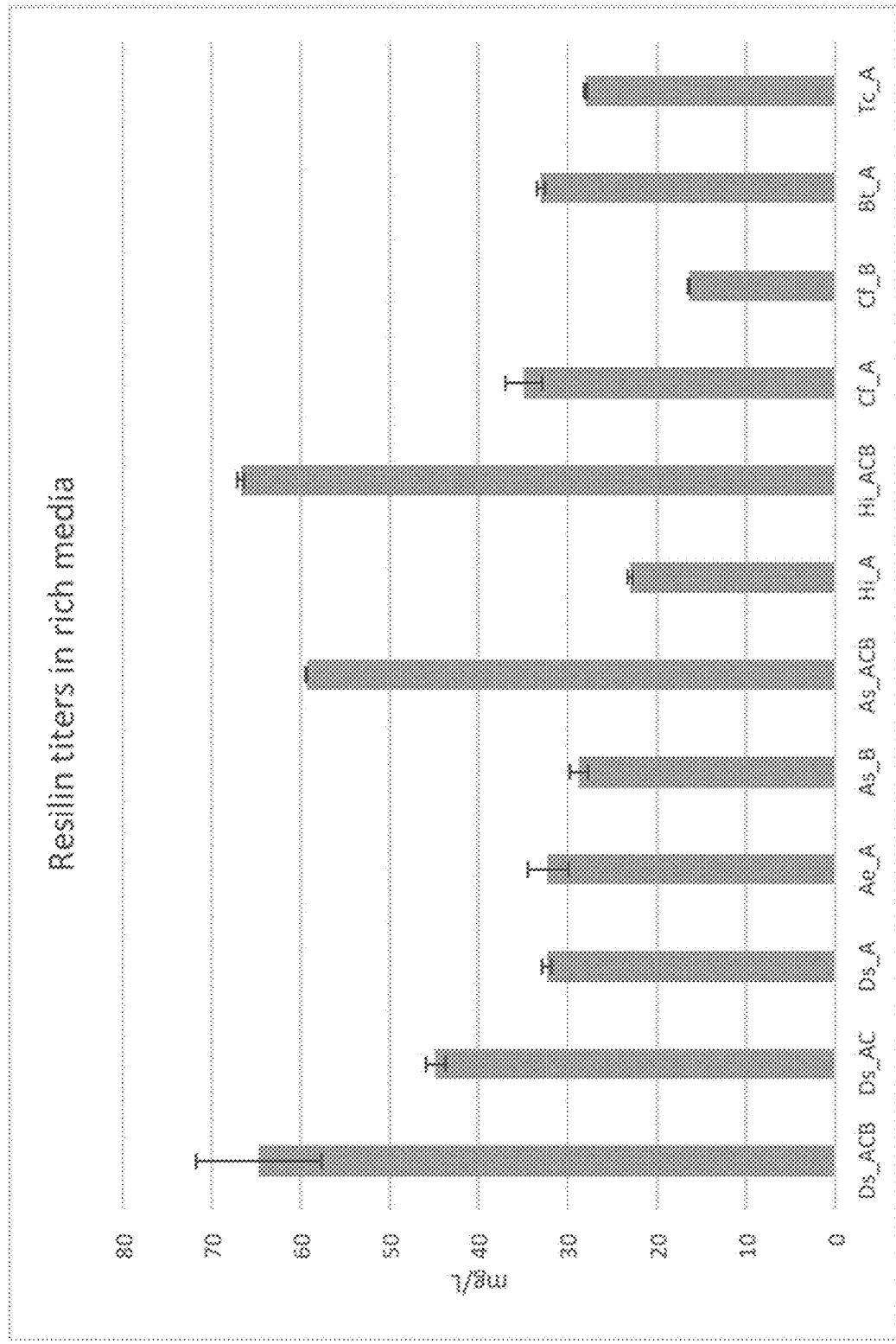
FIG. 5A shows productivities of recombinant host cells producing recombinant resilins in rich media.
Figure 5B:
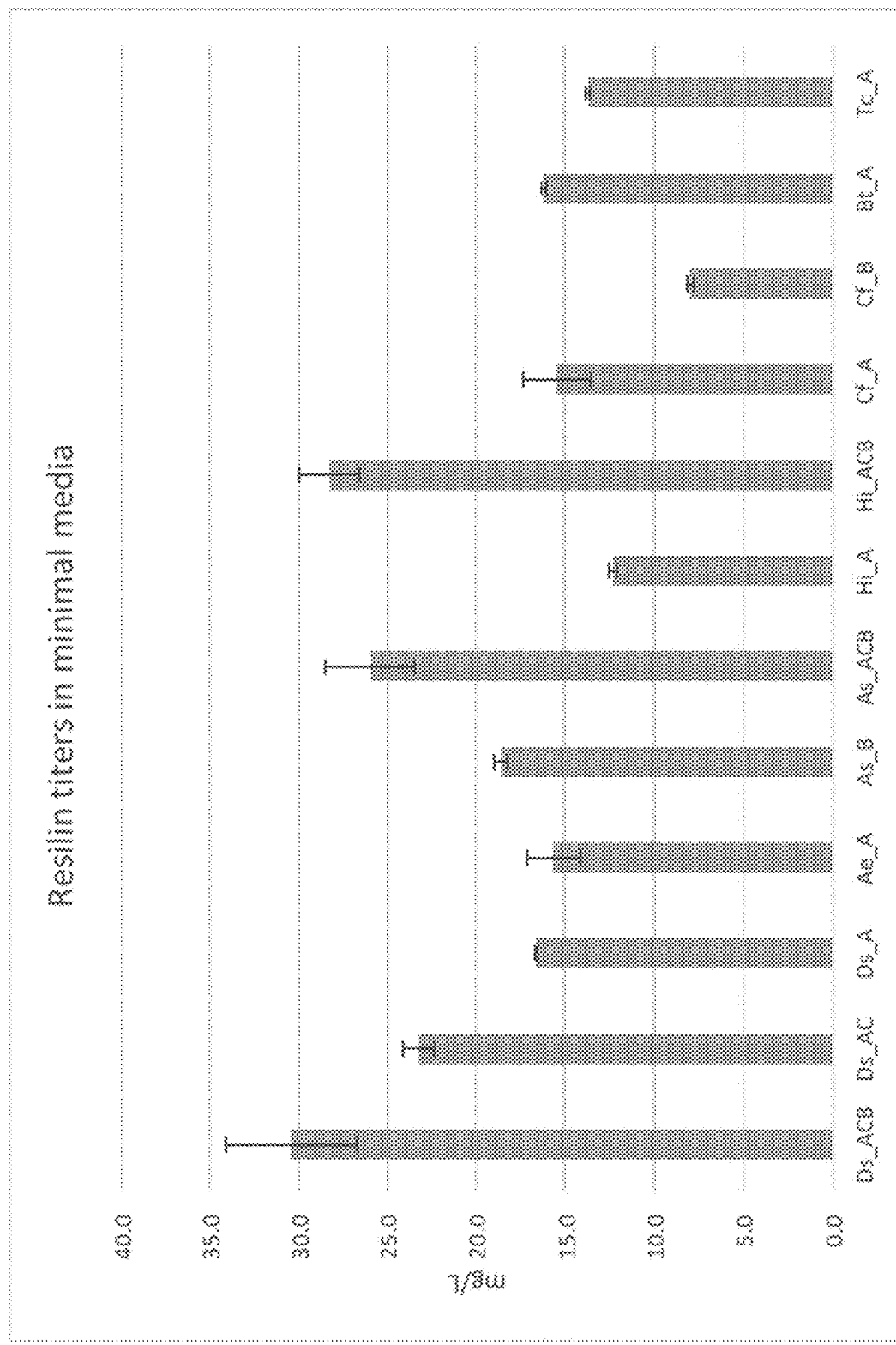
FIG. 5B shows productivities of recombinant host cells producing recombinant resilins in minimal media.

Example 2: Measuring Productivity of *Pichia pastoris* Recombinant Host Cells Expressing and Secreting Recombinant Resilin To measure productivity, 3 clones of each recombinant host cell were inoculated into 400 μL of BMGY in a 96-well square-well block, and incubated for 48 hours at 30° C. with agitation at 1,000 rpm. Following the 48-hour incubation, 4 μL of each culture was used to inoculate 400 μL of minimal media in a 96-well square-well block, which was then incubated for 48 hours 30° C. with agitation at 1,000 rpm. 400 uL of 5M guanidine thiocyanate was added to the cultures, and the mixtures were pelleted by centrifugation. The supernatants were saved whereas the pellets were resuspended in 800 μL of 2.5M guanidine thiocyanate. The resuspended cells were physically lysed using beads, the lysed cell mixture was pelleted by centrifugation, and the supernatant was saved. The concentration of resilin in each fraction was determined by direct enzyme-linked immunosorbent assay (ELISA) analysis quantifying the 3×FLAG epitope (FIG. 5A and FIG. 5B).

Example 3: Purification of Recombinant Resilin

The non-FLAG-tagged Ds_ACB and Ae_A polypeptides were chosen for purification and cross-linking. Strains RMs1221 (expressing Ds_ACB) and RMs1224 (expressing Ae_A) were grown in 500 mL of BMGY in flasks for 48 hours at 30° C. with agitation at 300 rpm.

The protocol for purification was adapted from Lyons et al. (2007). Cells were pelleted by centrifugation, and supernatants were collected. Proteins were precipitated by addition of ammonium sulfate. The precipitated proteins were resuspended in a small volume of phosphate buffered saline (PBS), and the resuspended samples were dialyzed against PBS to remove salts. The dialyzed samples were then heated to denature native proteins, and denatured proteins were removed by centrifugation. The retained supernatants contained the purified resilin polypeptides. Optionally, the retained supernatants were chilled, which caused coacervation, resulting in a concentrated lower phase and dilute upper phase.

Figure 6:
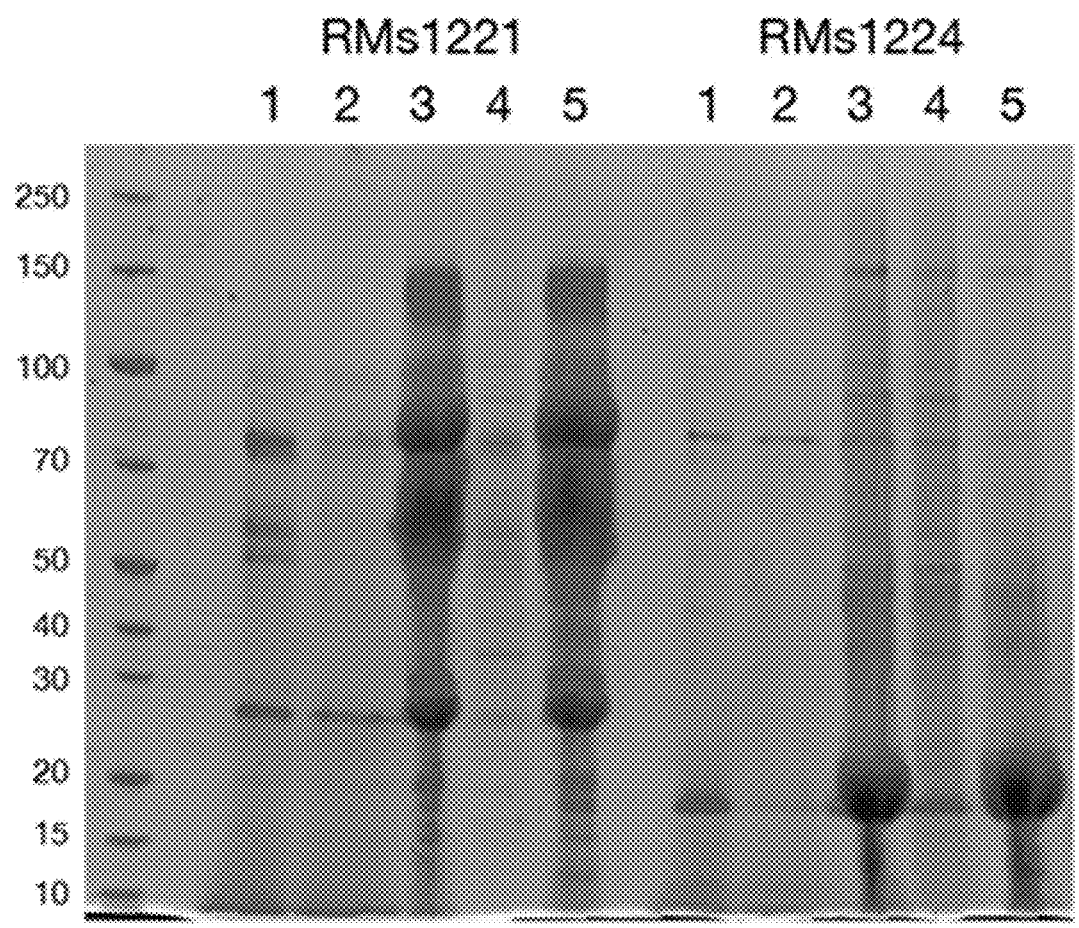
FIG. 6 shows purification of 2 secreted recombinant resilins from 500 mL BMGY flask growth. For each sample, Lane 1 is the original supernatant; Lane 2 is the supernatant after precipitation; Lane 3 is the dialyzed precipitate; Lane 4 is the heat-denatured proteins; and Lane 5 is the final purified recombinant resilin.

As shown in FIG. 6, Ae_A was obtained in relatively pure form whereas Ds_ACB produced 3 bands at 70 kDa, 50 kDa, and 25 kDa.

Example 4: Cross-Linking of Purified, Secreted, Recombinant Resilin

Concentrated Ds_ACB resilin was cross-linked via one of two methods: photo cross-linking (adapted from Elvin et al. 2005) and enzymatic cross-linking (adapted from Qin et al. 2009).

For photo cross-linking, resilin protein was mixed with ammonium persulfate and tris (bipyridine) ruthenium (II)

([Ru(bpy)3]2+). The mixture was exposed to bright white light, after which the mixture formed a rubbery solid.

For enzymatic cross-linking, resilin protein was mixed with horseradish peroxidase (HRP) and hydrogen peroxide. The mixture was incubated at 37° C., after which the mixture formed a rubbery solid.

Example 5: Production of a Block of Recombinant Resilin

Strain RMs1221 (expressing the Ds_ACB resilin) was run in two 2 L fermentation tanks to produce a larger quantity of protein.

The strain was grown in a minimal basal salt media with 15 g/L of glucose as a starting feedstock and 1 g/L L81 antifoam, in a stirred fermentation vessel controlled at 30° C., with 1 VVM of air flow and minimum agitation of 700 rpm. The pH of the fermentation was controlled at 5 with on-demand addition of ammonium hydroxide. Once batch glucose was depleted, glucose was added via a programmed feed recipe that was designed to maintain the oxygen uptake rate 120 mmole/L/h, the temperature was decreased to 25° C., and dissolved oxygen was maintained at 20%. The fermentation was harvested after 70 hours, at about 700-800 OD of cell density.

Figure 7:
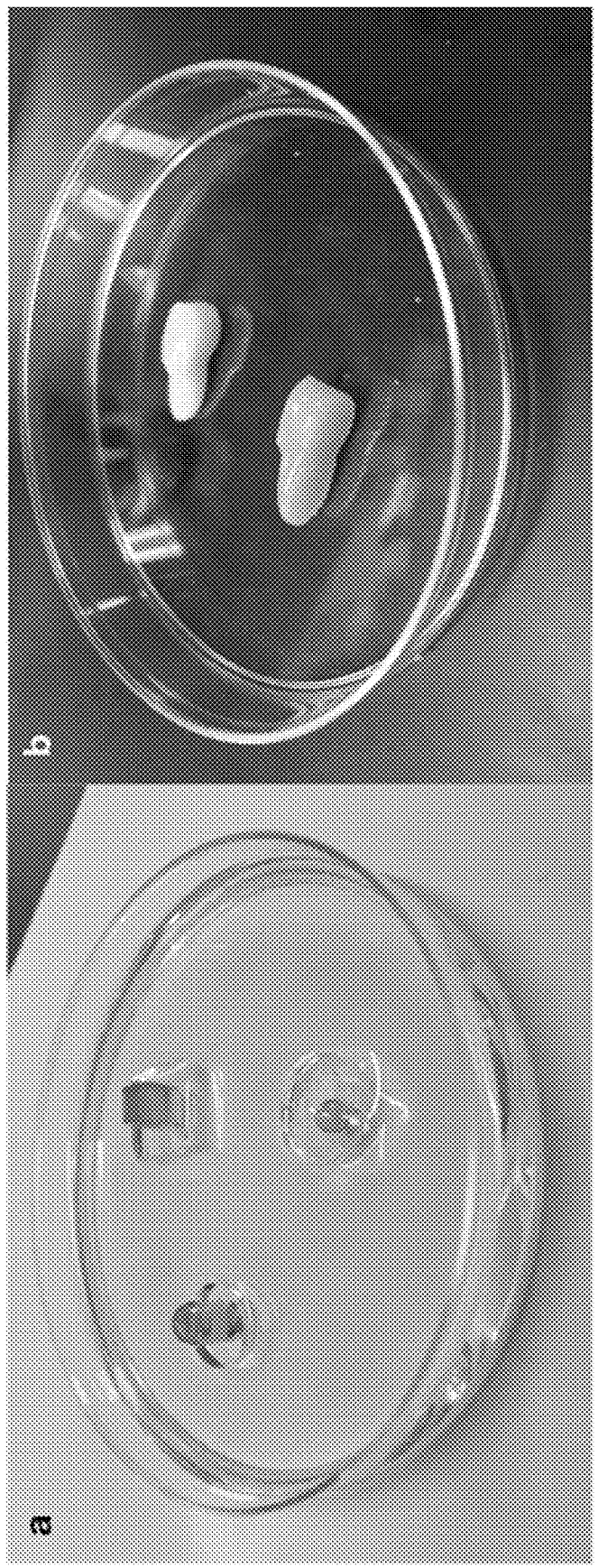
FIG. 7 shows photographs of proteinaceous block copolymers comprising cross-linked purified recombinant resilins in various shapes and forms.

The protein was purified as described in Example 3, and combined with reagents for enzymatic cross-linking as described in Example 4. The cross-linking mixture was filled into small cylindrical, rectangular, spherical, and shoe-shaped molds, and finally incubated at 37° C. Resulting recombinant resilin solids are shown in FIG. 7.

Example 6: Material Testing of Resilin Solids

Figure 8:
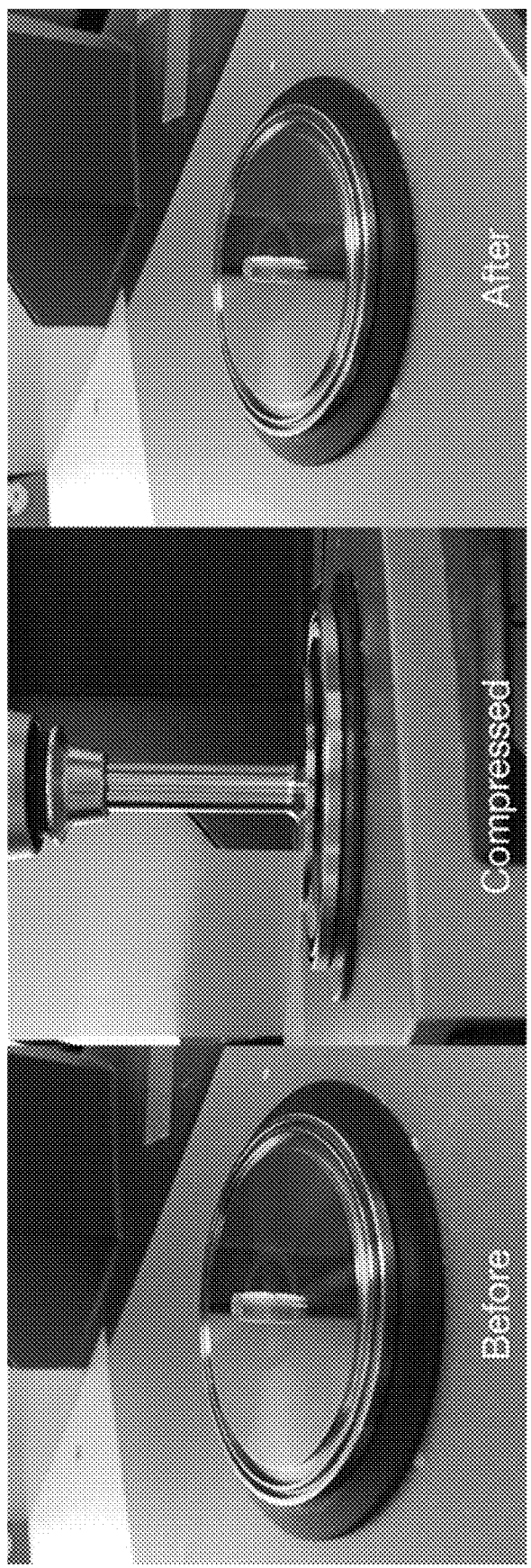
FIG. 8 shows photographs of the compression of a proteinaceous block co-polymer comprising cross-linked recombinant resilin.

A resilin cylinder produced as described in Example 5 was subjected to a compression test using a rheometer. The recombinant resilin cylinder could be compressed from an initial height of 7.3 mm (avg width 5.4 mm) to less than 0.66 mm without any breakage. As shown in FIG. 8, the cylinder returned to a height of 6.7 mm (avg width 5.6 mm) upon release of the compressive load.

Example 7: Methods for Recovering Full-Length Recombinant Resilin from Whole Cell Broth Various recovery and separation techniques were used to purify Ds_ACB (SEQ ID NO: 1) that was produced in strains with a 3× FLAG tag (RMs1209) and without a 3× FLAG tag (RMs1221) according to Example 1 above.

A first set of samples was prepared by centrifuging a whole cell broth to produce a first pellet of cells and a first supernatant, and extracting the first supernatant to produce a clear cell broth. The first supernatant was then precipitated using ammonium sulfate and centrifuged to produce a second pellet and second supernatant which was discarded. The second pellet was then re-suspended in PBS for dialysis. The dialyzed solution was then subject to high temperature to denature proteins other than Ds_ACB, which is stable at high temperatures. The denatured proteins were removed by centrifuging the dialyzed and denatured solution to produce a third pellet and third supernatant. The third supernatant was retained from the denatured solution, then coacervated by chilling the third supernatant to induce a phase separation into a dense lower layer containing the Ds_ACB and an upper layer. These samples are referred to in Table 2 below and elsewhere herein as the "CCB" samples. In some CCB samples, multiple coacervations were performed by retaining the lower layer and incubating the lower layer at a lower temperature to induce further phase separation. These CCB samples are respectively referred to in Table 2 below and elsewhere herein as the "first coacervation" and "second coacervation" samples.

A second set of samples was prepared by centrifuging a whole cell broth to produce a first pellet of cells and protein proximal to the cells (e.g. adherent to the cells, on the surface of the cells) and/or insoluble protein (e.g. protein aggregates) and first supernatant, then discarding the first supernatant to obtain the first pellet. The first pellet was re-suspended in guanidine thiocyanate to solubilize Ds_ACB. The re-suspension was centrifuged again produce a second pellet and a second supernatant. The second supernatant was then dialyzed against PBS and subject to high temperature in order to denature proteins other than Ds_ACB and centrifuged to produce a third pellet and third supernatant. The third supernatant was subject to coacervation by chilling to yield phase separation into a dense lower layer containing Ds_ACB and an upper layer. These samples are referred to in Table 2 below and elsewhere herein as the "gel layer" samples. In some gel layer samples, multiple coacervations were performed by retaining the lower layer and incubating the lower layer at a lower temperature to induce further phase separation. These gel layer samples are referred to in Table 2 below and elsewhere herein as the "first coacervation" and "second coacervation" samples.

A third set of samples was prepared by centrifuging a whole cell broth to produce a pellet and supernatant, then discarding the supernatant to obtain a pellet of cells and protein proximal to the cells (e.g. adherent to the cells, on the surface of the cells) and/or insoluble protein (e.g. protein aggregates). The pellet of cells was re-suspended in guanidine thiocyanate to solubilize the protein that was proximal to the cells. The re-suspension was centrifuged again produce a second pellet of cells and a second supernatant. The second supernatant was then precipitated with ammonium sulfate and centrifuged to produce a third pellet and third supernatant. The third pellet was suspended in guanidine thiocyanate, then dialyzed against PBS and subject to high temperature to denature proteins other than Ds_ACB and centrifuged to produce a fourth supernatant and fourth pellet. The fourth supernatant was then subject to coacervation by chilling to yield phase separation. These samples are referred to in Table 2 below and elsewhere herein as the "gel layer precipitated" samples.

A single sample was produced by adding urea to a whole cell broth to solubilize the protein, then centrifuging the whole cell broth to produce a first pellet and first supernatant. The first supernatant was then precipitated using ammonium sulfate and centrifuged to produce a second pellet and second supernatant. The second supernatant was discarded and the second pellet was then re-suspended in guanidine thiocyanate and dialyzed against PBS, then subject to high temperature in order to denature proteins other than Ds_ACB and centrifuged again to produce a third pellet and a third supernatant. The third supernatant was then coacervated by chilling the third supernatant to induce a phase separation into a dense lower layer containing Ds_ACB and an upper layer. This sample is referred to in Table 2 below and elsewhere herein as the "Urea WCBE" sample.

Another single sample was prepared by centrifuging a whole cell broth to produce a first pellet and first supernatant, then discarding the first supernatant to obtain a first pellet of cells and protein proximal to the cells (e.g. adherent to the cells, on the surface of the cells) and/or insoluble protein (e.g. protein aggregates). The first pellet of cells was re-suspended in guanidine thiocyanate to solubilize the protein. The re-suspension was centrifuged again to produce a second pellet of cells and a second supernatant. The second supernatant was then dialyzed against PBS and then centrifuged to produce a heavy phase of protein, a light phase of supernatant and a film separating the heavy phase from the light phase. The heavy phase of protein was then isolated by discarding the light phase and the film. This sample is referred to in Table 2 below and elsewhere herein as the "Dense layer" sample.

Figure 9:
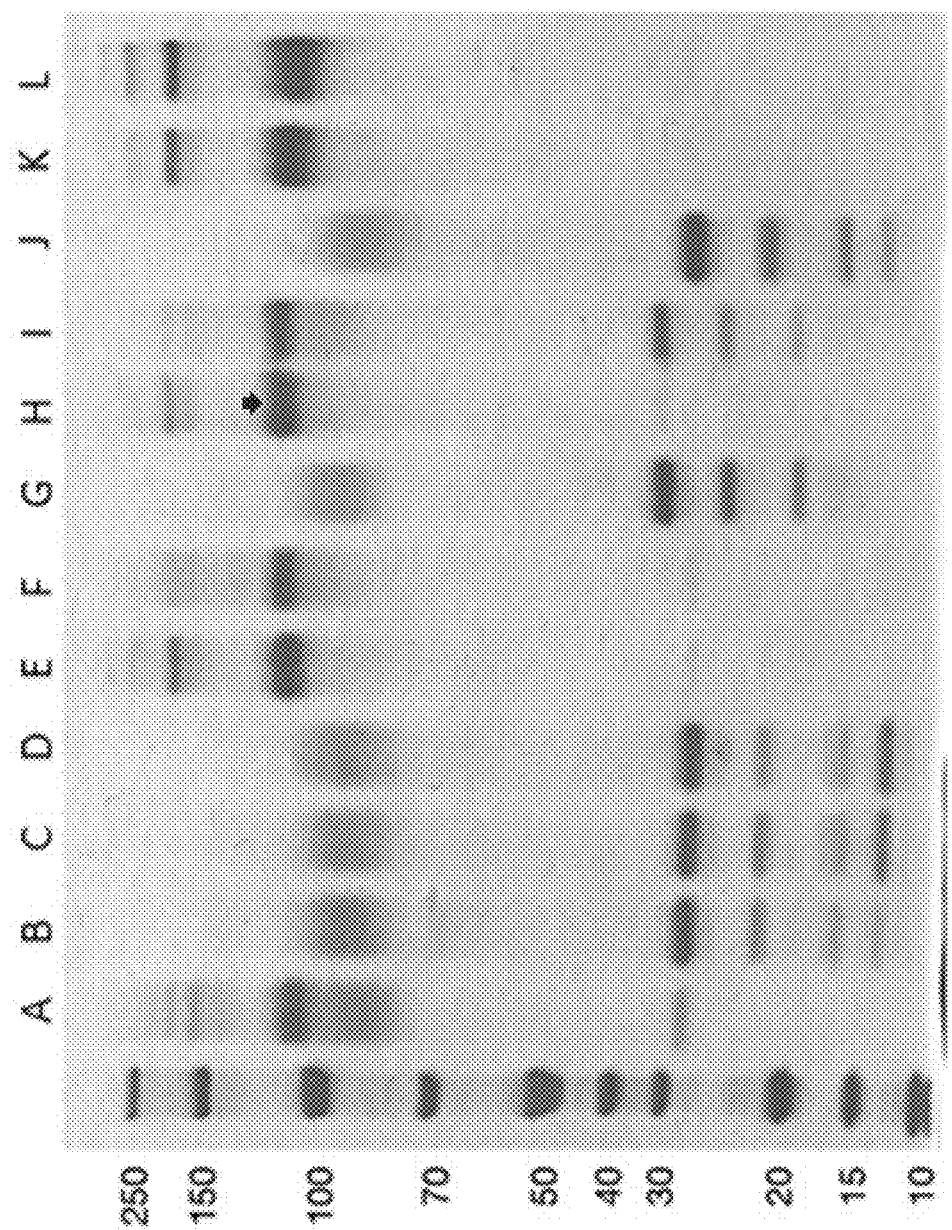
FIG. 9 is an image of a gel showing the resulting bands from recombinant resilin compositions purified by selected methods described herein.

Table 2 (below) lists the various combinations of strains and recovery techniques along with the relative amount of degradation seen in the gel pictured at FIG. 9. As shown in FIG. 9, samples E, F, G, K and L showed bands at approximately 110 kDa and minimal or faint bands at lower molecular weights (labeled in Table 2 as "Minimal"). Samples A, B, C, D, G, I and J had degradation products corresponding to bands at approximately 90, 30, 22, 17 and 12 kDa (labelled in Table 2 as "Substantial"). Among these, samples A and I also showed bands at approximately 110 kDa indicating the presence of full-length resilin. Accordingly, the "Gel layer" samples produced full-length resilin while the CCB samples produced degradation products sometimes in addition to full-length resilin (e.g. sample A) or without full-length resilin (e.g. samples C and D). The Urea WCBE sample only produced degradation products. CCB/gel layer precipitated indicates the combination of isolated material from both the CCB purification and the gel layer purification methods.

sequences that are later cleaved. The first sequence (italics), is an alpha mating factor precursor protein signal sequence (SEQ ID NO: 46) that is cleaved twice after transcription by a signal peptidase followed by cleavage with Kex2. The second sequence (bold) is an EAEA repeat that is cleaved by Ste13 (SEQ ID NO: 47). The third sequence (lower case) corresponds to *Drosophila sechellia* full-length resilin (SEQ ID NO 1). The fourth sequence (bold and italicized) corresponds to a linker sequence (SEQ ID NO: 46). The fifth sequence (underlined) corresponds to the 3× FLAG tag (SEQ ID NO: 45).

Edman sequencing confirmed that the N-terminus of the protein sequences at the approximately 110 kDa band corresponded to the full-length length *Drosophila sechellia* resilin sequence. Specifically, the N-terminus sequencing showed that the N-terminus either corresponded to "EAEA" or "GRPE", respectively the full-length *Drosophila sechellia* resilin sequence with or without the EAEA repeat.

Example 8: Quantifying the Stability of Crosslinked Resilin

Resilin samples generated by the methods described in Example 7 with varying levels of degradation products and full-length resilin were subject to enzymatic cross-linking as described above with respect to Example 4. The stability of the cross-linked samples was assessed over time by determining the duration each cross-linked samples remained a solid through daily observation. Table 3 shows the time as a solid for each cross-linked sample. As shown in Table 3,

TABLE 2

Samples from recovery methods yielding full-length resilin and degradation products

| Sample | Strain | FLAG | Description | Coacervation | 110 kDa band? | Degradation |
|---|---|---|---|---|---|---|
| A | RMs1221 | − | CCB | First | Yes | Substantial |
| B | RMs1221 | − | Urea WCBE | None | No | Substantial |
| C | RMs1221 | − | CCB | First | No | Substantial |
| D | RMs1221 | − | CCB | Second | No | Substantial |
| E | RMs1221 | − | Gel layer | First | Yes | Minimal |
| F | RMs1221 | − | Gel layer | Second | Yes | Minimal |
| G | RMs1209 | + | CCB | First | No | Substantial |
| H | RMs1209 | + | Gel layer precipitated | First | Yes | Minimal |
| I | RMs1209 | + | CCB/gel layer precipitated | First | Yes | Substantial |
| J | RMs1221 | − | CCB | First | No | Substantial |
| K | RMs1221 | − | Gel layer | First | Yes | Minimal |
| L | RMs1221 | − | Dense layer | None | Yes | Minimal |

To verify that the 110 kDa bands shown in samples A, I, E, F, G, K and L corresponded to the full-length resilin (SEQ ID NO: 1), the 110 kDa band in sample H (indicated in FIG. 9 with an arrow) was excised and sent for N-terminus sequencing by Edman degradation. Edman degradation is a cyclic procedure where amino acid residues are cleaved off one at a time and identified by chromatography. There are 3 steps in the cyclic procedure. In step 1 the PITC reagent is coupled to the N-terminal amino group under alkaline conditions. In step 2 the N-terminal residue is cleaved in acidic media. In step 3, the PITC coupled residue is transferred to a flask, converted to a PTH-residue and identified by HPLC chromatography. The next cycle is then started for identification of the next N-terminal residue. Edman degradation analysis was performed on a Shimadazu PPSQ-33 sequencer and a PVDF membrane.

FIG. 10 shows the full-length *Drosophila sechellia* resilin sequence (Ds_ACB) that is expressed along with signal samples comprising full-length resilin had a longer duration of stability than the samples that did not comprise full-length resilin.

TABLE 3

Stability of cross-linked resilin

| Sample | 110 kDa band? | Degradation | Time as solid |
|---|---|---|---|
| A | Yes | Substantial | 13 days |
| B | No | Substantial | 8 days |
| C | No | Substantial | 6 days |
| D | No | Substantial | 6 days |
| E | Yes | Minimal | N/A |
| F | Yes | Minimal | 27 days |
| G | No | Substantial | 8 days |
| H | Yes | Minimal | 15 days |
| I | Yes | Substantial | 15 days |
| J | No | Substantial | 6 days |

TABLE 3-continued

Stability of cross-linked resilin

| Sample | 110 kDa band? | Degradation | Time as solid |
|---|---|---|---|
| K | Yes | Minimal | 13 days |
| L | Yes | Minimal | 13 days |

ADDITIONAL CONSIDERATIONS

The foregoing description of the embodiments of the disclosure has been presented for the purpose of illustration; it is not intended to be exhaustive or to limit the claims to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the invention, which is set forth in the claims.

SEQUENCE LISTING

| SEQ ID NO: | Species | Sequence |
|---|---|---|
| 1 | Drosophila sechellia | RPEPPVNSYLPPSDSYGAPGQSGAGGRPSDTYGAPGGGNGGRPSDSYGAPG QGQGQGQGQGGYGGKPSDSYGAPGGGNGNGGRPSSSYGAPGGGNGGRPSDT YGAPGGGNGGRPSDTYGAPGGGGNGNGGRPSSSYGAPGQGQGNGNGGRPSS SYGAPGGGNGGRPSDTYGAPGGGNGGRPSDTYGAPGGGNNGGRPSSSYGAP GGGNGGRPSDTYGAPGGGNGNGSGGRPSSSYGAPAQGQGGFGGRPSDSYGA PGQNQKPSDSYGAPGSGNGSAGRPSSSYGAPGSGPGGRPSDSYGPPASGSG AGGAGGSGPGGADYDNDEPAKYEFNYQVEDAPSGLSFGHSEMRDGDFTTGQ YNVLLPDGRKQIVEYEADQQGYRPQIRYEGDANDGSGPSGPSGPGGPGGQN LGADGYSSGRPGNGNGNGNGGYSSGRPGGQDLGPSGYSGGRPGGQDLGAGG YSNVKPGGQDLGPGGYSGGRPGGQDLGRDGYSGGRPGGQDLGAGAYSNGRP GGNGNGGSDGGRVIIGGRVIGGQDGGDQGYSGGRPGGQDLGRDGYSSGRPG GRPGGNGQDSQDGQGYSSGRPGQGGRNGFGPGGQNGDNDGSGYRY |
| 2 | Drosophila sechellia | RPEPPVNSYLPPSDSYGAPGQSGAGGRPSDTYGAPGGGNGGRPSDSYGAPG QGQGQGQGQGGYGGKPSDSYGAPGGGNGNGGRPSSSYGAPGGGNGGRPSDT YGAPGGGNGGRPSDTYGAPGGGGNGNGGRPSSSYGAPGQGQGNGNGGRPSS SYGAPGGGNGGRPSDTYGAPGGGNGGRPSDTYGAPGGGNNGGRPSSSYGAP GGGNGGRPSDTYGAPGGGNGNGSGGRPSSSYGAPAQGQGGFGGRPSDSYGA PGQNQKPSDSYGAPGSGNGSAGRPSSSYGAPGSGPGGRPSDSYGPPASG |
| 3 | Drosophila sechellia | GKPSDSYGAPGGGNGNGGRPSSSYGAPGGGNGGRPSDTYGAPGGGNGGRPS DTYGAPGGGNGNGGRPSSSYGAPGQGQGNGNGGRPSSSYGAPGGGNGGRP SDTYGAPGGGNGGRPSDTYGAPGGGNNGGRPSSSYGAPGGGNGGRPSDTYG APGGGNGNGSGGRPSSSYGAPAQGQGGFGGRPSDSYGAPGQNQKPSDSYGA PGSGNGS |
| 4 | Acromyrmex echinatior | FGENRGNGGKPSTSYGVPDSNGNNRGGFGNGGSEGRPSTSYGLPDASRNNG NGFGNVGNEDKPSTNYGIPANGNKVSGFGNVGSEGRPSTSYGVPGANGNQG FGSGGIGGRPSTSYGVPGVNGNNGGGFENVGRPSTSYGTPDARGNNGGSFR NGDIGGRPSTNYGIPGANGNHG |
| 5 | Aeshna | APSRGGGHGGGSISSSYGAPSKGSGGFGGGSISSSYGAPSKGSVGGGVSSS YGAPAIGGGSFGGGSFGGGSFGGGSFGGGAPSSSYGAPSSSYSAPSSSYGA PSKGSGGFGSSGGFSSFSSAPSSSYGAPSASYSTPSSSYGAPSSGGFGAGG GFSSG |
| 6 | Aeshna | EPPVGGSQSYLPPSSSYGAPSAGTGFGHGGGSPSQSYGAPSFGGGSVGGGS HFGGGSHSGGGGGGYPSQSYGAPSRPSGSSFQAFGGAPSSSYGAPSSQYGA PSGGGGSYAIQGGSFSSGGSRAPSQAYGAPSNNAGLSHQSQSFGGGLSSSY GAPSAGFGGQSHGGGYSQGGNGGGHGGSSGGGYSYQSFGGGNGGGHGGSRP SSSYGAPSSSYGAPSGGKGVSGGFVSQPSGSYGAPSQSYGAPSRGGGHGGG SISSSYGAPSKGSGGFGGGSISSSYGAPSKGSVGGGVSSSYGAPAIGGGSF GGGSFGGGSFGGGSFGGGAPSSSYGAPSSSYSAPSSSYGAPSKGSGGFGSS GGFSSFSSAPSSSYGAPSASYSTPSSSYGAPSSGGFGAGGGFSSGGYSGGG GGYSSGGSGGFGGHGGSGGAGGYSGGGGYSGGGSGGGQKYDSNGGYVYS |
| 7 | Haematobia irritans | AGGGNGGGGTGGTPSSSYGAPSNGGGSNGNGFGSPSSSYGAPGSGGSNGNG GGRPSLSYGAPGSGGSNGNGGGRPSSSYGAPGAGGSNGNGGGRPSSSYGAP GAGGSNGNGGGRPSSSYGAPGAGGSNGNGGGRPSSSYGAPGAGGSNGNGGS RPSSTYGAP |
| 8 | Haematobia irritans | RPEPPVNSYLPPPLNNYGAPGAGGGSSDGSPLAPSDAYGAPDLGGGSGGSG QGPSSSYGAPGLGGGNGGAPSSSYGAPGLGGGNGGSRRPSSSYGAPGAGGG NGGGGTGGTPSSSYGAPSNGGGSNGNGFGSPSSSYGAPGSGGSNGNGGGRP SLSYGAPGSGGSNGNGGGRPSSSYGAPGAGGSNGNGGGRPSSSYGAPGAGG SNGNGGGRPSSSYGAPGAGGSNGNGGGRPSSSYGAPGAGGSNGNGGSRPSS TYGAPGAGGSNGNGCGNKPSSSYGAPSAGSNGNGGSEQGSSGSPSDSYGPP ASGTGRGRNGGGGGAGGGRRGQPNQEYLPPNQGDNGNNGGSGGDDGYDYSQ SGDGGGQGGSGGSGNGGDDGSNIVEYEAGQEGYRPQIRYEGEANEGGQGSG |

| SEQ ID NO: | Species | Sequence |
|---|---|---|
| | | GAGGSDGTDGYEYEQNGGDGGAGGSGGPGTGQDLGENGYSSGRPGGDNGGG GGYSNGNGQGDGGQDLGSNGYSSGAPNGQNGGRRNGGGQNNNGQGYSSGRP NGNGSGGRNGNGGRGNGGGYRNGNGNGGGNGNGSGSGSGNNGYNYDQQGSN GFGAGGQNGENDGSGYRYS |
| 9 | Ctenocephalides felis | ANGNGFEGASNGLSATYGAPNGGGFGGNGNGGAPSSSYGAPGAGNGGNGGG RPSSSYGAPGAGGSGNGFGGRPSSSYGAPGNGNGANGGRGGRPSSRYGAPG NGNGNGNGNGGRPSSSYGAPGSNGNGGRPSSSYGAPGSGNGFGGNGGRPSS SYGAPGANGNGNGGAIGQPSSSYGAPGQNGNGGGLSSTYGAPGAGNGGFGG NGGGLSSTYGAPGSGNGGFGGNGLSSTYGAPGSGNGGFGGNGGGLSSTYGA P |
| 10 | Ctenocephalides felis | PGGAGGAGGYPGGAGGAGGAGGYPGGSAGGAGGYPGGSGSGVGGYPGGSNG GAGGYPGGSNGGAGGYPGGSNGGAGGYPGGSNGGAGGYPGGSNGNGGYSNG GSNGGGAGGYPGGSNGNGGYPGSGSNGGAGGYPGGSNGNGGYPG |
| 11 | Bombus terrestris | FDGQNGIGGGDSGRNGLSNSYGVPGSNGGRNGNGRGNGFGGGGQPSSSYGAP SNGLGGNGGSGAGRPSSSYGAPGGGNGFGGGGQPSSSYGAPSNGLGGNGAGR PSSSYGAPGGGNGFGGGSNGAGKNGFGGAPSNSYGPPENGNGFGGGNGGGS PSGLYGPPGRNGGNGGNGGNGGRPSSSYGTPERNGGRPSGLYGPP |
| 12 | Tribolium castaneum | NGFGGGQNGGRLSSTYGPPGQGGNGFGGGQNGGRPSSTYGPPGQGGNGFGG GQNGGRPSSTYGPPGQGGNGFGGGQNGGRPSSTYGPPGQGGNGFGGGQNGG RPSSTYGPPGQGGNGFGGGQNGGRPSSTYGPPGQGGNGFGGGQNGGKPSST YGPPGQGGNGFGGGQNGGRPSSTYGPPGQG |
| 13 | Tribolium castaneum | RAEPPVNSYLPPSQNGGPSSTYGPPGFQPGTPLGGGGNGGHPPSQGGNGGF GGRHPDSDQRPGTSYLPPGQNGGAGRPGVTYGPPGQGGGQNGGGPSSTYGP PGQGGNGFGGGQNGGRLSSTYGPPGQGGNGFGGGQNGGRPSSTYGPPGQGG NGFGGGQNGGRPSSTYGPPGQGGNGFGGGQNGGRPSSTYGPPGQGGNGFGG GQNGGRPSSTYGPPGQGGNGFGGGQNGGRPSSTYGPPGQGGNGFGGGQNGG KPSSTYGPPGQGGNGFGGGQNGGRPSSTYGPPGQGGNGNGGGHNGQRPGGS YLPPSQGGNGGYPSGGPGGYPSGGPGGNGGYGGEEEESTEPAKYEFEYQVDD DEHNTHFGHQESRDGDKATGEYNVLLPDGRKQVVQYEADSEGYKPKISYEG GNGNGGGYPSGGPGGAGNGGYPSGGPQGGNGGYPSGGPQGGNGGYPSGGPQG GNGGYPSGGPQGGNGGYPSGGPQGGNGGYPSGGPQGGNGGYPSGGPQGGNG GYPSGGPQGGNGGYTSGGPQGGNGGYPSGGPQGGNGGSGPY |
| 14 | Tribolium castaneum | QLTKRDAPLSGGYPSGGPANSYLPPGGASQPSGNYGAPSGGFGGKSGGFGG SGGFGGAPSQSYGAPSGGFGGSSSFGKSGGFGGAPSQSYGAPSGGFGGSSS FGKSSGGFGGAPSQSYGAPSGGFGGSSSFGKSGGFGGAPSQSYGAPSGGFG GSSSFGKSGGFGGAPSQSYGAPSGGFGGKSSSFSSAPSQSYGAPSGGFGGK SGGFGGAPSQSYGAPSGGFGGKSGGFGGAPSQSYGAPSGGFGGSSSFGKSG GFGGAPSQSYGAPSGGFGGSSSFGKSSGFGHGSGAPSQSYGAPSRSQPQSN YLPPSTSYGTPVSSAKSSGSFGGAPSQSYGAPSQSHAPSQSYGAPSRSFSQ APSQSYGAPSQGHAPAPQQSYSAPSQSYGAPSGGFGGGHGGFGGQGQGFGG GRSQPSQSYGAPAPSQSYGAPSAGGQQYASNGGYSY |
| 15 | Apis mellifera | RSEPPVNSYLPPSGNGNGGGGGSSNVYGPPGFDGQNGIGEGDNGRNGISN SYGVPTGGNGYNGDSSGNGRPGTNGGRNGNGNGRGNGYGGGQPSNSYGPPS NGHGGNGAGRPSSSYGAPGGGNGFAGGSNGKNGFGGGPSSSYGPPENGNGF NGGNGGPSGLYGPPGRNGGNGGNGGNGGRPSGSYGTPERNGGRLGGLYGAP GRNGNNGGNGYPSGGLNGGNGGYPSGGPGNGGANGGYPSGGSNGDNGGYPS GGPNGNGNGGGYGQDENNEPAKYEFSYEVKDEQSGADYGHTESRDGDRAQ GEFNVLLPDGRKQIVEYEADQDGFKPQIRYEGEANSQGYGSGGPGGNGGDN GYPSGGPGGNGYSSGRPNGGSDFSDGGYPSTRPGGENGGYRNGNNGGNGNG GYPSGNGGDAAANGGYQY |
| 16 | Apis mellifera | DAPISGSYLPPSTSYGTPNLGGGGPSSTYGAPSGGGGGRPSSSYGAPSSTY GAPSSTYGAPSNGGGRPSSTYGAPSNGGGRPSSSYGAPSSSYGAPSSTYGA PSNGGGRPSSSYGAPSFGGGGGFGGGNGLSTSYGAPSRGGGGGGSISSSY GAPTGGGGGGPSTTYGAPNGGGNGYSRPSSTYGTPSTGGGSFGGSGGYSGG GGGYSGGGNGYSGGGGGYSGGNGGGYSGGNGGYSGGNGGGYSGGGGG YSGGGGGYSGGGNGYSGGGGGYSGGNGGYSGGNGGYSGGGGGYSGGGGG GQSYASNGGYQY |
| 17 | Nasonia vitripennis | RPEPPVNSYLPPGQGGFGGGRPSGASPSDQYGPPDFQGAGGRGGQAAGGN FGGGGNGFGGAPSSSYGPPGFGSNEPNKFSGAGGGGAGRPQDSYGPPAGGN GFAGSAGAGNSGRPGGAAAGGRPSDSYGPPQGGSGFGGGNAGRPSDSYGP PSAGGGGFGGGSPGGGFGGGSPGGGNGQAPQSSYGPPASGFGGQGGA GQGRPSDSYGPPGGGSGGRPSQGGNGFGGGNAGRPSDSYGPPAAGGGFGG NAGGNGGGNGFGGGRPSGSPGGFGGQGGGGRPSDSYLPPSGGSGFGGGNGR QPGGFGQQGGNGAGQQNGGGGAGRPSSSYGPPSNGNGGGFGSQNGGRGSPS SGGGFGGAGGSPSSSYGPPAGGSGFGNNGGAGGRPSSSYGPPSSGGNGFGS GGGGGGGGGGGGGRPSSSYGPPSNGNGGFGGGNGGRPSNGYPQGQGNGN GGFGGQGGNGGRPSSSYGPPGGDSGYPSGGPSGNFGGSNAGGGGGGFGGQV |

| SEQ ID NO: | Species | Sequence |
|---|---|---|
| | | QDSYGPPPSGAVNGNGNGYSSGGPGGNGLDEGNDEPAKYEFSYEVKDDQSD GRKQIVEYEADQDGFKPQIRYEGEANTGAGGAGGYPSGGGGDSGYPSGPSG AGGNAGYPSGGGGGAGGFGGNGGGSNGYPSGGPSGGQGQFGGQQGGNGGYP SGPQGGSGFGGGSQGSGSGGYPSGGPGGNGGNNNFGGGNAGYPSGGPSGGN GFNQGGQNQGGSGGGYPSGSGGDAAANGGYQYS |
| 18 | Nasonia vitripennis | RAEAPISGNYLPPSTSYGTPNLGGGGGGGGFGGGAPSSSYGAPSSGGGFG GSFGGGAPSSSYGAPSTGGSFGGGAPSSSYGAPSSGGSFGGSFGGGAPSSS YGAPSFGGNAPSSSYGAPSAGGSFGGGAPSNSYGPPSSSYGAPSAGGSFGG SSGGSFGGSFGGGAPSSSYGAPAPSRPSSNYGAPSRPSSNYGAPSSGGSGF GGGSGFGGGRPSSSYGAPSSGSFGGGFGGGAPSSSYGAPAPSRPSSNYGAP APSRPSSNYGAPAPSRPSSSYGAPSRPSSNYGAPSRPSSNYGAPSSGGSGF GGGGSGFGGGRPSSSYGAPSSGSFGGGFGGGAPSSSYGAPAPSRPSSNYGPP SSSYGAPSSGGSGGFGGGAPSSSYGAPSFGGSSNAVSRPSSSYGAPSSGGG QSYASNGGYQY |
| 19 | Pediculus humanus corporis | EPPVKTSYLPPSASRSLNSQYGAPAFTDSNELVAPSPNSNFHDSYNQQQQS FDLSNGLSVPSAAGRLSNTYGVPSAQGANVPSFDSSDSIAVDAAGRSGNSF SSHVPSSTYGAPGNGFGGGSRSSQSGAPSSVYGPPQARNNNFGNGAAPSSV YGPPQARNNNFGNGGAPSQVYGPPKARNNNFGNGAAPSSVYGPPQARNNNF GNGAAPSSVYGPPQARNNNFANSAAPSQVYGPPQARNNNFGNGAAPSSVYG PPQSSSFSSPSGRSGQLPSATYGAPFERNGFGSQGSSGFQGYEPSKRSQTT EDPFAEPAKYEYDYKVQASDETGTEFGHKESRENESARGAYHVLLPDGRMQ IVQYEADETGYRPQIRYEDTGYPSAASSRSNNGFNGYQY |
| 20 | Anopheles gambiae str. PEST | KREAPLPPSGSYLPPSGGAGGYPAAQTPSSSYGAPTGGAGSWGGNGGNGGR GHSNGGGSSFGGSAPSAPSQSYGAPSGGQSSGFGGGHSSGGFGGHSSGGH GGNGNGNGNGYSSGRPSSQYGPPQQQQQQQSFRPPSTSYGVPAAPSQSYGA PAQQHSNGGGNNGYSSGRPSTQYGAPAQSNGNGFGNGRPSSSYGAPARPSTQ YGAPSAGNGNGYAGNGNGRSYSNGNGNGHGNGHSNGNGNNGYSRGPARQPS QQYGPPAQAPSSQYGAPAQTPSSQYGAPAQTPSSQYGAPA QTPSSQYGAPAPSRPSQQYGAPAPSRPSQQYGAPAQTPSSQYGAPAQTPSS QYGAPAQTPSSQYGAPAQTPSSQYGAPAQQPSSQYGAPAPSRPSQQYGAPA QQPSAQYGAPAQTPSSQYGAPAPSRPSQQYGAPAQAPSSQYGAPAPSSQYG APAQQPSSQYGAPAQTPSSQYGAPSFGPTGGASFSSGNGNVGGSYQVSSTG NGFSQASFSASSFSPNGRTSLSAGGFSSGAPSAQSAGGYSSGGPSQVPATL PQSYSSNGGYNY |
| 21 | Glossina morsitans | RPEPPVNTYLPPSAGGGSGGGSPLAPSDTYGAPGVNGGGGGGGGPSSTYGA PGSGGGNGNGGGGFGKPSSTYGAPGLGGGGNGGGRPSETYGAPSGGGGNGF GKPSSTYGAPNGGGNGGPRPSSTYGAPGSGGGNGGSGRPSSTYGAPGLG GGNGGSGRPSSMYGAPGLGGGNGGSGRPSSTYGAPGSGGGNGGSGRPSSTY GAPGSGGGNGGSGRPSSTYGAPGNGNGGNGFGRPSSTYGAPGSGGSNGNGK PSSTYGAPGSGGGGRPSDSYGPPASGNGGRNGNGNGQSQEYLPPGQSGSG GGGGYGGGSGSGGSGGGGGGGYGGDQDNNVVEYEADQEGYRP QIRYEGDGS QGGFGGDGDGYSYEQNGVGGDGGGAGGAGGYSNGQNLGANGYS SGRPNGGN GGGGRRGGGGGGGSGGGQNLGSNGYS SGAPNGFGGGNGQGYSGGRSNGNGG GGGGRNGGRYRNGGGGGGGRNGGGSNGYNYDQPGSNGFGRGGGNGENDSG YHY |
| 22 | Atta cephalotes | RSEPPVNSYLHPGSDTSGTNGGRTDLSTQYGAPDFNNRGNGNSGATSFGGS GAGNGPSKLYDVPIRGNTGGNGLGQFRGNGFESGQPSSSYGAPKGGFGENR GNRGRPSTSYGVPDSNRNNRGGFGNGGSEARPSTYGVPGANGNQGGFGSG SIGGRPSTSYGVPGANGNNGDSFRNGDIGGRPSTNYGAPGANGNHGGGNGG NGRPSNNYGVPGANGNTNGKGRLNGNSGGGPSNNYGSPNGFGKGLSTSYGS PNRGGNDNHYPSRGSFINGGINGYSSGSPNGNAGNFGHGDESFGRGGGEGE NTGEGYNANAQEESTEPAKYEFSYKVKDQQTGSDYSHTETRDGDHAQGEFN VLLPDGRKQIVEYEADQDGFKPQIRYEGEANADGGYGSGLNDNNDGYSSGR PDSESGGFANSGFNGGSSNGGYPNGGPGERKLGGFNNGGSSGYQSGRSAGQ SFGRDNAGDLNNDIGGYFSNSPNNIGDSDNANVGSNRQNDGNSGYQY |
| 23 | Anopheles darlingi | KREAPLPPSGSYLPPSGGGGGGGYPAAQTPSSSYGAPAGGAGGWGGNGNGG NGNGNGGRGGYSNGGGHSGSAPSQSYGAPSAPSQSYGAPSQSYGAPAAAPS QSYGAPSFGGNGGGASHGSGGFTGGHGGNGNGNGYSSGRPSSQYGPPQQQQ QPQQQSFRPPSTSYGVPAAPSSSYGAPSANGFSNGGRPSSQYGAPAPQSNG NEFGAPRPSSSYGAPSRPSTQYGAPSNGNGNGYAGHGNGNGHGNGNGHSNG NGNGYNRGPARQPSSQYGPPSQGPPSSQYGPPSQYGPPSSGTSFIAYGPPS QGPPSSQYGAPAPSRPSSQYGAPAQTPSSQYGAPAQTPSSQYGPPRQSSPQ FGAPAPRPPSSQYGAPAQAPSSQYGAPAQTPSSQYGAPAQAPSSQYGAPAP SRPSSQYGVPAQAPSSQYGAPAQAPSSQYGAPAQTPSSQYGAPSFGSTGGS SFGGNGGVGGSYQTASSGNGFSQASFSASSFSSNGRSSQSAGGYSSGGPSQ VPATIPQQYSSGGGSYSSGGHSQVPATLPQQYSSNGGYNY |
| 24 | Acromyrmex echinatior | RSEPPVNSYLPPGPGTSGANGGQTDLSIQYRASDFNNRGNVNGNSGATSFG GPGASNGPSKLYDVPIGGNAGGNGLGQFRGNGFEGGQPSSSYGAPNGGFGE NRGNGGKPSTSYGVPDSNGNNRGGFGNGGSEGRPSTSYGLPDASRNNGNGF |

| SEQ ID NO: | Species | Sequence |
|---|---|---|
| | | GNVGNEDKPSTNYGIPANGNKVSGFGNVGSEGRPSTSYGVPGANGNQGFGS<br>GGIGGRPSTSYGVPGVNGNNGGGFENVGRPSTSYGTPDARGNNGGSFRNGD<br>IGGRPSTNYGIPGANGNHGGGNGGNGRPSSNYGVPGGNGNTNGKGRFNGNS<br>GGRPSNSYGSPNGFGKGLSTSYSPSNRDGNGNHYPSGDSNRGSFVNGGING<br>YPSGSPNGNAGNFRHGDESFGRGGEGGGRSTGEGYNANAQEESTEPAKYEF<br>SYKVKDQQTGSDYSHTETRDGDHAQGEFNVLLPDGRKQIVEYEADQDGFKP<br>QIRYEGEANADGEYDSGGLNDNNDGYSSGRPGSESGGFANNSGFNGGSSNG<br>GYPSGGSGEGKLGFNSGGNSGYQSGRPAGQSFGRDNAGDLSNDIGGFSNSP<br>NNIGGDNANVGSNRQNGGNSGYQY |
| 25 | Acyrthosiphon pisum | ESPYGGGSSNSNGNGRNGGYGGKGQYGGGNGGGVGSSSASPFFSGANQYGS<br>QSGLSGAANNRYPSFGSKFGGNKGSYGGSSSRNNGRYGSGSASGYGSGSSG<br>GLGSTGRSTGGYGGGSSGSYGSGSSGSLGSSTGSNGIYGAGSSGGFGSGSS<br>GSYGGGSSGGFGSGSSGSYGGGSSGGFGSGSSGSYGGGSSGGFGSGSSGSY<br>GGGSSGGFGSGSSGNYGSGSSGSYGSGGGLGGASSGNNDGYGAGGSGSYD<br>QLGGANGNGLGGSGNDPLSEPANYEFSYEVNAPESGAIFGHKESRQGEEAT<br>GVYHVLLPDGRTQIVEYEADEDGYKPKITYTDPVGGYAGDRQSGNSYGGNG<br>GFGGSGSLGGSGGNLGGLYNGGGSSNNGAGYGGSSSSLGSRYGGSGGSSGS<br>GVGGGYGGSGSSSGGIGSSYGGSGSLSGGLGGGYGGSGSSSGGLGGGYGGS<br>GGSSGGGFGGLGGSGGSSGSGYGGSGSSSGGLGNSYGGSGSSNGGLGGGYS<br>GSGGSSGGLGGGYGASSGSSGSGLGGGYGGSGSSSGGLGSGYGGLGSSSGG<br>LGGGYGGSGSSSGGLGGGYGGSGSSNGGIGGGYGGSGSSGGLGGGYGGSG<br>SSSGGLGGGYGGSGGSNSGLGSSYGGSGSTNGGLGGGYGGLGSSSGGLGGG<br>YGGSGGSNGGIGGGYGGSSGSGGSQGSAYGGSGSSSGSQGGGYGGSGSSSG<br>GLGGGYGSSSGSSSGLGGSYGSNRNGLGSGSSYS |
| 26 | Drosophila virilis | RPEPPVNSYLPPSPGDSYGAPGQGQGQGQGGFGGKPSDSYGAPGAGNGNGN<br>GRPSSSYGAPGQGQGQGGFGGKPSDSYGAPGAGNGNGNGRPSSSYGAPGQG<br>QGQGGFGGRPSSSYGAPGQGQGGFGGKPSDTYGAPGAGNGNGRPSSSYGAP<br>GQGQGGIGGKPSDSYGAPGAGNGNGRPSSSYGAPGQGQGGFGGKPSDTY<br>GAPGAGNGNGRPSSSYGAPGQGQGGFGGKPSDTYGAPGAGNGNGNGRPSSS<br>YGAPGQGQGGFGGKPSDTYGAPGAGNGNGRPSSSYGAPGQGQGQGGFGGKP<br>SDSYGPPASGAGAGGAGGPGAGGGGDYDNDEPAKYEFNYQVEDAPSGLSFG<br>HSEMRDGDFTTGQYNVLLPDGRKQIVEYEADQQGYRPQVRYEGDANGNGGP<br>GGAGGPGGQDLGQNGYSSGRPGGQDLGQGGYSNGRPGGQDLGQNGYSGGRP<br>GGQDLGQNGYSGGRPGGQDLGQNGYSGGRPGGQDLGQNGYSGGRPGGQDLG<br>QNGYSGGRPGGQDLGQNGYSGGRPGGNGGSDGGRVIIGGRVIGQDGGDGQG<br>YSSGRPNGQDGGFGQDNTDGRGYSSGKPGQGRNGNGNSFGPGGQNGDNDGS<br>GYRY |
| 27 | Drosophila erecta | RPEPPVNSYLPPSDSYGAPGQSGPGGRPSDSYGAPGGGNGGRPSDSYGAPG<br>LGQGQGQGQGGFGGKPSDSYGAPGAGNGNGGRPSSSYGAPGAGNGGRPS<br>DTYGAPGGGSSGRPSDTYGAPGGGNGNGGRPSSSYGAPGQGQGNGNSGR<br>PSSSYGAPGAGNGGRPSDTYGAPGGGNGGRPSSSYGAPGAGNGGNGGRPSD<br>TYGAPGGGNGNGNGNGSGGRPSSSYGAPGQGQGGFGGRPSDSYGAPGQN<br>QKPSDSYGAPGSGSGSGNGNGGRPSSSYGAPGSGPGGRPSDSYGPPASGSG<br>AGGAGGSGPGGADYDNDIVEYEADQQGYRPQIRYEGDANDGSGPSGPGGQN<br>LGADGYSSGRPGNGNGNGGYSGGRPGGQDLGPSYGYSGGRPGGQDLGAGG<br>YSNGRPGGQDLGPSGYSGGRPGGQDLGPSGYSGGRPGGQDLGAGGYSNGRP<br>GGNGNGNGGADGGRVIIGGRVIGGQDGGDQGYSSGGRPGGQDLGRDGYSSGR<br>PGGRPGANGQDNQDGQGYSSGRSGKGGRNSFGPGGQNGDNDGSGYRY |
| 28 | Lutzomyia longipalpis | RPEPPANTYLPPSSSYAAPGQQGGSFGGGGSGGSGGFGQPGAFGRPSSS<br>YGPPSQGGAGGGFGSDSQFGGGFGGGAGGFGSGGSGAPGASQRPSSSYGPP<br>GQTGGGGFGAQGAPGSSFGPGGGFGGGSPGQAGSPGFQRPSSSYGPPGQSP<br>GGGFSQQGGAPGASQRPSSTYGAPGQGAGGFGQGGSGGFGGTGGSVAIGGR<br>PSSSYGAPGQGSSGGFGGGSGGFGSQAPSTSYGAPGQGSPGGGFGSQGGPG<br>GQPGSPGFGGSQRPSSSYGPPGQGGAPGQGGSPGFGASSRSGGAGGFGASQ<br>QPSSSYGPPGQGAGSGFQGTGGGFGGPGQRPGFGGSQTPATSYGAPGQAGG<br>ASGGFGGAGAQRPSSSYGPPGQASGFGGGSSGGGFGGGSSGGFGGNQGGFG<br>GNQGGFGGSQTPSSSYGAPSFGSGGSPGAAGGAGGFGQGGVGGSGQPGGFG<br>GGDQGYPPRGGPGGFGPGSGGSGAGGPIAGGSGSGYPGGSDSGSNEPAKYD<br>FSYQVDDPASGTSFGHSEQRDGDYTSGQYNVLLPDGRKQIVEYEADLGGYR<br>PQIKYEGGSSGGAGGYPSGGPGSQGGAGGYPSGGPGGPGSPGGAGGYQSGA<br>AGGAGGYPSGGPGGPGAGGYPSGGPGGPGSQAGGFSGGFGGGSDGAFGGAG<br>GFSQGGAGGGDAGYPRGGPGGFGGAGSPGFGGSGSPGFGGSGSPGAQGSSG<br>FGGTGGGFGGGADYPRGGPGAGQSGFQDGRGATGGAGQPGGRGSFGRPGS<br>ARGGSSSNGYANGGAEGYPRDNPQNRGSGYS |
| 29 | Rhodnius prolixus | KRDDPLRRFLAPLVGGGNGSGGGGGGYNYNKPANGLSLPGGGGALPPATSY<br>GVPDRPAPVPSSPPSSSYGAPQPSPNYGAPSSSYGAPSQQPSRSYGAPSQG<br>PSTSYSQRPSSSYGAPAPQTPSSSYGAPAQQPSGSYGAPSGGGSSGYTGG<br>AQRPSGSYGAPSQGGPSGNYGPPSQQPSNYGAPSQTPSSNYGAPAQRPST<br>SYGAPSQPPSSSYGSPPQRASGYPSSSGPSNGYSPPAQRPSSSYGPPSQQ<br>PASSYGAPSQTPSSNYGPPAPIPSSNYGAPSQPPSKPSAPSSSYGTPSQTP<br>STSYGAPSQAPSSSYGAPSRPSPPSSSYGAPSQGPSSSYGPPSRPSQPSSP |

| SEQ ID NO: | Species | Sequence |
|---|---|---|
|  |  | SSGYGAPSQGPSSSYGAPSRPSSPSSSYGAPPSSSYGAPSRPSPPSSSYGA<br>PSQGPSSSYGPPSRPSQPSSPSSSYGAPSQGPSSSYGAPSRPSSPSSSYGA<br>PPSSSYGAPSRPSPPSSSYGAPSQGPSSSYGPPSRPSQPSSPSSSYGAPSQ<br>GPSSSYGAPSRPSPPSSSYGAPSQGPSSSYGPPSRPSQPSSTYGVPSGGRP<br>STPSSSYGAPPQALSSTYGAPSGRPGAPSQKPSSSYGAPSLGGNASRGPKS<br>SPPSSSYGAPSVGTSVSSYAPSQGGAGGFQSSRPSSSYGAPSTGPSSTYGP<br>PSQPPSSSYGVPSQPPSSNYGVPSQGVSGSVGSSSPSSSYGAPSQIPSSSY<br>GAPSQSSIGGFGSSRPSSSYGAPPQAPSSSYSAPLRAPSTSYGAPSGGSGS<br>NFGSKPSTNYGAPSQPPSTNYGPPSQPPSSSYGTPSRAPSPTYSTPQSSGT<br>SFGSRPSSSYGVPSQPTTNYGAPSQTPSSNYGAPPASSAPSSTYGRPSQSP<br>SSSYGAPSPSSSSSYESPSQPPSSSYGAPSQGPSSSYGAPSRPSSTYGAP<br>SPSSPSTNYGAPAPSSNYGTPAQDLTGSYAAPSQPPSAGYGAPSGQPSSGG<br>KQNFQVKNPFAGQTHQVYPAVSSISFGLPSQSFNTAIQGQEPSQSYGAPTA<br>SSPSSSYGAPTGTGSSQPGQSYASNGGYSYS |
| 30 | Rhodnius prolixus | QPPFNHYLPAARGSGSNSAQYTAPSSKFGTSTGQYGQPPSEVPRGLQQGSY<br>AEDVHSSRSVNPSSQNGIPSGHFSSLSSNYGAPSSDYSRSFLRYGTLSNKY<br>GVPNSALGSLSSRNNKTPATQLSYQPSSHYDSRSTSEDQFISSRVSDSQYG<br>ASSVRRFLPSSQYSTPSSQYGTPSSQYGTPSSQYGTPSSQYGTPSSQYGTP<br>SSQYGTPSSQYGTPSSQYGTPSSQYGTPSSPPSQYGGPYSMRTS<br>APNSQYGTPSSFRTPSSQFGSSSAHSSSLSKFRSVPSSPYGTLSAIRSTH<br>SSQYGTPSSFSDSTSSSHNGLPSHYPGSGFSGSSVNDQKSYTGNVFGQSHS<br>RVANGDQHARSYTLAGGNEISEPAKYDFNYDVSDGEQGVEFGQEESRDGEE<br>TNGSYHVLLPDGRRQRVQYTAGQYGYKPTISYENTGTLTTGRQQFSNGFYN<br>VQQSGSESQEHLGRSTGQNSYGGSNGYESGVGYQSGVGRRSRPAGSY |
| 31 | Solenopsis invicta | RSEPPINSYLPPRAGSSGANGGRTDLTTQYGAPDFNNGGGATSFSGNGAGD<br>GPSKLYDVPVRGNAGGNGLGRGNGFGGGQPSSSYGAPNGGSNENRGNGGRP<br>STSYGVPGANGNNGGGFGNGGDKGRPSTSYGVPDASGSSQGSFGNVGNGGR<br>PSTNYGVPGANGNGGGFGNAANEGKPSTSYGVPGANGNSQGGFGNGGRPST<br>GYGVPGANGNNGGGFGGRPSTSYGAPGANGNHRGGNGGNASPSTNYGVPGG<br>NNGNTNGKGRFNGGNSGGGPSNNYGVPNENAFGGGLSTSYGPPSRGGNGNS<br>GYPSGGSNGGSFVNNGANGYPSGGPNGNAGNFGDGRGGKGGGSSGEGYNDN<br>AQEGSTEPAKYEFSYKVKDQQTGSEYSHTETRDGDRAQGEFNVLLPDGRKQ<br>IVEYEADQDGFKPQIRYEGEANAGGGYSSGGSNDNNDGYSSGRPGSEAGGF<br>ANNSGFNGSGTNGGRSSGGPGDGNPGGFNSGGGGGYQSGRPAGQSFGRDND<br>GGLSGDIGGYFANSPSNNIGGSDSANVGSNRQNGGNGGYQY |
| 32 | Culex quinquefasciatus | KREAPLPGGSYLPPSNGGGAGGYPAAGPPSGSYGPPSNGNGNGAGGYPS<br>APSQQYGAPAGGAPSQQYGAPSNGNGGAGGYPSAPSQQYGAPNGNGNGGFG<br>GRPQAPSQQYGAPSNGNGGARPSQQYGAPNGNGNGRPQTPSSQYGAPSGG<br>APSSQYGAPSGGAPSQQYGAPNGGNGNGRPQTPSSQYGAPSGGAPSQQYGA<br>PNGGNGNGRPQTPSSQYGAPSGGAPSSQYGAPSGGAPSSQYGAPAGGAPSS<br>QYGAPAGGAPSSQYGAPAGGAPSSQYGAPAGGAPSSQYGAPAGGAPSSQYG<br>APSSQYGAPAGGAPSSQYGAPAGGAPSSQYGAPSGGAPSSQYGAPSGGAPS<br>SQYGAPAGGAPSSQYGAPSGGAPSS |
| 33 | Bactrocera cucurbitae | RPEPPVNSYLPPSANGNGNGGGRPSSQYGAPGLGSNSNGNGNGNGGGRPSS<br>QYGVPGLGGNGNGNGNGGGGGRPSSSYGAPGLGGNGNGNGNGGGRPSSQYG<br>VPGLGGNGNGNGNGNGGGRPSSTYGAPGLRGNGNGNGNGRPSSTYGAPG<br>LGGNGNGNGNGNGRPSSTYGAPGLGGNGNGNGNGRPSSTYGAPGLNGNG<br>LGGGQKPSDSYGPPASGNGNGYSNGGNGNGNGGGRPGQEYLPPGRNGNGNG<br>NGGRGNGNGGGANGYDYSQGGSDSGESGIVDYEADQGGYRPQIRYEGEANN<br>GAGGLGGGAGGANGYDYEQNGNGLGGGNGYSNGQDLGSNGYSSGRPNGNGN<br>GNGNGNGNGYSGRNGKGRNGNGGGQGLGRNGYSDGRPSGQDLGDNGYASGR<br>PGGNGNGNGGNGNGYSNGNGYSNGNGNGTGNGGGQYNGNGNGYSDGRPGGQ<br>DNLDGQGYSSGRPNGFGPGGQNGDNDGNGYRY |
| 34 | Trichogramma pretiosum | RPEPPVNSYLPPGQGGQGGFGGSGGRPGGGSPSNQYGPPNFQNGGGQNGGS<br>GFGGNGNGNSFGPPSNSYGPPEFGSPGAGSFGGGRPQDTYGPPSNGNGNGN<br>GFGGNGNGGGRPSSRPSDSYGPPSSGNGFGGGNSGRPSESYGPPQNGGGSG<br>NGNQGGGNGFGNGGGRGGGQGKPSDSYGPPNSGNRPGSSNGGGQQQNGFGGG<br>NGGRPSNTYGPPGGNGGGRPGGSSGGFGGQNGGRPSDSYGPPSNGNGNGG<br>RPSNNYGPPNSGGGNGNGFGGSNGKPSNSYGPPSNGNGGGFGGSNGRPSNS<br>YGPPSGGNGGGFGGSSAVGRPGNSGSPSSSGSGFGGNGGASRPSSSYGPPS<br>NGGGFGNGGGSNGRPSSSYGPPNSGNGGGFGGQNGNGRQNGNNGQGGFGG<br>QPSSSYGPPSNGNGFGGGGGSNGYPQNSQGGNGNGFGQGSSGRPSSSYGPP<br>SNGGGGGDNGYSSGGPGGFGGQPQDSYGPPPSGAVDGNNGFSSGGSSGDNN<br>GYSSGGPGGNGFEDGNDEPAKYEFSYEVKDEQSGSSFGHTEMRDGDRAQGE<br>FNVLLPDGRKQIVEYEADQDGFKPQIRYEGEANTGGAGGYPSGGPGGQGGN<br>GNGGYPSGGPSNGGFGGQNGGGYPSGGPSGGFGGQNGGSGGYPSGGP<br>SGGGFGGQGGFGGQNGGNGGYSSGGPASGGFGGQNGGNGGYPSGGPSGGG<br>FGGQGGFGGQNSGGNGGYPSGGPSSGGFGGQNGGGGNYPAGSGGDAEANG<br>GYQYS |
| 35 | Drosophila | QSGAGGRPSDTYGAPGGGNGGRPSDSYGAPGQGQGQGQGGYGGKPSDSY |

| SEQ ID NO: | Species | Sequence |
|---|---|---|
| | sechellia | GAPGGGNGNGGRPSSSYGAPGGGNGGRPSDTYGAPGGGNGGRPSDTYGAPG GGGNGNGGRPSSSYGAPGQGQGNGNGGRPSSSYGAPGGGNGGRPSDTYGAP GGGNGGRPSDTYGAPGGGNNGGRPSSSYGAPGGGNGGRPSDTYGAPGGGNG NGSGGRPSSSYGAPAQGQGGFGGRPSDSYGAPGQNQKPSDSYGAPGSGNGS AGRPSSSYGAPGSGPGGRPSDSYGP |
| 36 | Drosophila sechellia | QSGAGGRPSDTYGAPGGGNGGRPSDSYGAPGQGQGQGQGGYGGKPSDSY GAPGGGNGNGGRPSSSYGAPGGGNGGRPSDTYGAPGGGNGGRPSDTYGAPG GGGNGNGGRPSSSYGAPGQGQGNGNGGRPSSSYGAPGGGNGGRPSDTYGAP GGGNGGRPSDTYGAPGGGNNGGRPSSSYGAPGGGNGGRPSDTYGAPGGGNG NGSGGRPSSSYGAPAQGQGGFGGRPSDSYGAPGQNQKPSDSYGAPGSGNGS AGRPSSSYGAPGSGPGGRPSDSYGP |
| 37 | Drosophila sechellia | QSGAGGRPSDTYGAPGGGNGGRPSDSYGAPGQGQGQGQGGYGGKPSDSY GAPGGGNGNGGRPSSSYGAPGGGNGGRPSDTYGAPGGGNGGRPSDTYGAPG GGGNGNGGRPSSSYGAPGQGQGNGNGGRPSSSYGAPGGGNGGRPSDTYGAP GGGNGGRPSDTYGAPGGGNNGGRPSSSYGAPGGGNGGRPSDTYGAPGGGNG NGSGGRPSSSYGAPAQGQGGFGGRPSDSYGAPGQNQKPSDSYGAPGSGNGS AGRPSSSYGAPGSGPGGRPSDSYGP |
| 38 | Drosophila sechellia | QSGAGGRPSDTYGAPGGGNGGRPSDSYGAPGQGQGQGQGGYGGKPSDSY GAPGGGNGNGGRPSSSYGAPGGGNGGRPSDTYGAPGGGNGGRPSDTYGAPG GGGNGNGGRPSSSYGAPGQGQGNGNGGRPSSSYGAPGGGNGGRPSDTYGAP GGGNGGRPSDTYGAPGGGNNGGRPSSSYGAPGGGNGGRPSDTYGAPGGGNG NGSGGRPSSSYGAPAQGQGGFGGRPSDSYGAPGQNQKPSDSYGAPGSGNGS AGRPSSSYGAPGSGPGGRPSDSYGP |
| 39 | Drosophila sechellia | YSSGRPGNGNGNGGYSSGRPGGQDLGPSGYSGGRPGGQDLGAGGYSNVK PGGQDLGPGGYSGGRPGGQDLGRDGYSGGRPGGQDLGAGAYSNGRPGGNGN GGSDGGRVIIGGRVIGGQDGGDQGYSGGRPGGQDLGRDGYSSGRPGGRPGG NGQDSQDGQ |
| 40 | Drosophila sechellia | YSSGRPGNGNGNGGYSSGRPGGQDLGPSGYSGGRPGGQDLGAGGYSNVK PGGQDLGPGGYSGGRPGGQDLGRDGYSGGRPGGQDLGAGAYSNGRPGGNGN GGSDGGRVIIGGRVIGGQDGGDQGYSGGRPGGQDLGRDGYSSGRPGGRPGG NGQDSQDGQ |
| 41 | Drosophila sechellia | YSSGRPGNGNGNGGYSSGRPGGQDLGPSGYSGGRPGGQDLGAGGYSNVK PGGQDLGPGGYSGGRPGGQDLGRDGYSGGRPGGQDLGAGAYSNGRPGGNGN GGSDGGRVIIGGRVIGGQDGGDQGYSGGRPGGQDLGRDGYSSGRPGGRPGG NGQDSQDGQ |
| 42 | Drosophila sechellia | YSSGRPGNGNGNGGYSSGRPGGQDLGPSGYSGGRPGGQDLGAGGYSNVK PGGQDLGPGGYSGGRPGGQDLGRDGYSGGRPGGQDLGAGAYSNGRPGGNGN GGSDGGRVIIGGRVIGGQDGGDQGYSGGRPGGQDLGRDGYSSGRPGGRPGG NGQDSQDGQ |
| 43 | Drosophila sechellia | YSSGRPGNGNGNGGYSSGRPGGQDLGPSGYSGGRPGGQDLGAGGYSNVK PGGQDLGPGGYSGGRPGGQDLGRDGYSGGRPGGQDLGAGAYSNGRPGGNGN GGSDGGRVIIGGRVIGGQDGGDQGYSGGRPGGQDLGRDGYSSGRPGGRPGG NGQDSQDGQ |
| 44 | Drosophila sechellia | YSSGRPGNGNGNGGYSSGRPGGQDLGPSGYSGGRPGGQDLGAGGYSNVK PGGQDLGPGGYSGGRPGGQDLGRDGYSGGRPGGQDLGAGAYSNGRPGGNGN GGSDGGRVIIGGRVIGGQDGGDQGYSGGRPGGQDLGRDGYSSGRPGGRPGG NGQDSQDGQ |
| 45 | 3X FLAG | GDYKDDDDKDYKDDDDKDYKDDDDK |
| 46 | Alpha mating factor precursor protein sequence | MRFPSIFTAVLFAASSALAAPVNTTTEDETAQIPAEAVIGYSDLEGDFDVA VLPFSNSTNNGLLFINTTIASIAAKEEGVSLEKR |
| 47 | EA repeat | EAEA |
| 48 | Linker | SG |

What is claimed is:

1. A method for producing a composition comprising a recombinant resilin protein, comprising:
   culturing a population of recombinant yeast host cells in a fermentation, wherein said recombinant yeast host cells comprise a vector comprising a secreted resilin coding sequence selected from the group consisting of SEQ ID NOs: 2, 3, 5, 6, 7, 8, 9, 10, 11, and 12, and wherein said recombinant yeast host cells secrete a recombinant resilin protein encoded by said secreted resilin coding sequence; and
   purifying said recombinant resilin protein from said fermentation.

2. The method of claim 1, wherein said recombinant resilin protein is a full-length or truncated native resilin.

3. The method of claim 1, wherein the recombinant resilin protein comprises an alpha mating factor secretion signal.

4. The method of claim 1, wherein the recombinant resilin protein comprises a FLAG-tag.

5. The method of claim 1, wherein the vector comprises more than one secreted resilin coding sequence.

6. The method of claim 1, wherein the recombinant yeast host cells are methylotrophic yeast cells.

7. The method of claim 1, wherein the recombinant yeast host cells produce a secreted fraction of the recombinant resilin that is greater than 50% as compared to the total recombinant resilin protein expressed by the recombinant yeast host cells.

8. The method of claim 1, wherein greater than 80% of the recombinant resilin is outside of the recombinant host cells in said fermentation.

9. The method of claim 1, wherein the fermentation comprises at least 2 g recombinant resilin/L.

10. The method of claim 1, wherein purifying said recombinant resilin protein comprises
    generating a first pellet fraction and a first supernatant fraction by centrifuging the fermentation; and
    isolating the recombinant resilin protein from the first pellet fraction.

11. The method of claim 10, wherein purifying said recombinant resilin protein further comprises:
    adding a chaotrope to the first pellet fraction to generate a solution in which the recombinant resilin protein is soluble;
    generating a second supernatant fraction and a second pellet fraction by centrifuging the first pellet fraction comprising said chaotrope; and
    isolating the soluble full-length resilin from the second supernatant fraction.

12. A vector comprising a secreted resilin coding sequence selected from the group consisting of SEQ ID NOs: 2, 3, 5, 6, 7, 8, 9, 10, 11, and 12.

13. A recombinant host cell comprising the vector of claim 12.

14. A fermentation comprising the recombinant host cell of claim 13 and a culture medium suitable for growing the recombinant host cell.

15. A composition comprising recombinant resilin derived from a fermentation of claim 14.

16. A composition comprising a gel comprising a recombinant resilin selected from the group consisting of SEQ ID NOs: 1, 2, 3, 4, 5, 6, 7, 8, 9, 10, 11, and 12.

17. The composition of claim 16, wherein the recombinant resilin comprises the sequence set forth in SEQ ID NO: 1.

18. The composition of claim 16, wherein the recombinant resilin comprises the sequence set forth in SEQ ID NO: 4.

19. The composition of claim 16, wherein the gel comprises full-length resilin.

20. The composition of claim 16, wherein the gel comprises a plurality of cross-linked recombinant resilins.

21. The composition of claim 20, wherein the cross-linking comprises enzymatic cross-linking, photochemical cross-linking, or chemical cross-linking.

* * * * *

SEQUENCE LISTING

<160> NUMBER OF SEQ ID NOS: 63

<210> SEQ ID NO 1

```
<211> LENGTH: 606
<212> TYPE: PRT
<213> ORGANISM: Drosophila sechellia

<400> SEQUENCE: 1

Arg Pro Glu Pro Pro Val Asn Ser Tyr Leu Pro Pro Ser Asp Ser Tyr
1               5                   10                  15

Gly Ala Pro Gly Gln Ser Gly Ala Gly Gly Arg Pro Ser Asp Thr Tyr
            20                  25                  30

Gly Ala Pro Gly Gly Gly Asn Gly Gly Arg Pro Ser Asp Ser Tyr Gly
        35                  40                  45

Ala Pro Gly Gln Gly Gln Gly Gln Gly Gln Gly Gly Tyr Gly
50                  55                  60

Gly Lys Pro Ser Asp Ser Tyr Gly Ala Pro Gly Gly Asn Gly Asn
65                  70                  75                  80

Gly Gly Arg Pro Ser Ser Tyr Gly Ala Pro Gly Gly Asn Gly
                85                  90                  95

Gly Arg Pro Ser Asp Thr Tyr Gly Ala Pro Gly Gly Asn Gly Gly
                100                 105                 110

Arg Pro Ser Asp Thr Tyr Gly Ala Pro Gly Gly Gly Asn Gly Asn
            115                 120                 125

Gly Gly Arg Pro Ser Ser Tyr Gly Ala Pro Gly Gln Gly Gln Gly
        130                 135                 140

Asn Gly Asn Gly Gly Arg Pro Ser Ser Ser Tyr Gly Ala Pro Gly Gly
145                 150                 155                 160

Gly Asn Gly Gly Arg Pro Ser Asp Thr Tyr Gly Ala Pro Gly Gly Gly
                165                 170                 175

Asn Gly Gly Arg Pro Ser Asp Thr Tyr Gly Ala Pro Gly Gly Gly Asn
            180                 185                 190

Asn Gly Gly Arg Pro Ser Ser Tyr Gly Ala Pro Gly Gly Gly Asn
        195                 200                 205

Gly Gly Arg Pro Ser Asp Thr Tyr Gly Ala Pro Gly Gly Asn Gly
    210                 215                 220

Asn Gly Ser Gly Gly Arg Pro Ser Ser Ser Tyr Gly Ala Pro Ala Gln
225                 230                 235                 240

Gly Gln Gly Gly Phe Gly Gly Arg Pro Ser Asp Ser Tyr Gly Ala Pro
                245                 250                 255

Gly Gln Asn Gln Lys Pro Ser Asp Ser Tyr Gly Ala Pro Gly Ser Gly
            260                 265                 270

Asn Gly Ser Ala Gly Arg Pro Ser Ser Tyr Gly Ala Pro Gly Ser
        275                 280                 285

Gly Pro Gly Gly Arg Pro Ser Asp Ser Tyr Gly Pro Pro Ala Ser Gly
    290                 295                 300

Ser Gly Ala Gly Gly Ala Gly Gly Ser Gly Pro Gly Gly Ala Asp Tyr
305                 310                 315                 320

Asp Asn Asp Glu Pro Ala Lys Tyr Glu Phe Asn Tyr Gln Val Glu Asp
                325                 330                 335

Ala Pro Ser Gly Leu Ser Phe Gly His Ser Glu Met Arg Asp Gly Asp
            340                 345                 350

Phe Thr Thr Gly Gln Tyr Asn Val Leu Leu Pro Asp Gly Arg Lys Gln
        355                 360                 365

Ile Val Glu Tyr Glu Ala Asp Gln Gln Gly Tyr Arg Pro Gln Ile Arg
    370                 375                 380

Tyr Glu Gly Asp Ala Asn Asp Gly Ser Gly Pro Ser Gly Pro Ser Gly
```

```
                385                 390                 395                 400
Pro Gly Gly Pro Gly Gly Gln Asn Leu Gly Ala Asp Gly Tyr Ser Ser
                    405                 410                 415
Gly Arg Pro Gly Asn Gly Asn Gly Asn Gly Gly Tyr Ser Ser
                420                 425                 430
Gly Arg Pro Gly Gly Gln Asp Leu Gly Pro Ser Gly Tyr Ser Gly Gly
                    435                 440                 445
Arg Pro Gly Gly Gln Asp Leu Gly Ala Gly Gly Tyr Ser Asn Val Lys
            450                 455                 460
Pro Gly Gly Gln Asp Leu Gly Pro Gly Gly Tyr Ser Gly Gly Arg Pro
465                 470                 475                 480
Gly Gly Gln Asp Leu Gly Arg Asp Gly Tyr Ser Gly Gly Arg Pro Gly
                    485                 490                 495
Gly Gln Asp Leu Gly Ala Gly Ala Tyr Ser Asn Gly Arg Pro Gly Gly
                500                 505                 510
Asn Gly Asn Gly Gly Ser Asp Gly Gly Arg Val Ile Ile Gly Gly Arg
                515                 520                 525
Val Ile Gly Gly Gln Asp Gly Gly Asp Gln Gly Tyr Ser Gly Gly Arg
            530                 535                 540
Pro Gly Gly Gln Asp Leu Gly Arg Asp Gly Tyr Ser Ser Gly Arg Pro
545                 550                 555                 560
Gly Gly Arg Pro Gly Gly Asn Gly Gln Asp Ser Gln Asp Gly Gln Gly
                    565                 570                 575
Tyr Ser Ser Gly Arg Pro Gly Gln Gly Gly Arg Asn Gly Phe Gly Pro
                580                 585                 590
Gly Gly Gln Asn Gly Asp Asn Asp Gly Ser Gly Tyr Arg Tyr
                    595                 600                 605

<210> SEQ ID NO 2
<211> LENGTH: 304
<212> TYPE: PRT
<213> ORGANISM: Drosophila sechellia

<400> SEQUENCE: 2

Arg Pro Glu Pro Pro Val Asn Ser Tyr Leu Pro Ser Asp Ser Tyr
1               5                   10                  15
Gly Ala Pro Gly Gln Ser Gly Ala Gly Gly Arg Pro Ser Asp Thr Tyr
                20                  25                  30
Gly Ala Pro Gly Gly Gly Asn Gly Gly Arg Pro Ser Asp Ser Tyr Gly
            35                  40                  45
Ala Pro Gly Gln Gly Gln Gly Gln Gly Gln Gly Gln Gly Gly Tyr Gly
        50                  55                  60
Gly Lys Pro Ser Asp Ser Tyr Gly Ala Pro Gly Gly Gly Asn Gly Asn
65                  70                  75                  80
Gly Gly Arg Pro Ser Ser Ser Tyr Gly Ala Pro Gly Gly Gly Asn Gly
                85                  90                  95
Gly Arg Pro Ser Asp Thr Tyr Gly Ala Pro Gly Gly Gly Asn Gly Gly
                100                 105                 110
Arg Pro Ser Asp Thr Tyr Gly Ala Pro Gly Gly Gly Asn Gly Asn
                115                 120                 125
Gly Gly Arg Pro Ser Ser Ser Tyr Gly Ala Pro Gly Gln Gly Gln Gly
            130                 135                 140
Asn Gly Asn Gly Gly Arg Pro Ser Ser Ser Tyr Gly Ala Pro Gly Gly
145                 150                 155                 160
```

Gly Asn Gly Gly Arg Pro Ser Asp Thr Tyr Gly Ala Pro Gly Gly Gly
             165                 170                 175

Asn Gly Gly Arg Pro Ser Asp Thr Tyr Gly Ala Pro Gly Gly Gly Asn
         180                 185                 190

Asn Gly Gly Arg Pro Ser Ser Tyr Gly Ala Pro Gly Gly Gly Asn
         195                 200                 205

Gly Gly Arg Pro Ser Asp Thr Tyr Gly Ala Pro Gly Gly Asn Gly
    210                 215                 220

Asn Gly Ser Gly Gly Arg Pro Ser Ser Tyr Gly Ala Pro Ala Gln
225                 230                 235                 240

Gly Gln Gly Gly Phe Gly Gly Arg Pro Ser Asp Ser Tyr Gly Ala Pro
             245                 250                 255

Gly Gln Asn Gln Lys Pro Ser Asp Ser Tyr Gly Ala Pro Gly Ser Gly
             260                 265                 270

Asn Gly Ser Ala Gly Arg Pro Ser Ser Tyr Gly Ala Pro Gly Ser
         275                 280                 285

Gly Pro Gly Gly Arg Pro Ser Asp Ser Tyr Gly Pro Ala Ser Gly
    290                 295                 300

<210> SEQ ID NO 3
<211> LENGTH: 211
<212> TYPE: PRT
<213> ORGANISM: Drosophila sechellia

<400> SEQUENCE: 3

Gly Lys Pro Ser Asp Ser Tyr Gly Ala Pro Gly Gly Gly Asn Gly Asn
1               5                   10                  15

Gly Gly Arg Pro Ser Ser Tyr Gly Ala Pro Gly Gly Gly Asn Gly
             20                  25                  30

Gly Arg Pro Ser Asp Thr Tyr Gly Ala Pro Gly Gly Gly Asn Gly Gly
             35                  40                  45

Arg Pro Ser Asp Thr Tyr Gly Ala Pro Gly Gly Gly Asn Gly Asn
    50                  55                  60

Gly Gly Arg Pro Ser Ser Tyr Gly Ala Pro Gly Gln Gly Gln Gly
65                  70                  75                  80

Asn Gly Asn Gly Gly Arg Pro Ser Ser Tyr Gly Ala Pro Gly Gly
             85                  90                  95

Gly Asn Gly Gly Arg Pro Ser Asp Thr Tyr Gly Ala Pro Gly Gly Gly
             100                 105                 110

Asn Gly Gly Arg Pro Ser Asp Thr Tyr Gly Ala Pro Gly Gly Gly Asn
         115                 120                 125

Asn Gly Gly Arg Pro Ser Ser Tyr Gly Ala Pro Gly Gly Gly Asn
         130                 135                 140

Gly Gly Arg Pro Ser Asp Thr Tyr Gly Ala Pro Gly Gly Gly Asn Gly
145                 150                 155                 160

Asn Gly Ser Gly Gly Arg Pro Ser Ser Tyr Gly Ala Pro Ala Gln
             165                 170                 175

Gly Gln Gly Gly Phe Gly Gly Arg Pro Ser Asp Ser Tyr Gly Ala Pro
             180                 185                 190

Gly Gln Asn Gln Lys Pro Ser Asp Ser Tyr Gly Ala Pro Gly Ser Gly
             195                 200                 205

Asn Gly Ser
    210

<210> SEQ ID NO 4

<211> LENGTH: 175
<212> TYPE: PRT
<213> ORGANISM: Acromyrmex echinatior

<400> SEQUENCE: 4

```
Phe Gly Glu Asn Arg Gly Asn Gly Gly Lys Pro Ser Thr Ser Tyr Gly
1               5                   10                  15

Val Pro Asp Ser Asn Gly Asn Asn Arg Gly Gly Phe Gly Asn Gly Gly
            20                  25                  30

Ser Glu Gly Arg Pro Ser Thr Ser Tyr Gly Leu Pro Asp Ala Ser Arg
        35                  40                  45

Asn Asn Gly Asn Gly Phe Gly Asn Val Gly Asn Glu Asp Lys Pro Ser
    50                  55                  60

Thr Asn Tyr Gly Ile Pro Ala Asn Gly Asn Lys Val Ser Gly Phe Gly
65                  70                  75                  80

Asn Val Gly Ser Glu Gly Arg Pro Ser Thr Ser Tyr Gly Val Pro Gly
                85                  90                  95

Ala Asn Gly Asn Gln Gly Phe Gly Ser Gly Gly Ile Gly Arg Pro
            100                 105                 110

Ser Thr Ser Tyr Gly Val Pro Gly Val Asn Gly Asn Asn Gly Gly
        115                 120                 125

Phe Glu Asn Val Gly Arg Pro Ser Thr Ser Tyr Gly Thr Pro Asp Ala
    130                 135                 140

Arg Gly Asn Asn Gly Gly Ser Phe Arg Asn Gly Asp Ile Gly Gly Arg
145                 150                 155                 160

Pro Ser Thr Asn Tyr Gly Ile Pro Gly Ala Asn Gly Asn His Gly
                165                 170                 175
```

<210> SEQ ID NO 5
<211> LENGTH: 158
<212> TYPE: PRT
<213> ORGANISM: Aeshna sp.

<400> SEQUENCE: 5

```
Ala Pro Ser Arg Gly Gly Gly His Gly Gly Gly Ser Ile Ser Ser Ser
1               5                   10                  15

Tyr Gly Ala Pro Ser Lys Gly Ser Gly Phe Gly Gly Gly Ser Ile
            20                  25                  30

Ser Ser Ser Tyr Gly Ala Pro Ser Lys Gly Ser Val Gly Gly Val
        35                  40                  45

Ser Ser Ser Tyr Gly Ala Pro Ala Ile Gly Gly Ser Phe Gly Gly
    50                  55                  60

Gly Ser Phe Gly Gly Gly Ser Phe Gly Gly Ser Phe Gly Gly
65                  70                  75                  80

Ala Pro Ser Ser Tyr Gly Ala Pro Ser Ser Tyr Ser Ala Pro
                85                  90                  95

Ser Ser Ser Tyr Gly Ala Pro Ser Lys Gly Ser Gly Phe Gly Ser
            100                 105                 110

Ser Gly Gly Phe Ser Ser Phe Ser Ser Ala Pro Ser Ser Tyr Gly
        115                 120                 125

Ala Pro Ser Ala Ser Tyr Ser Thr Pro Ser Ser Ser Tyr Gly Ala Pro
    130                 135                 140

Ser Ser Gly Gly Phe Gly Ala Gly Gly Gly Phe Ser Ser Gly
145                 150                 155
```

<210> SEQ ID NO 6

<211> LENGTH: 457
<212> TYPE: PRT
<213> ORGANISM: Aeshna sp.

<400> SEQUENCE: 6

```
Glu Pro Pro Val Gly Gly Ser Gln Ser Tyr Leu Pro Pro Ser Ser Ser
1               5                   10                  15

Tyr Gly Ala Pro Ser Ala Gly Thr Gly Phe Gly His Gly Gly Gly Ser
            20                  25                  30

Pro Ser Gln Ser Tyr Gly Ala Pro Ser Phe Gly Gly Ser Val Gly
        35                  40                  45

Gly Gly Ser His Phe Gly Gly Ser His Ser Gly Gly Gly Gly
    50                  55                  60

Gly Tyr Pro Ser Gln Ser Tyr Gly Ala Pro Ser Arg Pro Ser Gly Ser
65                  70                  75                  80

Ser Phe Gln Ala Phe Gly Ala Pro Ser Ser Tyr Gly Ala Pro
                85                  90                  95

Ser Ser Gln Tyr Gly Ala Pro Ser Gly Gly Gly Ser Tyr Ala Ile
            100                 105                 110

Gln Gly Gly Ser Phe Ser Ser Gly Gly Ser Arg Ala Pro Ser Gln Ala
                115                 120                 125

Tyr Gly Ala Pro Ser Asn Asn Ala Gly Leu Ser His Gln Ser Gln Ser
            130                 135                 140

Phe Gly Gly Gly Leu Ser Ser Ser Tyr Gly Ala Pro Ser Ala Gly Phe
145                 150                 155                 160

Gly Gly Gln Ser His Gly Gly Tyr Ser Gln Gly Gly Asn Gly Gly
                165                 170                 175

Gly His Gly Gly Ser Gly Gly Tyr Ser Tyr Gln Ser Phe Gly
            180                 185                 190

Gly Gly Asn Gly Gly Gly His Gly Gly Ser Arg Pro Ser Ser Ser Tyr
        195                 200                 205

Gly Ala Pro Ser Ser Tyr Gly Ala Pro Ser Gly Gly Lys Gly Val
    210                 215                 220

Ser Gly Gly Phe Val Ser Gln Pro Ser Gly Ser Tyr Gly Ala Pro Ser
225                 230                 235                 240

Gln Ser Tyr Gly Ala Pro Ser Arg Gly Gly His Gly Gly Gly Ser
            245                 250                 255

Ile Ser Ser Ser Tyr Gly Ala Pro Ser Lys Gly Ser Gly Phe Gly
        260                 265                 270

Gly Gly Ser Ile Ser Ser Ser Tyr Gly Ala Pro Ser Lys Gly Ser Val
        275                 280                 285

Gly Gly Gly Val Ser Ser Ser Tyr Gly Ala Pro Ala Ile Gly Gly
    290                 295                 300

Ser Phe Gly Gly Gly Ser Phe Gly Gly Ser Phe Gly Gly Ser
305                 310                 315                 320

Phe Gly Gly Gly Ala Pro Ser Ser Ser Tyr Gly Ala Pro Ser Ser Ser
                325                 330                 335

Tyr Ser Ala Pro Ser Ser Tyr Gly Ala Pro Ser Lys Gly Ser Gly
            340                 345                 350

Gly Phe Gly Ser Ser Gly Gly Phe Ser Ser Phe Ser Ala Pro Ser
        355                 360                 365

Ser Ser Tyr Gly Ala Pro Ser Ala Ser Tyr Ser Thr Pro Ser Ser Ser
            370                 375                 380

Tyr Gly Ala Pro Ser Ser Gly Gly Phe Gly Ala Gly Gly Gly Phe Ser
```

```
385                 390                 395                 400

Ser Gly Gly Tyr Ser Gly Gly Gly Gly Tyr Ser Gly Gly Ser
                405                 410                 415

Gly Gly Phe Gly Gly His Gly Gly Ser Gly Gly Ala Gly Gly Tyr Ser
            420                 425                 430

Gly Gly Gly Gly Tyr Ser Gly Gly Gly Ser Gly Gly Gln Lys Tyr
                435                 440                 445

Asp Ser Asn Gly Gly Tyr Val Tyr Ser
    450                 455

<210> SEQ ID NO 7
<211> LENGTH: 162
<212> TYPE: PRT
<213> ORGANISM: Haematobia irritans

<400> SEQUENCE: 7

Ala Gly Gly Gly Asn Gly Gly Gly Thr Gly Gly Thr Pro Ser Ser
1               5                   10                  15

Ser Tyr Gly Ala Pro Ser Asn Gly Gly Ser Asn Gly Asn Gly Phe
                20                  25                  30

Gly Ser Pro Ser Ser Tyr Gly Ala Pro Gly Ser Gly Gly Ser Asn
            35                  40                  45

Gly Asn Gly Gly Arg Pro Ser Leu Ser Tyr Gly Ala Pro Gly Ser
    50                  55                  60

Gly Gly Ser Asn Gly Asn Gly Gly Arg Pro Ser Ser Tyr Gly
65              70                  75                  80

Ala Pro Gly Ala Gly Ser Asn Gly Asn Gly Gly Arg Pro Ser
                85                  90                  95

Ser Ser Tyr Gly Ala Pro Gly Ala Gly Gly Ser Asn Gly Asn Gly Gly
            100                 105                 110

Gly Arg Pro Ser Ser Ser Tyr Gly Ala Pro Gly Ala Gly Gly Ser Asn
            115                 120                 125

Gly Asn Gly Gly Gly Arg Pro Ser Ser Ser Tyr Gly Ala Pro Gly Ala
    130                 135                 140

Gly Gly Ser Asn Gly Asn Gly Gly Ser Arg Pro Ser Ser Thr Tyr Gly
145                 150                 155                 160

Ala Pro

<210> SEQ ID NO 8
<211> LENGTH: 580
<212> TYPE: PRT
<213> ORGANISM: Haematobia irritans

<400> SEQUENCE: 8

Arg Pro Glu Pro Pro Val Asn Ser Tyr Leu Pro Pro Leu Asn Asn
1               5                   10                  15

Tyr Gly Ala Pro Gly Ala Gly Gly Ser Ser Asp Gly Ser Pro Leu
                20                  25                  30

Ala Pro Ser Asp Ala Tyr Gly Ala Pro Asp Leu Gly Gly Ser Gly
            35                  40                  45

Gly Ser Gly Gln Gly Pro Ser Ser Tyr Gly Ala Pro Gly Leu Gly
    50                  55                  60

Gly Gly Asn Gly Gly Ala Pro Ser Ser Tyr Gly Ala Pro Gly Leu
65              70                  75                  80

Gly Gly Gly Asn Gly Gly Ser Arg Arg Pro Ser Ser Tyr Gly Ala
                85                  90                  95
```

```
Pro Gly Ala Gly Gly Gly Asn Gly Gly Gly Thr Gly Thr Pro
            100                 105                 110
Ser Ser Ser Tyr Gly Ala Pro Ser Asn Gly Gly Ser Asn Gly Asn
        115                 120                 125
Gly Phe Gly Ser Pro Ser Ser Tyr Gly Ala Pro Gly Ser Gly Gly
    130                 135                 140
Ser Asn Gly Asn Gly Gly Arg Pro Ser Leu Ser Tyr Gly Ala Pro
145                 150                 155                 160
Gly Ser Gly Gly Ser Asn Gly Asn Gly Gly Arg Pro Ser Ser Ser
                165                 170                 175
Tyr Gly Ala Pro Gly Ala Gly Ser Asn Gly Asn Gly Gly Arg
            180                 185                 190
Pro Ser Ser Ser Tyr Gly Ala Pro Ala Gly Gly Ser Asn Gly Asn
        195                 200                 205
Gly Gly Gly Arg Pro Ser Ser Tyr Gly Ala Pro Gly Ala Gly Gly
    210                 215                 220
Ser Asn Gly Asn Gly Gly Arg Pro Ser Ser Ser Tyr Gly Ala Pro
225                 230                 235                 240
Gly Ala Gly Gly Ser Asn Gly Asn Gly Gly Ser Arg Pro Ser Ser Thr
                245                 250                 255
Tyr Gly Ala Pro Gly Ala Gly Gly Ser Asn Gly Asn Gly Cys Gly Asn
            260                 265                 270
Lys Pro Ser Ser Ser Tyr Gly Ala Pro Ser Ala Gly Ser Asn Gly Asn
        275                 280                 285
Gly Gly Ser Glu Gln Gly Ser Ser Gly Ser Pro Ser Asp Ser Tyr Gly
    290                 295                 300
Pro Pro Ala Ser Gly Thr Gly Arg Gly Arg Asn Gly Gly Gly Gly
305                 310                 315                 320
Ala Gly Gly Gly Arg Arg Gly Gln Pro Asn Gln Glu Tyr Leu Pro Pro
                325                 330                 335
Asn Gln Gly Asp Asn Gly Asn Asn Gly Gly Ser Gly Gly Asp Asp Gly
            340                 345                 350
Tyr Asp Tyr Ser Gln Ser Gly Asp Gly Gly Gln Gly Gly Ser Gly
        355                 360                 365
Gly Ser Gly Asn Gly Gly Asp Asp Gly Ser Asn Ile Val Glu Tyr Glu
    370                 375                 380
Ala Gly Gln Glu Gly Tyr Arg Pro Gln Ile Arg Tyr Glu Gly Glu Ala
385                 390                 395                 400
Asn Glu Gly Gly Gln Gly Ser Gly Gly Ala Gly Gly Ser Asp Gly Thr
                405                 410                 415
Asp Gly Tyr Glu Tyr Glu Gln Asn Gly Gly Asp Gly Gly Ala Gly Gly
            420                 425                 430
Ser Gly Gly Pro Gly Thr Gly Gln Asp Leu Gly Glu Asn Gly Tyr Ser
        435                 440                 445
Ser Gly Arg Pro Gly Gly Asp Asn Gly Gly Gly Gly Tyr Ser Asn
    450                 455                 460
Gly Asn Gly Gln Gly Asp Gly Gly Gln Asp Leu Gly Ser Asn Gly Tyr
465                 470                 475                 480
Ser Ser Gly Ala Pro Asn Gly Gln Asn Gly Gly Arg Arg Asn Gly Gly
                485                 490                 495
Gly Gln Asn Asn Asn Gly Gln Gly Tyr Ser Ser Gly Arg Pro Asn Gly
            500                 505                 510
```

```
Asn Gly Ser Gly Gly Arg Asn Gly Asn Gly Gly Arg Gly Asn Gly Gly
            515                 520                 525

Gly Tyr Arg Asn Gly Asn Gly Asn Gly Gly Asn Gly Asn Gly Ser
        530                 535                 540

Gly Ser Gly Ser Gly Asn Asn Gly Tyr Asn Tyr Asp Gln Gln Gly Ser
545                 550                 555                 560

Asn Gly Phe Gly Ala Gly Gly Gln Asn Gly Glu Asn Asp Gly Ser Gly
                565                 570                 575

Tyr Arg Tyr Ser
            580

<210> SEQ ID NO 9
<211> LENGTH: 256
<212> TYPE: PRT
<213> ORGANISM: Ctenocephalides felis

<400> SEQUENCE: 9

Ala Asn Gly Asn Gly Phe Glu Gly Ala Ser Asn Gly Leu Ser Ala Thr
1               5                   10                  15

Tyr Gly Ala Pro Asn Gly Gly Phe Gly Gly Asn Gly Asn Gly Gly
            20                  25                  30

Ala Pro Ser Ser Ser Tyr Gly Ala Pro Gly Ala Gly Asn Gly Gly Asn
        35                  40                  45

Gly Gly Gly Arg Pro Ser Ser Ser Tyr Gly Ala Pro Gly Ala Gly Gly
50                  55                  60

Ser Gly Asn Gly Phe Gly Gly Arg Pro Ser Ser Ser Tyr Gly Ala Pro
65                  70                  75                  80

Gly Asn Gly Asn Gly Ala Asn Gly Gly Arg Gly Gly Arg Pro Ser Ser
                85                  90                  95

Arg Tyr Gly Ala Pro Gly Asn Gly Asn Gly Asn Gly Asn Gly Asn Gly
            100                 105                 110

Gly Arg Pro Ser Ser Ser Tyr Gly Ala Pro Gly Ser Asn Gly Asn Gly
        115                 120                 125

Gly Arg Pro Ser Ser Ser Tyr Gly Ala Pro Gly Ser Gly Asn Gly Phe
    130                 135                 140

Gly Gly Asn Gly Gly Arg Pro Ser Ser Ser Tyr Gly Ala Pro Gly Ala
145                 150                 155                 160

Asn Gly Asn Gly Asn Gly Gly Ala Ile Gly Gln Pro Ser Ser Ser Tyr
                165                 170                 175

Gly Ala Pro Gly Gln Asn Gly Asn Gly Gly Leu Ser Ser Thr Tyr
            180                 185                 190

Gly Ala Pro Gly Ala Gly Asn Gly Gly Phe Gly Gly Asn Gly Gly Gly
        195                 200                 205

Leu Ser Ser Thr Tyr Gly Ala Pro Gly Ser Gly Asn Gly Gly Phe Gly
    210                 215                 220

Gly Asn Gly Leu Ser Ser Thr Tyr Gly Ala Pro Gly Ser Gly Asn Gly
225                 230                 235                 240

Gly Phe Gly Gly Asn Gly Gly Gly Leu Ser Ser Thr Tyr Gly Ala Pro
                245                 250                 255

<210> SEQ ID NO 10
<211> LENGTH: 146
<212> TYPE: PRT
<213> ORGANISM: Ctenocephalides felis

<400> SEQUENCE: 10
```

Pro Gly Gly Ala Gly Ala Gly Gly Tyr Pro Gly Gly Ala Gly Gly
1               5                   10                  15

Ala Gly Gly Ala Gly Gly Tyr Pro Gly Gly Ser Ala Gly Gly Ala Gly
            20                  25                  30

Gly Tyr Pro Gly Gly Ser Gly Ser Gly Val Gly Gly Tyr Pro Gly Gly
        35                  40                  45

Ser Asn Gly Gly Ala Gly Gly Tyr Pro Gly Gly Ser Asn Gly Gly Ala
50                  55                  60

Gly Gly Tyr Pro Gly Gly Ser Asn Gly Gly Ala Gly Gly Tyr Pro Gly
65              70                  75                  80

Gly Ser Asn Gly Gly Ala Gly Gly Tyr Pro Gly Gly Ser Asn Gly Asn
            85                  90                  95

Gly Gly Tyr Ser Asn Gly Gly Ser Asn Gly Gly Ala Gly Gly Tyr
                100                 105                 110

Pro Gly Gly Ser Asn Gly Asn Gly Tyr Pro Gly Ser Gly Ser Asn
            115                 120                 125

Gly Gly Ala Gly Gly Tyr Pro Gly Gly Ser Asn Gly Asn Gly Gly Tyr
    130                 135                 140

Pro Gly
145

<210> SEQ ID NO 11
<211> LENGTH: 201
<212> TYPE: PRT
<213> ORGANISM: Bombus terrestris

<400> SEQUENCE: 11

Phe Asp Gly Gln Asn Gly Ile Gly Gly Asp Ser Gly Arg Asn Gly
1               5                   10                  15

Leu Ser Asn Ser Tyr Gly Val Pro Gly Ser Asn Gly Gly Arg Asn Gly
            20                  25                  30

Asn Gly Arg Gly Asn Gly Phe Gly Gly Gln Pro Ser Ser Ser Tyr
        35                  40                  45

Gly Ala Pro Ser Asn Gly Leu Gly Gly Asn Gly Gly Ser Gly Ala Gly
50                  55                  60

Arg Pro Ser Ser Ser Tyr Gly Ala Pro Gly Gly Gly Asn Gly Phe Gly
65                  70                  75                  80

Gly Gly Gln Pro Ser Ser Ser Tyr Gly Ala Pro Ser Asn Gly Leu Gly
            85                  90                  95

Gly Asn Gly Ala Gly Arg Pro Ser Ser Ser Tyr Gly Ala Pro Gly Gly
            100                 105                 110

Gly Asn Gly Phe Gly Gly Gly Ser Asn Gly Ala Gly Lys Asn Gly Phe
            115                 120                 125

Gly Gly Ala Pro Ser Asn Ser Tyr Gly Pro Pro Glu Asn Gly Asn Gly
    130                 135                 140

Phe Gly Gly Asn Gly Gly Ser Pro Ser Gly Leu Tyr Gly Pro
145                 150                 155                 160

Pro Gly Arg Asn Gly Gly Asn Gly Gly Asn Gly Gly Asn Gly Asn
            165                 170                 175

Gly Gly Arg Pro Ser Ser Ser Tyr Gly Thr Pro Glu Arg Asn Gly Gly
        180                 185                 190

Arg Pro Ser Gly Leu Tyr Gly Pro Pro
        195                 200

<210> SEQ ID NO 12

```
<211> LENGTH: 183
<212> TYPE: PRT
<213> ORGANISM: Tribolium castaneum

<400> SEQUENCE: 12

Asn Gly Phe Gly Gly Gln Asn Gly Arg Leu Ser Ser Thr Tyr
1               5                   10                  15

Gly Pro Pro Gly Gln Gly Gly Asn Gly Phe Gly Gly Gln Asn Gly
            20                  25                  30

Gly Arg Pro Ser Ser Thr Tyr Gly Pro Pro Gly Gln Gly Asn Gly
        35                  40                  45

Phe Gly Gly Gln Asn Gly Gly Arg Pro Ser Ser Thr Tyr Gly Pro
50                  55                  60

Pro Gly Gln Gly Gly Asn Gly Phe Gly Gly Gln Asn Gly Gly Arg
65                  70                  75                  80

Pro Ser Ser Thr Tyr Gly Pro Pro Gly Gln Gly Gly Asn Gly Phe Gly
            85                  90                  95

Gly Gly Gln Asn Gly Gly Arg Pro Ser Ser Thr Tyr Gly Pro Pro Gly
                100                 105                 110

Gln Gly Gly Asn Gly Phe Gly Gly Gln Asn Gly Gly Arg Pro Ser
        115                 120                 125

Ser Thr Tyr Gly Pro Pro Gly Gln Gly Gly Asn Gly Phe Gly Gly Gly
    130                 135                 140

Gln Asn Gly Gly Lys Pro Ser Ser Thr Tyr Gly Pro Pro Gly Gln Gly
145                 150                 155                 160

Gly Asn Gly Phe Gly Gly Gly Gln Asn Gly Gly Arg Pro Ser Ser Thr
                165                 170                 175

Tyr Gly Pro Pro Gly Gln Gly
            180

<210> SEQ ID NO 13
<211> LENGTH: 551
<212> TYPE: PRT
<213> ORGANISM: Tribolium castaneum

<400> SEQUENCE: 13

Arg Ala Glu Pro Pro Val Asn Ser Tyr Leu Pro Ser Gln Asn Gly
1               5                   10                  15

Gly Pro Ser Ser Thr Tyr Gly Pro Pro Gly Phe Gln Pro Gly Thr Pro
            20                  25                  30

Leu Gly Gly Gly Asn Gly Gly His Pro Ser Gln Gly Gly Asn
        35                  40                  45

Gly Gly Phe Gly Gly Arg His Pro Asp Ser Asp Gln Arg Pro Gly Thr
50                  55                  60

Ser Tyr Leu Pro Pro Gly Gln Asn Gly Gly Ala Gly Arg Pro Gly Val
65                  70                  75                  80

Thr Tyr Gly Pro Pro Gly Gln Gly Gly Gly Gln Asn Gly Gly Pro
            85                  90                  95

Ser Ser Thr Tyr Gly Pro Pro Gly Gln Gly Asn Gly Phe Gly Gly
                100                 105                 110

Gly Gln Asn Gly Gly Arg Leu Ser Ser Thr Tyr Gly Pro Pro Gly Gln
        115                 120                 125

Gly Gly Asn Gly Phe Gly Gly Gln Asn Gly Gly Arg Pro Ser Ser
    130                 135                 140

Thr Tyr Gly Pro Pro Gly Gln Gly Gly Asn Gly Phe Gly Gly Gly Gln
145                 150                 155                 160
```

```
Asn Gly Gly Arg Pro Ser Ser Thr Tyr Gly Pro Gly Gln Gly Gly
            165                 170                 175

Asn Gly Phe Gly Gly Gln Asn Gly Gly Arg Pro Ser Ser Thr Tyr
        180                 185                 190

Gly Pro Pro Gly Gln Gly Gly Asn Gly Phe Gly Gly Gln Asn Gly
            195                 200                 205

Gly Arg Pro Ser Ser Thr Tyr Gly Pro Pro Gly Gln Gly Gly Asn
    210                 215                 220

Phe Gly Gly Gln Asn Gly Gly Arg Pro Ser Ser Thr Tyr Gly Pro
225                 230                 235                 240

Pro Gly Gln Gly Gly Asn Gly Phe Gly Gly Gln Asn Gly Gly Lys
            245                 250                 255

Pro Ser Ser Thr Tyr Gly Pro Pro Gly Gln Gly Gly Asn Gly Phe
            260                 265                 270

Gly Gly Gln Asn Gly Gly Arg Pro Ser Ser Thr Tyr Gly Pro Gly
        275                 280                 285

Gln Gly Gly Asn Gly Asn Gly Gly His Asn Gly Gln Arg Pro Gly
            290                 295                 300

Gly Ser Tyr Leu Pro Pro Ser Gln Gly Gly Asn Gly Gly Tyr Pro Ser
305                 310                 315                 320

Gly Gly Pro Gly Gly Tyr Pro Ser Gly Gly Pro Gly Gly Asn Gly Gly
            325                 330                 335

Tyr Gly Gly Glu Glu Ser Thr Glu Pro Ala Lys Tyr Glu Phe Glu
            340                 345                 350

Tyr Gln Val Asp Asp Glu His Asn Thr His Phe Gly His Gln Glu
        355                 360                 365

Ser Arg Asp Gly Asp Lys Ala Thr Gly Glu Tyr Asn Val Leu Leu Pro
    370                 375                 380

Asp Gly Arg Lys Gln Val Val Gln Tyr Glu Ala Asp Ser Glu Gly Tyr
385                 390                 395                 400

Lys Pro Lys Ile Ser Tyr Glu Gly Gly Asn Gly Asn Gly Gly Tyr Pro
            405                 410                 415

Ser Gly Gly Pro Gly Gly Ala Gly Asn Gly Gly Tyr Pro Ser Gly Gly
            420                 425                 430

Pro Gln Gly Gly Asn Gly Gly Tyr Pro Ser Gly Gly Pro Gln Gly Gly
            435                 440                 445

Asn Gly Gly Tyr Pro Ser Gly Gly Pro Gln Gly Gly Asn Gly Gly Tyr
    450                 455                 460

Pro Ser Gly Gly Pro Gln Gly Gly Asn Gly Gly Tyr Pro Ser Gly Gly
465                 470                 475                 480

Pro Gln Gly Gly Asn Gly Gly Tyr Pro Ser Gly Gly Pro Gln Gly Gly
            485                 490                 495

Asn Gly Gly Tyr Pro Ser Gly Gly Pro Gln Gly Gly Asn Gly Gly Tyr
            500                 505                 510

Pro Ser Gly Gly Pro Gln Gly Gly Asn Gly Gly Tyr Thr Ser Gly Gly
        515                 520                 525

Pro Gln Gly Gly Asn Gly Gly Tyr Pro Ser Gly Gly Pro Gln Gly Gly
            530                 535                 540

Asn Gly Gly Ser Gly Pro Tyr
545                 550

<210> SEQ ID NO 14
<211> LENGTH: 444
```

<212> TYPE: PRT
<213> ORGANISM: Tribolium castaneum

<400> SEQUENCE: 14

```
Gln Leu Thr Lys Arg Asp Ala Pro Leu Ser Gly Gly Tyr Pro Ser Gly
1               5                   10                  15

Gly Pro Ala Asn Ser Tyr Leu Pro Pro Gly Gly Ala Ser Gln Pro Ser
            20                  25                  30

Gly Asn Tyr Gly Ala Pro Ser Gly Gly Phe Gly Lys Ser Gly Gly
        35                  40                  45

Phe Gly Gly Ser Gly Gly Phe Gly Gly Ala Pro Ser Gln Ser Tyr Gly
    50                  55                  60

Ala Pro Ser Gly Gly Phe Gly Gly Ser Ser Phe Gly Lys Ser Gly
65                  70                  75                  80

Gly Phe Gly Gly Ala Pro Ser Gln Ser Tyr Gly Ala Pro Ser Gly Gly
                85                  90                  95

Phe Gly Gly Ser Ser Ser Phe Gly Lys Ser Gly Gly Phe Gly Gly
                100                 105                 110

Ala Pro Ser Gln Ser Tyr Gly Ala Pro Ser Gly Gly Phe Gly Gly Ser
            115                 120                 125

Ser Ser Phe Gly Lys Ser Gly Gly Phe Gly Gly Ala Pro Ser Gln Ser
        130                 135                 140

Tyr Gly Ala Pro Ser Gly Gly Phe Gly Gly Ser Ser Phe Gly Lys
145                 150                 155                 160

Ser Gly Gly Phe Gly Gly Ala Pro Ser Gln Ser Tyr Gly Ala Pro Ser
                165                 170                 175

Gly Gly Phe Gly Gly Lys Ser Ser Ser Phe Ser Ser Ala Pro Ser Gln
                180                 185                 190

Ser Tyr Gly Ala Pro Ser Gly Gly Phe Gly Gly Lys Ser Gly Gly Phe
            195                 200                 205

Gly Gly Ala Pro Ser Gln Ser Tyr Gly Ala Pro Ser Gly Gly Phe Gly
        210                 215                 220

Gly Lys Ser Gly Gly Phe Gly Gly Ala Pro Ser Gln Ser Tyr Gly Ala
225                 230                 235                 240

Pro Ser Gly Gly Phe Gly Gly Ser Ser Ser Phe Gly Lys Ser Gly Gly
                245                 250                 255

Phe Gly Gly Ala Pro Ser Gln Ser Tyr Gly Ala Pro Ser Gly Gly Phe
                260                 265                 270

Gly Gly Ser Ser Ser Phe Gly Lys Ser Gly Phe Gly His Gly Ser
            275                 280                 285

Gly Ala Pro Ser Gln Ser Tyr Gly Ala Pro Ser Arg Ser Gln Pro Gln
        290                 295                 300

Ser Asn Tyr Leu Pro Pro Ser Thr Ser Tyr Gly Thr Pro Val Ser Ser
305                 310                 315                 320

Ala Lys Ser Ser Gly Ser Phe Gly Gly Ala Pro Ser Gln Ser Tyr Gly
                325                 330                 335

Ala Pro Ser Gln Ser His Ala Pro Ser Gln Ser Tyr Gly Ala Pro Ser
            340                 345                 350

Arg Ser Phe Ser Gln Ala Pro Ser Gln Ser Tyr Gly Ala Pro Ser Gln
        355                 360                 365

Gly His Ala Pro Ala Pro Gln Gln Ser Tyr Ser Ala Pro Ser Gln Ser
        370                 375                 380

Tyr Gly Ala Pro Ser Gly Gly Phe Gly Gly His Gly Gly Phe Gly
385                 390                 395                 400
```

```
Gly Gln Gly Gln Gly Phe Gly Gly Arg Ser Gln Pro Ser Gln Ser
                405                 410                 415

Tyr Gly Ala Pro Ala Pro Ser Gln Ser Tyr Gly Ala Pro Ser Ala Gly
            420                 425                 430

Gly Gln Gln Tyr Ala Ser Asn Gly Gly Tyr Ser Tyr
        435                 440

<210> SEQ ID NO 15
<211> LENGTH: 426
<212> TYPE: PRT
<213> ORGANISM: Apis mellifera

<400> SEQUENCE: 15

Arg Ser Glu Pro Pro Val Asn Ser Tyr Leu Pro Pro Ser Gly Asn Gly
1               5                   10                  15

Asn Gly Gly Gly Gly Gly Ser Ser Asn Val Tyr Gly Pro Pro Gly
            20                  25                  30

Phe Asp Gly Gln Asn Gly Ile Gly Glu Gly Asp Asn Gly Arg Asn Gly
        35                  40                  45

Ile Ser Asn Ser Tyr Gly Val Pro Thr Gly Asn Gly Tyr Asn Gly
    50                  55                  60

Asp Ser Ser Gly Asn Gly Arg Pro Gly Thr Asn Gly Gly Arg Asn Gly
65                  70                  75                  80

Asn Gly Asn Gly Arg Gly Asn Gly Tyr Gly Gly Gln Pro Ser Asn
                85                  90                  95

Ser Tyr Gly Pro Pro Ser Asn Gly His Gly Asn Gly Ala Gly Arg
            100                 105                 110

Pro Ser Ser Ser Tyr Gly Ala Pro Gly Gly Asn Gly Phe Ala Gly
            115                 120                 125

Gly Ser Asn Gly Lys Asn Gly Phe Gly Gly Pro Ser Ser Ser Tyr
    130                 135                 140

Gly Pro Pro Glu Asn Gly Asn Gly Phe Asn Gly Gly Asn Gly Gly Pro
145                 150                 155                 160

Ser Gly Leu Tyr Gly Pro Pro Gly Arg Asn Gly Gly Asn Gly Gly Asn
                165                 170                 175

Gly Gly Asn Gly Gly Arg Pro Ser Gly Ser Tyr Gly Thr Pro Glu Arg
            180                 185                 190

Asn Gly Gly Arg Leu Gly Gly Leu Tyr Gly Ala Pro Gly Arg Asn Gly
            195                 200                 205

Asn Asn Gly Gly Asn Gly Tyr Pro Ser Gly Gly Leu Asn Gly Gly Asn
        210                 215                 220

Gly Gly Tyr Pro Ser Gly Gly Pro Gly Asn Gly Ala Asn Gly Gly
225                 230                 235                 240

Tyr Pro Ser Gly Gly Ser Asn Gly Asp Asn Gly Gly Tyr Pro Ser Gly
                245                 250                 255

Gly Pro Asn Gly Asn Gly Asn Gly Asn Gly Gly Tyr Gly Gln Asp Glu
            260                 265                 270

Asn Asn Glu Pro Ala Lys Tyr Glu Phe Ser Tyr Glu Val Lys Asp Glu
        275                 280                 285

Gln Ser Gly Ala Asp Tyr Gly His Thr Glu Ser Arg Asp Gly Asp Arg
    290                 295                 300

Ala Gln Gly Glu Phe Asn Val Leu Leu Pro Asp Gly Arg Lys Gln Ile
305                 310                 315                 320

Val Glu Tyr Glu Ala Asp Gln Asp Gly Phe Lys Pro Gln Ile Arg Tyr
```

```
            325                 330                 335
Glu Gly Glu Ala Asn Ser Gln Gly Tyr Gly Ser Gly Gly Pro Gly Gly
            340                 345                 350

Asn Gly Gly Asp Asn Gly Tyr Pro Ser Gly Gly Pro Gly Gly Asn Gly
            355                 360                 365

Tyr Ser Ser Gly Arg Pro Asn Gly Gly Ser Asp Phe Ser Asp Gly Gly
            370                 375                 380

Tyr Pro Ser Thr Arg Pro Gly Gly Glu Asn Gly Gly Tyr Arg Asn Gly
385                 390                 395                 400

Asn Asn Gly Gly Asn Gly Asn Gly Gly Tyr Pro Ser Gly Asn Gly Gly
                    405                 410                 415

Asp Ala Ala Ala Asn Gly Gly Tyr Gln Tyr
            420                 425

<210> SEQ ID NO 16
<211> LENGTH: 318
<212> TYPE: PRT
<213> ORGANISM: Apis mellifera

<400> SEQUENCE: 16

Asp Ala Pro Ile Ser Gly Ser Tyr Leu Pro Ser Thr Ser Tyr Gly
1               5                   10                  15

Thr Pro Asn Leu Gly Gly Gly Pro Ser Ser Thr Tyr Gly Ala Pro
            20                  25                  30

Ser Gly Gly Gly Gly Arg Pro Ser Ser Tyr Gly Ala Pro Ser
            35                  40                  45

Ser Thr Tyr Gly Ala Pro Ser Ser Thr Tyr Gly Ala Pro Ser Asn Gly
            50                  55                  60

Gly Gly Arg Pro Ser Ser Thr Tyr Gly Ala Pro Ser Asn Gly Gly
65                  70                  75                  80

Arg Pro Ser Ser Ser Tyr Gly Ala Pro Ser Ser Ser Tyr Gly Ala Pro
                    85                  90                  95

Ser Ser Thr Tyr Gly Ala Pro Ser Asn Gly Gly Arg Pro Ser Ser
            100                 105                 110

Ser Tyr Gly Ala Pro Ser Phe Gly Gly Gly Gly Phe Gly Gly Gly
            115                 120                 125

Asn Gly Leu Ser Thr Ser Tyr Gly Ala Pro Ser Arg Gly Gly Gly Gly
            130                 135                 140

Gly Gly Gly Ser Ile Ser Ser Ser Tyr Gly Ala Pro Thr Gly Gly Gly
145                 150                 155                 160

Gly Gly Gly Pro Ser Thr Thr Tyr Gly Ala Pro Asn Gly Gly Asn
            165                 170                 175

Gly Tyr Ser Arg Pro Ser Ser Thr Tyr Gly Thr Pro Ser Thr Gly Gly
            180                 185                 190

Gly Ser Phe Gly Gly Ser Gly Gly Tyr Ser Gly Gly Gly Gly Tyr
            195                 200                 205

Ser Gly Gly Gly Asn Gly Tyr Ser Gly Gly Gly Gly Gly Tyr Ser
            210                 215                 220

Gly Gly Asn Gly Gly Tyr Ser Gly Gly Asn Gly Gly Tyr
225                 230                 235                 240

Ser Gly Gly Asn Gly Gly Gly Tyr Ser Gly Gly Gly Gly Gly Tyr
                    245                 250                 255

Ser Gly Gly Gly Gly Gly Gly Tyr Ser Gly Gly Asn Gly Tyr Ser
            260                 265                 270
```

```
Gly Gly Gly Gly Gly Tyr Ser Gly Gly Asn Gly Tyr Ser Gly
                275             280             285

Gly Asn Gly Gly Tyr Ser Gly Gly Gly Gly Tyr Ser Gly Gly
    290             295             300

Gly Gly Gly Gln Ser Tyr Ala Ser Asn Gly Gly Tyr Gln Tyr
305             310             315

<210> SEQ ID NO 17
<211> LENGTH: 747
<212> TYPE: PRT
<213> ORGANISM: Nasonia vitripennis

<400> SEQUENCE: 17

Arg Pro Glu Pro Pro Val Asn Ser Tyr Leu Pro Gly Gln Gly Gly
1               5                   10                  15

Gly Phe Gly Gly Gly Arg Pro Ser Gly Ala Ser Pro Ser Asp Gln Tyr
            20                  25                  30

Gly Pro Pro Asp Phe Gln Gly Ala Gly Gly Arg Gly Gly Gln Ala Ala
        35                  40                  45

Gly Gly Asn Phe Gly Gly Gly Asn Gly Phe Gly Gly Ala Pro Ser
    50                  55                  60

Ser Ser Tyr Gly Pro Pro Gly Phe Gly Ser Asn Glu Pro Asn Lys Phe
65                  70                  75                  80

Ser Gly Ala Gly Gly Gly Ala Gly Arg Pro Gln Asp Ser Tyr Gly
                85                  90                  95

Pro Pro Ala Gly Gly Asn Gly Phe Ala Gly Ser Ala Gly Ala Gly Asn
            100                 105                 110

Ser Gly Arg Pro Gly Gly Ala Ala Ala Gly Gly Arg Pro Ser Asp Ser
        115                 120                 125

Tyr Gly Pro Pro Gln Gly Gly Ser Gly Phe Gly Gly Gly Asn Ala
    130                 135                 140

Gly Arg Pro Ser Asp Ser Tyr Gly Pro Pro Ser Ala Gly Gly Gly Gly
145                 150                 155                 160

Phe Gly Gly Gly Ser Pro Gly Gly Gly Phe Gly Gly Ser Pro Gly
                165                 170                 175

Gly Gly Phe Gly Gly Gly Asn Gln Gly Ala Pro Gln Ser Ser Tyr Gly
            180                 185                 190

Pro Pro Ala Ser Gly Phe Gly Gln Gly Gly Ala Gly Gln Gly Arg
        195                 200                 205

Pro Ser Asp Ser Tyr Gly Pro Pro Gly Gly Gly Ser Gly Gly Arg Pro
    210                 215                 220

Ser Gln Gly Gly Asn Gly Phe Gly Gly Asn Ala Gly Arg Pro Ser
225                 230                 235                 240

Asp Ser Tyr Gly Pro Pro Ala Ala Gly Gly Gly Phe Gly Gly Asn
                245                 250                 255

Ala Gly Gly Asn Gly Gly Asn Gly Phe Gly Gly Gly Arg Pro Ser
            260                 265                 270

Gly Ser Pro Gly Gly Phe Gly Gly Gln Gly Gly Gly Arg Pro Ser
        275                 280                 285

Asp Ser Tyr Leu Pro Pro Ser Gly Gly Ser Gly Phe Gly Gly Asn
    290                 295                 300

Gly Arg Gln Pro Gly Gly Phe Gly Gln Gly Gly Asn Gly Ala Gly
305                 310                 315                 320

Gln Gln Asn Gly Gly Gly Gly Ala Gly Arg Pro Ser Ser Ser Tyr Gly
                325                 330                 335
```

```
Pro Pro Ser Asn Gly Asn Gly Gly Phe Ser Gly Gln Asn Gly Gly
            340                 345                 350
Arg Gly Ser Pro Ser Gly Gly Gly Phe Gly Gly Ala Gly Gly Ser
            355                 360                 365
Pro Ser Ser Ser Tyr Gly Pro Pro Ala Gly Gly Ser Gly Phe Gly Asn
            370                 375                 380
Asn Gly Gly Ala Gly Gly Arg Pro Ser Ser Tyr Gly Pro Pro Ser
385                 390                 395                 400
Ser Gly Gly Asn Gly Phe Gly Ser Gly Gln Gly Gly Gln Gly Gly
            405                 410                 415
Gln Gly Gly Gln Gly Gly Arg Pro Ser Ser Tyr Gly Pro Pro Ser
            420                 425                 430
Asn Gly Asn Gly Gly Phe Gly Gly Asn Gly Gly Arg Pro Ser Ser
            435                 440                 445
Asn Gly Tyr Pro Gln Gly Gln Gly Asn Gly Asn Gly Phe Gly Gly
            450                 455                 460
Gln Gly Gly Asn Gly Gly Arg Pro Ser Ser Ser Tyr Gly Pro Pro Gly
465                 470                 475                 480
Gly Asp Ser Gly Tyr Pro Ser Gly Gly Pro Ser Gly Asn Phe Gly Gly
            485                 490                 495
Ser Asn Ala Gly Gly Gly Gly Gly Phe Gly Gly Gln Val Gln Asp
            500                 505                 510
Ser Tyr Gly Pro Pro Ser Gly Ala Val Asn Gly Asn Gly Asn Gly
            515                 520                 525
Tyr Ser Ser Gly Gly Pro Gly Asn Gly Leu Asp Glu Gly Asn Asp
            530                 535                 540
Glu Pro Ala Lys Tyr Glu Phe Ser Tyr Glu Val Lys Asp Asp Gln Ser
545                 550                 555                 560
Asp Gly Arg Lys Gln Ile Val Glu Tyr Glu Ala Asp Gln Asp Gly Phe
            565                 570                 575
Lys Pro Gln Ile Arg Tyr Glu Gly Glu Ala Asn Thr Gly Ala Gly Gly
            580                 585                 590
Ala Gly Gly Tyr Pro Ser Gly Gly Gly Gly Asp Ser Gly Tyr Pro Ser
            595                 600                 605
Gly Pro Ser Gly Ala Gly Gly Asn Ala Gly Tyr Pro Ser Gly Gly Gly
            610                 615                 620
Gly Gly Ala Gly Gly Phe Gly Gly Asn Gly Gly Ser Asn Gly Tyr
625                 630                 635                 640
Pro Ser Gly Gly Pro Ser Gly Gly Gln Gly Gln Phe Gly Gly Gln Gln
            645                 650                 655
Gly Gly Asn Gly Gly Tyr Pro Ser Gly Pro Gln Gly Gly Ser Gly Phe
            660                 665                 670
Gly Gly Gly Ser Gln Gly Ser Gly Ser Gly Tyr Pro Ser Gly Gly
            675                 680                 685
Pro Gly Gly Asn Gly Gly Asn Asn Phe Gly Gly Asn Ala Gly
            690                 695                 700
Tyr Pro Ser Gly Gly Pro Ser Gly Gly Asn Gly Phe Asn Gln Gly Gly
705                 710                 715                 720
Gln Asn Gln Gly Gly Ser Gly Gly Gly Tyr Pro Ser Gly Ser Gly Gly
            725                 730                 735
Asp Ala Ala Ala Asn Gly Gly Tyr Gln Tyr Ser
            740                 745
```

<210> SEQ ID NO 18
<211> LENGTH: 419
<212> TYPE: PRT
<213> ORGANISM: Nasonia vitripennis

<400> SEQUENCE: 18

```
Arg Ala Glu Ala Pro Ile Ser Gly Asn Tyr Leu Pro Pro Ser Thr Ser
1               5                   10                  15
Tyr Gly Thr Pro Asn Leu Gly Gly Gly Gly Gly Gly Gly Gly Gly Phe
            20                  25                  30
Gly Gly Gly Ala Pro Ser Ser Ser Tyr Gly Ala Pro Ser Ser Gly Gly
        35                  40                  45
Gly Phe Gly Gly Ser Phe Gly Gly Ala Pro Ser Ser Ser Tyr Gly
    50                  55                  60
Ala Pro Ser Thr Gly Gly Ser Phe Gly Gly Ala Pro Ser Ser Ser
65                  70                  75                  80
Tyr Gly Ala Pro Ser Ser Gly Gly Ser Phe Gly Gly Ser Phe Gly Gly
            85                  90                  95
Gly Ala Pro Ser Ser Ser Tyr Gly Ala Pro Ser Phe Gly Gly Asn Ala
            100                 105                 110
Pro Ser Ser Ser Tyr Gly Ala Pro Ala Gly Gly Ser Phe Gly Gly
            115                 120                 125
Gly Ala Pro Ser Asn Ser Tyr Gly Pro Pro Ser Ser Tyr Gly Ala
            130                 135                 140
Pro Ser Ala Gly Gly Ser Phe Gly Gly Ser Ser Gly Gly Ser Phe Gly
145                 150                 155                 160
Gly Ser Phe Gly Gly Gly Ala Pro Ser Ser Ser Tyr Gly Ala Pro Ala
            165                 170                 175
Pro Ser Arg Pro Ser Ser Asn Tyr Gly Ala Pro Ser Arg Pro Ser Ser
            180                 185                 190
Asn Tyr Gly Ala Pro Ser Ser Gly Gly Ser Gly Phe Gly Gly Gly Ser
            195                 200                 205
Gly Phe Gly Gly Gly Arg Pro Ser Ser Tyr Gly Ala Pro Ser Ser
    210                 215                 220
Gly Ser Phe Gly Gly Gly Phe Gly Gly Gly Ala Pro Ser Ser Ser Tyr
225                 230                 235                 240
Gly Ala Pro Ala Pro Ser Arg Pro Ser Ser Asn Tyr Gly Ala Pro Ala
            245                 250                 255
Pro Ser Arg Pro Ser Ser Asn Tyr Gly Ala Pro Ala Pro Ser Arg Pro
            260                 265                 270
Ser Ser Ser Tyr Gly Ala Pro Ser Arg Pro Ser Ser Asn Tyr Gly Ala
            275                 280                 285
Pro Ser Arg Pro Ser Ser Asn Tyr Gly Ala Pro Ser Gly Gly Ser
            290                 295                 300
Gly Phe Gly Gly Ser Gly Phe Gly Gly Arg Pro Ser Ser Ser
305                 310                 315                 320
Tyr Gly Ala Pro Ser Ser Gly Ser Phe Gly Gly Phe Gly Gly
            325                 330                 335
Ala Pro Ser Ser Tyr Gly Ala Pro Ala Pro Ser Arg Pro Ser Ser
            340                 345                 350
Asn Tyr Gly Pro Pro Ser Ser Tyr Gly Ala Pro Ser Ser Gly Gly
            355                 360                 365
Ser Gly Gly Phe Gly Gly Gly Ala Pro Ser Ser Ser Tyr Gly Ala Pro
            370                 375                 380
```

```
Ser Phe Gly Gly Ser Ser Asn Ala Val Ser Arg Pro Ser Ser Ser Tyr
385                 390                 395                 400

Gly Ala Pro Ser Ser Gly Gly Gln Ser Tyr Ala Ser Asn Gly Gly
            405                 410                 415

Tyr Gln Tyr

<210> SEQ ID NO 19
<211> LENGTH: 396
<212> TYPE: PRT
<213> ORGANISM: Pediculus humanus corporis

<400> SEQUENCE: 19

Glu Pro Pro Val Lys Thr Ser Tyr Leu Pro Ser Ala Ser Arg Ser
1               5                   10                  15

Leu Asn Ser Gln Tyr Gly Ala Pro Ala Phe Thr Asp Ser Asn Glu Leu
                20                  25                  30

Val Ala Pro Ser Pro Asn Ser Asn Phe His Asp Ser Tyr Asn Gln Gln
            35                  40                  45

Gln Gln Ser Phe Asp Leu Ser Asn Gly Leu Ser Val Pro Ser Ala Ala
50                  55                  60

Gly Arg Leu Ser Asn Thr Tyr Gly Val Pro Ser Ala Gln Gly Ala Asn
65                  70                  75                  80

Val Pro Ser Phe Asp Ser Ser Asp Ser Ile Ala Val Asp Ala Ala Gly
                85                  90                  95

Arg Ser Gly Asn Ser Phe Ser Ser His Val Pro Ser Ser Thr Tyr Gly
                100                 105                 110

Ala Pro Gly Asn Gly Phe Gly Gly Ser Arg Ser Ser Gln Ser Gly
            115                 120                 125

Ala Pro Ser Ser Val Tyr Gly Pro Pro Gln Ala Arg Asn Asn Asn Phe
130                 135                 140

Gly Asn Gly Ala Ala Pro Ser Ser Val Tyr Gly Pro Pro Gln Ala Arg
145                 150                 155                 160

Asn Asn Asn Phe Gly Asn Gly Ala Pro Ser Gln Val Tyr Gly Pro
                165                 170                 175

Pro Lys Ala Arg Asn Asn Asn Phe Gly Asn Gly Ala Ala Pro Ser Ser
            180                 185                 190

Val Tyr Gly Pro Pro Gln Ala Arg Asn Asn Asn Phe Gly Asn Gly Ala
            195                 200                 205

Ala Pro Ser Ser Val Tyr Gly Pro Pro Gln Ala Arg Asn Asn Asn Phe
210                 215                 220

Ala Asn Ser Ala Ala Pro Ser Gln Val Tyr Gly Pro Pro Gln Ala Arg
225                 230                 235                 240

Asn Asn Asn Phe Gly Asn Gly Ala Ala Pro Ser Ser Val Tyr Gly Pro
                245                 250                 255

Pro Gln Ser Ser Ser Phe Ser Ser Pro Ser Gly Arg Ser Gly Gln Leu
            260                 265                 270

Pro Ser Ala Thr Tyr Gly Ala Pro Phe Glu Arg Asn Gly Phe Gly Ser
            275                 280                 285

Gln Gly Ser Ser Gly Phe Gln Gly Tyr Glu Pro Ser Lys Arg Ser Gln
            290                 295                 300

Thr Thr Glu Asp Pro Phe Ala Glu Pro Ala Lys Tyr Glu Tyr Asp Tyr
305                 310                 315                 320

Lys Val Gln Ala Ser Asp Glu Thr Gly Thr Glu Phe Gly His Lys Glu
                325                 330                 335
```

Ser Arg Glu Asn Glu Ser Ala Arg Gly Ala Tyr His Val Leu Leu Pro
            340                 345                 350

Asp Gly Arg Met Gln Ile Val Gln Tyr Glu Ala Asp Glu Thr Gly Tyr
        355                 360                 365

Arg Pro Gln Ile Arg Tyr Glu Asp Thr Gly Tyr Pro Ser Ala Ala Ser
370                 375                 380

Ser Arg Ser Asn Asn Gly Phe Asn Gly Tyr Gln Tyr
385                 390                 395

<210> SEQ ID NO 20
<211> LENGTH: 573
<212> TYPE: PRT
<213> ORGANISM: Anopheles gambiae

<400> SEQUENCE: 20

Lys Arg Glu Ala Pro Leu Pro Pro Ser Gly Ser Tyr Leu Pro Pro Ser
1               5                   10                  15

Gly Gly Ala Gly Gly Tyr Pro Ala Ala Gln Thr Pro Ser Ser Ser Tyr
            20                  25                  30

Gly Ala Pro Thr Gly Gly Ala Gly Ser Trp Gly Gly Asn Gly Gly Asn
        35                  40                  45

Gly Gly Arg Gly His Ser Asn Gly Gly Ser Ser Phe Gly Gly Ser
    50                  55                  60

Ala Pro Ser Ala Pro Ser Gln Ser Tyr Gly Ala Pro Ser Phe Gly Gly
65                  70                  75                  80

Gln Ser Ser Gly Gly Phe Gly Gly His Ser Gly Gly Phe Gly Gly
            85                  90                  95

His Ser Ser Gly Gly His Gly Gly Asn Gly Asn Gly Asn Gly Asn Gly
            100                 105                 110

Tyr Ser Ser Gly Arg Pro Ser Ser Gln Tyr Gly Pro Pro Gln Gln Gln
                115                 120                 125

Gln Gln Gln Gln Ser Phe Arg Pro Pro Ser Thr Ser Tyr Gly Val Pro
    130                 135                 140

Ala Ala Pro Ser Gln Ser Tyr Gly Ala Pro Ala Gln Gln His Ser Asn
145                 150                 155                 160

Gly Gly Asn Gly Gly Tyr Ser Ser Gly Arg Pro Ser Thr Gln Tyr Gly
                165                 170                 175

Ala Pro Ala Gln Ser Asn Gly Asn Gly Phe Gly Asn Gly Arg Pro Ser
            180                 185                 190

Ser Ser Tyr Gly Ala Pro Ala Arg Pro Ser Thr Gln Tyr Gly Ala Pro
        195                 200                 205

Ser Ala Gly Asn Gly Asn Gly Tyr Ala Gly Asn Gly Asn Gly Arg Ser
    210                 215                 220

Tyr Ser Asn Gly Asn Gly Asn Gly His Gly Asn Gly His Ser Asn Gly
225                 230                 235                 240

Asn Gly Asn Asn Gly Tyr Ser Arg Gly Pro Ala Arg Gln Pro Ser Gln
                245                 250                 255

Gln Tyr Gly Pro Pro Ala Gln Ala Pro Ser Ser Gln Tyr Gly Ala Pro
            260                 265                 270

Ala Gln Thr Pro Ser Ser Gln Tyr Gly Ala Pro Ala Gln Thr Pro Ser
        275                 280                 285

Ser Gln Tyr Gly Ala Pro Ala Gln Thr Pro Ser Ser Gln Tyr Gly Ala
    290                 295                 300

Pro Ala Gln Thr Pro Ser Ser Gln Tyr Gly Ala Pro Ala Pro Ser Arg

```
                305                 310                 315                 320
Pro Ser Gln Gln Tyr Gly Ala Pro Ala Pro Ser Arg Pro Ser Gln Gln
                325                 330                 335

Tyr Gly Ala Pro Ala Gln Thr Pro Ser Ser Gln Tyr Gly Ala Pro Ala
                340                 345                 350

Gln Thr Pro Ser Ser Gln Tyr Gly Ala Pro Ala Gln Thr Pro Ser Ser
                355                 360                 365

Gln Tyr Gly Ala Pro Ala Gln Thr Pro Ser Ser Gln Tyr Gly Ala Pro
                370                 375                 380

Ala Gln Gln Pro Ser Ser Gln Tyr Gly Ala Pro Ala Pro Ser Arg Pro
385                 390                 395                 400

Ser Gln Gln Tyr Gly Ala Pro Ala Gln Gln Pro Ser Ala Gln Tyr Gly
                405                 410                 415

Ala Pro Ala Gln Thr Pro Ser Ser Gln Tyr Gly Ala Pro Ala Pro Ser
                420                 425                 430

Arg Pro Ser Gln Gln Tyr Gly Ala Pro Ala Gln Ala Pro Ser Ser Gln
                435                 440                 445

Tyr Gly Ala Pro Ala Pro Ser Ser Gln Tyr Gly Ala Pro Ala Gln Gln
                450                 455                 460

Pro Ser Ser Gln Tyr Gly Ala Pro Ala Gln Thr Pro Ser Ser Gln Tyr
465                 470                 475                 480

Gly Ala Pro Ser Phe Gly Pro Thr Gly Gly Ala Ser Phe Ser Ser Gly
                485                 490                 495

Asn Gly Asn Val Gly Gly Ser Tyr Gln Val Ser Ser Thr Gly Asn Gly
                500                 505                 510

Phe Ser Gln Ala Ser Phe Ser Ala Ser Ser Phe Ser Pro Asn Gly Arg
                515                 520                 525

Thr Ser Leu Ser Ala Gly Phe Ser Gly Ala Pro Ser Ala Gln
                530                 535                 540

Ser Ala Gly Gly Tyr Ser Ser Gly Gly Pro Ser Gln Val Pro Ala Thr
545                 550                 555                 560

Leu Pro Gln Ser Tyr Ser Ser Asn Gly Tyr Asn Tyr
                565                 570

<210> SEQ ID NO 21
<211> LENGTH: 513
<212> TYPE: PRT
<213> ORGANISM: Glossina morsitans

<400> SEQUENCE: 21

Arg Pro Glu Pro Pro Val Asn Thr Tyr Leu Pro Pro Ser Ala Gly Gly
1               5                   10                  15

Gly Ser Gly Gly Gly Ser Pro Leu Ala Pro Ser Asp Thr Tyr Gly Ala
                20                  25                  30

Pro Gly Val Asn Gly Gly Gly Gly Gly Gly Pro Ser Ser Thr
                35                  40                  45

Tyr Gly Ala Pro Gly Ser Gly Gly Asn Gly Asn Gly Gly Gly Gly
                50                  55                  60

Phe Gly Lys Pro Ser Ser Thr Tyr Gly Ala Pro Gly Leu Gly Gly
65                  70                  75                  80

Gly Asn Gly Gly Gly Arg Pro Ser Glu Thr Tyr Gly Ala Pro Ser Gly
                85                  90                  95

Gly Gly Gly Asn Gly Phe Gly Lys Pro Ser Ser Thr Tyr Gly Ala Pro
                100                 105                 110
```

-continued

Asn Gly Gly Gly Gly Asn Gly Pro Gly Arg Pro Ser Ser Thr Tyr
            115                 120                 125

Gly Ala Pro Gly Ser Gly Gly Asn Gly Gly Ser Gly Arg Pro Ser
130                 135                 140

Ser Thr Tyr Gly Ala Pro Gly Leu Gly Gly Asn Gly Gly Ser Gly
145                 150                 155                 160

Arg Pro Ser Ser Met Tyr Gly Ala Pro Gly Leu Gly Gly Asn Gly
                165                 170                 175

Gly Ser Gly Arg Pro Ser Ser Thr Tyr Gly Ala Pro Gly Ser Gly
                180                 185                 190

Gly Asn Gly Gly Ser Gly Arg Pro Ser Ser Thr Tyr Gly Ala Pro Gly
        195                 200                 205

Ser Gly Gly Asn Gly Gly Ser Gly Arg Pro Ser Ser Thr Tyr Gly
210                 215                 220

Ala Pro Gly Asn Gly Asn Gly Gly Asn Gly Phe Gly Arg Pro Ser Ser
225                 230                 235                 240

Thr Tyr Gly Ala Pro Gly Ser Gly Gly Ser Asn Gly Asn Gly Lys Pro
                245                 250                 255

Ser Ser Thr Tyr Gly Ala Pro Gly Ser Gly Gly Gly Gly Arg Pro
                260                 265                 270

Ser Asp Ser Tyr Gly Pro Pro Ala Ser Gly Asn Gly Arg Asn Gly
        275                 280                 285

Asn Gly Asn Gly Gln Ser Gln Glu Tyr Leu Pro Pro Gly Gln Ser Gly
290                 295                 300

Ser Gly Gly Gly Gly Tyr Gly Gly Gly Ser Gly Ser Gly Gly Ser
305                 310                 315                 320

Gly Gly Gly Gly Gly Gly Tyr Gly Gly Asp Gln Asp Asn Asn Val
                325                 330                 335

Val Glu Tyr Glu Ala Asp Gln Glu Gly Tyr Arg Pro Gln Ile Arg Tyr
                340                 345                 350

Glu Gly Asp Gly Ser Gln Gly Gly Phe Gly Gly Asp Gly Asp Gly Tyr
                355                 360                 365

Ser Tyr Glu Gln Asn Gly Val Gly Gly Asp Gly Gly Ala Gly Gly
370                 375                 380

Ala Gly Gly Tyr Ser Asn Gly Gln Asn Leu Gly Ala Asn Gly Tyr Ser
385                 390                 395                 400

Ser Gly Arg Pro Asn Gly Gly Asn Gly Gly Arg Arg Gly Gly Gly
                405                 410                 415

Gly Gly Gly Gly Gly Ser Gly Gly Gln Asn Leu Gly Ser Asn Gly
                420                 425                 430

Tyr Ser Ser Gly Ala Pro Asn Gly Phe Gly Gly Asn Gly Gln Gly
                435                 440                 445

Tyr Ser Gly Gly Arg Ser Asn Gly Asn Gly Gly Gly Gly Gly Arg
450                 455                 460

Asn Gly Gly Arg Tyr Arg Asn Gly Gly Gly Gly Gly Gly Arg Asn
465                 470                 475                 480

Gly Gly Gly Ser Asn Gly Tyr Asn Tyr Asp Gln Pro Gly Ser Asn Gly
                485                 490                 495

Phe Gly Arg Gly Gly Gly Asn Gly Glu Asn Asp Gly Ser Gly Tyr His
                500                 505                 510

Tyr

<210> SEQ ID NO 22

<211> LENGTH: 506
<212> TYPE: PRT
<213> ORGANISM: Atta cephalotes

<400> SEQUENCE: 22

Arg Ser Glu Pro Pro Val Asn Ser Tyr Leu His Pro Gly Ser Asp Thr
1               5                   10                  15

Ser Gly Thr Asn Gly Gly Arg Thr Asp Leu Ser Thr Gln Tyr Gly Ala
            20                  25                  30

Pro Asp Phe Asn Asn Arg Gly Asn Gly Asn Ser Gly Ala Thr Ser Phe
        35                  40                  45

Gly Gly Ser Gly Ala Gly Asn Gly Pro Ser Lys Leu Tyr Asp Val Pro
    50                  55                  60

Ile Arg Gly Asn Thr Gly Gly Asn Gly Leu Gly Gln Phe Arg Gly Asn
65                  70                  75                  80

Gly Phe Glu Ser Gly Gln Pro Ser Ser Tyr Gly Ala Pro Lys Gly
                85                  90                  95

Gly Phe Gly Glu Asn Arg Gly Asn Arg Gly Arg Pro Ser Thr Ser Tyr
            100                 105                 110

Gly Val Pro Asp Ser Asn Arg Asn Asn Arg Gly Gly Phe Gly Asn Gly
        115                 120                 125

Gly Ser Glu Ala Arg Pro Ser Thr Ser Tyr Gly Val Pro Gly Ala Asn
    130                 135                 140

Gly Asn Gln Gly Gly Phe Gly Ser Gly Ser Ile Gly Gly Arg Pro Ser
145                 150                 155                 160

Thr Ser Tyr Gly Val Pro Gly Ala Asn Gly Asn Asn Gly Asp Ser Phe
                165                 170                 175

Arg Asn Gly Asp Ile Gly Gly Arg Pro Ser Thr Asn Tyr Gly Ala Pro
            180                 185                 190

Gly Ala Asn Gly Asn His Gly Gly Asn Gly Asn Gly Arg Pro
        195                 200                 205

Ser Asn Asn Tyr Gly Val Pro Gly Ala Asn Gly Asn Thr Asn Gly Lys
    210                 215                 220

Gly Arg Leu Asn Gly Asn Ser Gly Gly Pro Ser Asn Asn Tyr Gly
225                 230                 235                 240

Ser Pro Asn Gly Phe Gly Lys Gly Leu Ser Thr Ser Tyr Gly Ser Pro
                245                 250                 255

Asn Arg Gly Gly Asn Asp Asn His Tyr Pro Ser Arg Gly Ser Phe Ile
            260                 265                 270

Asn Gly Gly Ile Asn Gly Tyr Ser Ser Gly Ser Pro Asn Gly Asn Ala
        275                 280                 285

Gly Asn Phe Gly His Gly Asp Glu Ser Phe Gly Arg Gly Gly Gly Glu
    290                 295                 300

Gly Glu Asn Thr Gly Glu Gly Tyr Asn Ala Asn Ala Gln Glu Glu Ser
305                 310                 315                 320

Thr Glu Pro Ala Lys Tyr Glu Phe Ser Tyr Lys Val Lys Asp Gln Gln
                325                 330                 335

Thr Gly Ser Asp Tyr Ser His Thr Glu Thr Arg Asp Gly Asp His Ala
            340                 345                 350

Gln Gly Glu Phe Asn Val Leu Leu Pro Asp Gly Arg Lys Gln Ile Val
        355                 360                 365

Glu Tyr Glu Ala Asp Gln Asp Gly Phe Lys Pro Gln Ile Arg Tyr Glu
    370                 375                 380

Gly Glu Ala Asn Ala Asp Gly Gly Tyr Gly Ser Gly Leu Asn Asp Asn

```
                385                 390                 395                 400
Asn Asp Gly Tyr Ser Ser Gly Arg Pro Asp Ser Glu Ser Gly Phe
                    405                 410                 415

Ala Asn Ser Gly Phe Asn Gly Gly Ser Ser Asn Gly Gly Tyr Pro Asn
                    420                 425                 430

Gly Gly Pro Gly Glu Arg Lys Leu Gly Gly Phe Asn Asn Gly Gly Ser
                435                 440                 445

Ser Gly Tyr Gln Ser Gly Arg Ser Ala Gly Gln Ser Phe Gly Arg Asp
            450                 455                 460

Asn Ala Gly Asp Leu Asn Asn Asp Ile Gly Gly Tyr Phe Ser Asn Ser
465                 470                 475                 480

Pro Asn Asn Ile Gly Asp Ser Asp Asn Ala Asn Val Gly Ser Asn Arg
                    485                 490                 495

Gln Asn Asp Gly Asn Ser Gly Tyr Gln Tyr
                500                 505

<210> SEQ ID NO 23
<211> LENGTH: 550
<212> TYPE: PRT
<213> ORGANISM: Anopheles darlingi

<400> SEQUENCE: 23

Lys Arg Glu Ala Pro Leu Pro Pro Ser Gly Ser Tyr Leu Pro Pro Ser
1               5                   10                  15

Gly Gly Gly Gly Gly Gly Gly Tyr Pro Ala Ala Gln Thr Pro Ser
                20                  25                  30

Ser Ser Tyr Gly Ala Pro Ala Gly Ala Gly Gly Trp Gly Gly Asn
            35                  40                  45

Gly Asn Gly Asn Gly Asn Gly Asn Gly Gly Arg Gly Gly Tyr Ser Asn
50                  55                  60

Gly Gly Gly His Ser Gly Ser Ala Pro Ser Gln Ser Tyr Gly Ala Pro
65                  70                  75                  80

Ser Ala Pro Ser Gln Ser Tyr Gly Ala Pro Ser Gln Ser Tyr Gly Ala
                85                  90                  95

Pro Ala Ala Ala Pro Ser Gln Ser Tyr Gly Ala Pro Ser Phe Gly Gly
                100                 105                 110

Asn Gly Gly Gly Ala Ser His Gly Ser Gly Gly Phe Thr Gly Gly His
                115                 120                 125

Gly Gly Asn Gly Asn Gly Asn Gly Tyr Ser Ser Gly Arg Pro Ser Ser
            130                 135                 140

Gln Tyr Gly Pro Pro Gln Gln Gln Gln Pro Gln Gln Ser Phe
145                 150                 155                 160

Arg Pro Pro Ser Thr Ser Tyr Gly Val Pro Ala Ala Pro Ser Ser Ser
                    165                 170                 175

Tyr Gly Ala Pro Ser Ala Asn Gly Phe Ser Asn Gly Arg Pro Ser
                180                 185                 190

Ser Gln Tyr Gly Ala Pro Ala Pro Gln Ser Asn Gly Asn Glu Phe Gly
            195                 200                 205

Ala Pro Arg Pro Ser Ser Tyr Gly Ala Pro Ser Arg Pro Ser Thr
                210                 215                 220

Gln Tyr Gly Ala Pro Ser Asn Gly Asn Gly Asn Gly Tyr Ala Gly His
225                 230                 235                 240

Gly Asn Gly Asn Gly His Gly Asn Gly Asn Gly His Ser Asn Gly Asn
                    245                 250                 255
```

Gly Asn Gly Tyr Asn Arg Gly Pro Ala Arg Gln Pro Ser Ser Gln Tyr
            260                 265                 270

Gly Pro Pro Ser Gln Gly Pro Pro Ser Ser Gln Tyr Gly Pro Pro Ser
        275                 280                 285

Gln Tyr Gly Pro Pro Ser Ser Gly Thr Ser Phe Ile Ala Tyr Gly Pro
    290                 295                 300

Pro Ser Gln Gly Pro Ser Ser Gln Tyr Gly Ala Pro Ala Pro Ser
305                 310                 315                 320

Arg Pro Ser Ser Gln Tyr Gly Ala Pro Ala Gln Thr Pro Ser Ser Gln
                325                 330                 335

Tyr Gly Ala Pro Ala Gln Thr Pro Ser Ser Gln Tyr Gly Pro Pro Arg
            340                 345                 350

Gln Ser Ser Pro Gln Phe Gly Ala Pro Ala Arg Pro Pro Ser Ser
        355                 360                 365

Gln Tyr Gly Ala Pro Ala Gln Ala Pro Ser Ser Gln Tyr Gly Ala Pro
    370                 375                 380

Ala Gln Thr Pro Ser Ser Gln Tyr Gly Ala Pro Ala Gln Ala Pro Ser
385                 390                 395                 400

Ser Gln Tyr Gly Ala Pro Ala Pro Ser Arg Pro Ser Ser Gln Tyr Gly
                405                 410                 415

Val Pro Ala Gln Ala Pro Ser Ser Gln Tyr Gly Ala Pro Ala Gln Ala
            420                 425                 430

Pro Ser Ser Gln Tyr Gly Ala Pro Ala Gln Thr Pro Ser Ser Gln Tyr
        435                 440                 445

Gly Ala Pro Ser Phe Gly Ser Thr Gly Ser Ser Phe Gly Gly Asn
    450                 455                 460

Gly Gly Val Gly Gly Ser Tyr Gln Thr Ala Ser Ser Gly Asn Gly Phe
465                 470                 475                 480

Ser Gln Ala Ser Phe Ser Ala Ser Ser Phe Ser Ser Asn Gly Arg Ser
                485                 490                 495

Ser Gln Ser Ala Gly Gly Tyr Ser Ser Gly Gly Pro Ser Gln Val Pro
            500                 505                 510

Ala Thr Ile Pro Gln Gln Tyr Ser Ser Gly Gly Ser Tyr Ser Ser
        515                 520                 525

Gly Gly His Ser Gln Val Pro Ala Thr Leu Pro Gln Gln Tyr Ser Ser
    530                 535                 540

Asn Gly Gly Tyr Asn Tyr
545                 550

<210> SEQ ID NO 24
<211> LENGTH: 585
<212> TYPE: PRT
<213> ORGANISM: Acromyrmex echinatior

<400> SEQUENCE: 24

Arg Ser Glu Pro Pro Val Asn Ser Tyr Leu Pro Pro Gly Pro Gly Thr
1               5                   10                  15

Ser Gly Ala Asn Gly Gly Gln Thr Asp Leu Ser Ile Gln Tyr Arg Ala
            20                  25                  30

Ser Asp Phe Asn Asn Arg Gly Asn Val Asn Gly Asn Ser Gly Ala Thr
        35                  40                  45

Ser Phe Gly Gly Pro Gly Ala Ser Asn Gly Pro Ser Lys Leu Tyr Asp
    50                  55                  60

Val Pro Ile Gly Gly Asn Ala Gly Gly Asn Gly Leu Gly Gln Phe Arg
65                  70                  75                  80

-continued

```
Gly Asn Gly Phe Glu Gly Gly Gln Pro Ser Ser Tyr Gly Ala Pro
                 85                  90                  95
Asn Gly Gly Phe Gly Glu Asn Arg Gly Asn Gly Lys Pro Ser Thr
                100                 105                 110
Ser Tyr Gly Val Pro Asp Ser Asn Gly Asn Asn Arg Gly Gly Phe Gly
                115                 120                 125
Asn Gly Gly Ser Glu Gly Arg Pro Ser Thr Ser Tyr Gly Leu Pro Asp
130             135                 140
Ala Ser Arg Asn Asn Gly Asn Gly Phe Gly Asn Val Gly Asn Glu Asp
145                 150                 155                 160
Lys Pro Ser Thr Asn Tyr Gly Ile Pro Ala Asn Gly Asn Lys Val Ser
                165                 170                 175
Gly Phe Gly Asn Val Gly Ser Glu Gly Arg Pro Ser Thr Ser Tyr Gly
                180                 185                 190
Val Pro Gly Ala Asn Gly Asn Gln Gly Phe Gly Ser Gly Gly Ile Gly
                195                 200                 205
Gly Arg Pro Ser Thr Ser Tyr Gly Val Pro Gly Val Asn Gly Asn Asn
                210                 215                 220
Gly Gly Gly Phe Glu Asn Val Gly Arg Pro Ser Thr Ser Tyr Gly Thr
225                 230                 235                 240
Pro Asp Ala Arg Gly Asn Asn Gly Gly Ser Phe Arg Asn Gly Asp Ile
                245                 250                 255
Gly Gly Arg Pro Ser Thr Asn Tyr Gly Ile Pro Gly Ala Asn Gly Asn
                260                 265                 270
His Gly Gly Asn Gly Gly Asn Gly Arg Pro Ser Ser Asn Tyr Gly
                275                 280                 285
Val Pro Gly Gly Asn Gly Asn Thr Asn Gly Lys Gly Arg Phe Asn Gly
290                 295                 300
Asn Ser Gly Gly Arg Pro Ser Asn Ser Tyr Gly Ser Pro Asn Gly Phe
305                 310                 315                 320
Gly Lys Gly Leu Ser Thr Ser Tyr Ser Pro Ser Asn Arg Asp Gly Asn
                325                 330                 335
Gly Asn His Tyr Pro Ser Gly Asp Ser Asn Arg Gly Ser Phe Val Asn
                340                 345                 350
Gly Gly Ile Asn Gly Tyr Pro Ser Gly Ser Pro Asn Gly Asn Ala Gly
                355                 360                 365
Asn Phe Arg His Gly Asp Glu Ser Phe Gly Arg Gly Gly Glu Gly Gly
                370                 375                 380
Gly Arg Ser Thr Gly Glu Gly Tyr Asn Ala Asn Ala Gln Glu Glu Ser
385                 390                 395                 400
Thr Glu Pro Ala Lys Tyr Glu Phe Ser Tyr Lys Val Lys Asp Gln Gln
                405                 410                 415
Thr Gly Ser Asp Tyr Ser His Thr Glu Thr Arg Asp Gly Asp His Ala
                420                 425                 430
Gln Gly Glu Phe Asn Val Leu Leu Pro Asp Gly Arg Lys Gln Ile Val
                435                 440                 445
Glu Tyr Glu Ala Asp Gln Asp Gly Phe Lys Pro Gln Ile Arg Tyr Glu
                450                 455                 460
Gly Glu Ala Asn Ala Asp Gly Glu Tyr Asp Ser Gly Leu Asn Asp
465                 470                 475                 480
Asn Asn Asp Gly Tyr Ser Ser Gly Arg Pro Gly Ser Glu Ser Gly Gly
                485                 490                 495
```

```
Phe Ala Asn Asn Ser Gly Phe Asn Gly Ser Ser Asn Gly Gly Tyr
                500                 505                 510

Pro Ser Gly Gly Ser Gly Glu Gly Lys Leu Gly Phe Asn Ser Gly Gly
                515                 520                 525

Asn Ser Gly Tyr Gln Ser Gly Arg Pro Ala Gly Gln Ser Phe Gly Arg
                530                 535                 540

Asp Asn Ala Gly Asp Leu Ser Asn Asp Ile Gly Gly Phe Ser Asn Ser
545                 550                 555                 560

Pro Asn Asn Ile Gly Gly Asp Asn Ala Asn Val Gly Ser Asn Arg Gln
                565                 570                 575

Asn Gly Gly Asn Ser Gly Tyr Gln Tyr
                580                 585

<210> SEQ ID NO 25
<211> LENGTH: 748
<212> TYPE: PRT
<213> ORGANISM: Acyrthosiphon pisum

<400> SEQUENCE: 25

Glu Ser Pro Tyr Gly Gly Gly Ser Ser Asn Ser Asn Gly Asn Gly Arg
1               5                   10                  15

Asn Gly Gly Tyr Gly Gly Lys Gly Gln Tyr Gly Gly Gly Asn Gly Gly
                20                  25                  30

Gly Val Gly Ser Ser Ser Ala Ser Pro Phe Phe Ser Gly Ala Asn Gln
                35                  40                  45

Tyr Gly Ser Gln Ser Gly Leu Ser Gly Ala Ala Asn Asn Arg Tyr Pro
        50                  55                  60

Ser Phe Gly Ser Lys Phe Gly Gly Asn Lys Gly Ser Tyr Gly Gly Ser
65                  70                  75                  80

Ser Ser Arg Asn Asn Gly Arg Tyr Gly Ser Gly Ser Ala Ser Gly Tyr
                85                  90                  95

Gly Ser Gly Ser Ser Gly Gly Leu Gly Ser Thr Gly Arg Ser Thr Gly
                100                 105                 110

Gly Tyr Gly Gly Gly Ser Ser Gly Ser Tyr Gly Ser Gly Ser Ser Gly
                115                 120                 125

Ser Leu Gly Ser Ser Thr Gly Ser Asn Gly Ile Tyr Gly Ala Gly Ser
        130                 135                 140

Ser Gly Gly Phe Gly Ser Gly Ser Ser Gly Ser Tyr Gly Gly Gly Ser
145                 150                 155                 160

Ser Gly Gly Phe Gly Ser Gly Ser Ser Gly Ser Tyr Gly Gly Gly Ser
                165                 170                 175

Ser Gly Gly Phe Gly Ser Gly Ser Ser Gly Ser Tyr Gly Gly Gly Ser
                180                 185                 190

Ser Gly Gly Phe Gly Ser Gly Ser Ser Gly Ser Tyr Gly Gly Gly Ser
                195                 200                 205

Ser Gly Gly Phe Gly Ser Gly Ser Ser Gly Asn Tyr Gly Ser Gly Ser
                210                 215                 220

Ser Gly Ser Tyr Gly Ser Gly Gly Gly Leu Gly Ala Ser Ser
225                 230                 235                 240

Gly Asn Asn Asp Gly Tyr Gly Ala Gly Ser Gly Ser Tyr Asp Gln
                245                 250                 255

Leu Gly Gly Ala Asn Gly Asn Gly Leu Gly Gly Ser Gly Asn Asp Pro
        260                 265                 270

Leu Ser Glu Pro Ala Asn Tyr Glu Phe Ser Tyr Glu Val Asn Ala Pro
        275                 280                 285
```

```
Glu Ser Gly Ala Ile Phe Gly His Lys Glu Ser Arg Gln Gly Glu Glu
    290                 295                 300

Ala Thr Gly Val Tyr His Val Leu Leu Pro Asp Gly Arg Thr Gln Ile
305                 310                 315                 320

Val Glu Tyr Glu Ala Asp Glu Asp Gly Tyr Lys Pro Lys Ile Thr Tyr
                    325                 330                 335

Thr Asp Pro Val Gly Gly Tyr Ala Gly Asp Arg Gln Ser Gly Asn Ser
            340                 345                 350

Tyr Gly Gly Asn Gly Gly Phe Gly Gly Ser Gly Ser Leu Gly Gly Ser
                355                 360                 365

Gly Gly Asn Leu Gly Gly Leu Tyr Asn Gly Gly Ser Ser Asn Asn
370                 375                 380

Gly Ala Gly Tyr Gly Gly Ser Ser Ser Leu Gly Ser Arg Tyr Gly
385                 390                 395                 400

Gly Ser Gly Gly Ser Ser Gly Ser Gly Val Gly Gly Tyr Gly Gly
                405                 410                 415

Ser Gly Ser Ser Ser Gly Gly Ile Gly Ser Ser Tyr Gly Gly Ser Gly
                420                 425                 430

Ser Leu Ser Gly Gly Leu Gly Gly Tyr Gly Gly Ser Gly Ser Ser
            435                 440                 445

Ser Gly Gly Leu Gly Gly Tyr Gly Gly Ser Gly Gly Ser Ser Gly
450                 455                 460

Gly Gly Phe Gly Gly Leu Gly Gly Ser Gly Gly Ser Gly Ser Gly
465                 470                 475                 480

Tyr Gly Gly Ser Gly Ser Ser Gly Gly Leu Gly Asn Ser Tyr Gly
                485                 490                 495

Gly Ser Gly Ser Ser Asn Gly Gly Leu Gly Gly Tyr Ser Gly Ser
            500                 505                 510

Gly Gly Ser Ser Gly Gly Leu Gly Gly Tyr Gly Ala Ser Ser Gly
            515                 520                 525

Ser Ser Gly Ser Gly Leu Gly Gly Tyr Gly Gly Ser Gly Ser Ser
            530                 535                 540

Ser Gly Gly Leu Gly Ser Gly Tyr Gly Gly Leu Gly Ser Ser Gly
545                 550                 555                 560

Gly Leu Gly Gly Gly Tyr Gly Gly Ser Gly Ser Ser Ser Gly Gly Leu
                565                 570                 575

Gly Gly Gly Tyr Gly Gly Ser Gly Ser Ser Asn Gly Gly Ile Gly Gly
                580                 585                 590

Gly Tyr Gly Gly Ser Ser Gly Ser Ser Gly Gly Leu Gly Gly Tyr
    595                 600                 605

Gly Gly Ser Gly Ser Ser Gly Gly Leu Gly Gly Tyr Gly Gly
    610                 615                 620

Ser Gly Gly Ser Asn Ser Gly Leu Gly Ser Ser Tyr Gly Gly Ser Gly
625                 630                 635                 640

Ser Thr Asn Gly Gly Leu Gly Gly Tyr Gly Gly Leu Gly Ser Ser
            645                 650                 655

Ser Gly Gly Leu Gly Gly Gly Tyr Gly Gly Ser Gly Gly Ser Asn Gly
                660                 665                 670

Gly Ile Gly Gly Gly Tyr Gly Gly Ser Ser Gly Ser Gly Gly Ser Gln
            675                 680                 685

Gly Ser Ala Tyr Gly Gly Ser Gly Ser Ser Ser Gly Ser Gln Gly Gly
690                 695                 700
```

Gly Tyr Gly Gly Ser Gly Ser Ser Gly Gly Leu Gly Gly Gly Tyr
705                 710                 715                 720

Gly Ser Ser Ser Gly Ser Ser Ser Gly Leu Gly Gly Ser Tyr Gly Ser
                725                 730                 735

Asn Arg Asn Gly Leu Gly Ser Gly Ser Ser Tyr Ser
            740                 745

<210> SEQ ID NO 26
<211> LENGTH: 616
<212> TYPE: PRT
<213> ORGANISM: Drosophila virilis

<400> SEQUENCE: 26

Arg Pro Glu Pro Pro Val Asn Ser Tyr Leu Pro Pro Ser Pro Gly Asp
1               5                   10                  15

Ser Tyr Gly Ala Pro Gly Gln Gly Gln Gly Gln Gly Gln Gly Gly Phe
                20                  25                  30

Gly Gly Lys Pro Ser Asp Ser Tyr Gly Ala Pro Gly Ala Gly Asn Gly
            35                  40                  45

Asn Gly Asn Gly Arg Pro Ser Ser Tyr Gly Ala Pro Gly Gln Gly
50                  55                  60

Gln Gly Gln Gly Gly Phe Gly Gly Lys Pro Ser Asp Ser Tyr Gly Ala
65                  70                  75                  80

Pro Gly Ala Gly Asn Gly Asn Gly Asn Gly Arg Pro Ser Ser Ser Tyr
                85                  90                  95

Gly Ala Pro Gly Gln Gly Gln Gly Gln Gly Gly Phe Gly Gly Arg Pro
                100                 105                 110

Ser Ser Ser Tyr Gly Ala Pro Gly Gln Gly Gln Gly Gly Phe Gly Gly
            115                 120                 125

Lys Pro Ser Asp Thr Tyr Gly Ala Pro Gly Ala Gly Asn Gly Asn Gly
    130                 135                 140

Arg Pro Ser Ser Ser Tyr Gly Ala Pro Gly Gln Gly Gln Gly Gly Ile
145                 150                 155                 160

Gly Gly Lys Pro Ser Asp Ser Tyr Gly Ala Pro Gly Ala Gly Asn Gly
                165                 170                 175

Asn Gly Asn Gly Arg Pro Ser Ser Tyr Gly Ala Pro Gly Gln Gly
                180                 185                 190

Gln Gly Gly Phe Gly Gly Lys Pro Ser Asp Thr Tyr Gly Ala Pro Gly
            195                 200                 205

Ala Gly Asn Gly Asn Gly Arg Pro Ser Ser Tyr Gly Ala Pro Gly
    210                 215                 220

Gln Gly Gln Gly Gly Phe Gly Gly Lys Pro Ser Asp Thr Tyr Gly Ala
225                 230                 235                 240

Pro Gly Ala Gly Asn Gly Asn Gly Asn Gly Arg Pro Ser Ser Ser Tyr
                245                 250                 255

Gly Ala Pro Gly Gln Gly Gln Gly Gly Phe Gly Gly Lys Pro Ser Asp
                260                 265                 270

Thr Tyr Gly Ala Pro Gly Ala Gly Asn Gly Asn Gly Arg Pro Ser Ser
            275                 280                 285

Ser Tyr Gly Ala Pro Gly Gln Gly Gln Gly Gln Gly Gly Phe Gly Gly
            290                 295                 300

Lys Pro Ser Asp Ser Tyr Gly Pro Pro Ala Ser Gly Ala Gly Ala Gly
305                 310                 315                 320

Gly Ala Gly Gly Pro Gly Ala Gly Gly Gly Asp Tyr Asp Asn Asp
                325                 330                 335

Glu Pro Ala Lys Tyr Glu Phe Asn Tyr Gln Val Glu Asp Ala Pro Ser
                340                 345                 350

Gly Leu Ser Phe Gly His Ser Glu Met Arg Asp Gly Asp Phe Thr Thr
            355                 360                 365

Gly Gln Tyr Asn Val Leu Leu Pro Asp Gly Arg Lys Gln Ile Val Glu
    370                 375                 380

Tyr Glu Ala Asp Gln Gln Gly Tyr Arg Pro Gln Val Arg Tyr Glu Gly
385                 390                 395                 400

Asp Ala Asn Gly Asn Gly Gly Pro Gly Gly Ala Gly Pro Gly Gly
                405                 410                 415

Gln Asp Leu Gly Gln Asn Gly Tyr Ser Ser Gly Arg Pro Gly Gly Gln
                420                 425                 430

Asp Leu Gly Gln Gly Gly Tyr Ser Asn Gly Arg Pro Gly Gly Gln Asp
            435                 440                 445

Leu Gly Gln Asn Gly Tyr Ser Gly Gly Arg Pro Gly Gly Gln Asp Leu
    450                 455                 460

Gly Gln Asn Gly Tyr Ser Gly Gly Arg Pro Gly Gly Gln Asp Leu Gly
465                 470                 475                 480

Gln Asn Gly Tyr Ser Gly Gly Arg Pro Gly Gly Gln Asp Leu Gly Gln
                485                 490                 495

Asn Gly Tyr Ser Gly Gly Arg Pro Gly Gly Gln Asp Leu Gly Gln Asn
            500                 505                 510

Gly Tyr Ser Gly Gly Arg Pro Gly Gly Gln Asp Leu Gly Gln Asn Gly
    515                 520                 525

Tyr Ser Gly Gly Arg Pro Gly Gly Asn Gly Gly Ser Asp Gly Gly Arg
530                 535                 540

Val Ile Ile Gly Gly Arg Val Ile Gly Gln Asp Gly Gly Asp Gly Gln
545                 550                 555                 560

Gly Tyr Ser Ser Gly Arg Pro Asn Gly Gln Asp Gly Gly Phe Gly Gln
                565                 570                 575

Asp Asn Thr Asp Gly Arg Gly Tyr Ser Ser Gly Lys Pro Gly Gln Gly
            580                 585                 590

Arg Asn Gly Asn Gly Asn Ser Phe Gly Pro Gly Gly Gln Asn Gly Asp
    595                 600                 605

Asn Asp Gly Ser Gly Tyr Arg Tyr
    610                 615

<210> SEQ ID NO 27
<211> LENGTH: 557
<212> TYPE: PRT
<213> ORGANISM: Drosophila erecta

<400> SEQUENCE: 27

Arg Pro Glu Pro Pro Val Asn Ser Tyr Leu Pro Pro Ser Asp Ser Tyr
1               5                   10                  15

Gly Ala Pro Gly Gln Ser Gly Pro Gly Gly Arg Pro Ser Asp Ser Tyr
            20                  25                  30

Gly Ala Pro Gly Gly Gly Asn Gly Gly Arg Pro Ser Asp Ser Tyr Gly
        35                  40                  45

Ala Pro Gly Leu Gly Gln Gly Gln Gly Gln Gly Gln Gly Gln Gly Gly
    50                  55                  60

Phe Gly Gly Lys Pro Ser Asp Ser Tyr Gly Ala Pro Gly Ala Gly Asn
65                  70                  75                  80

Gly Asn Gly Gly Arg Pro Ser Ser Ser Tyr Gly Ala Pro Gly Ala Gly

```
                      85                  90                  95
Asn Gly Gly Arg Pro Ser Asp Thr Tyr Gly Ala Pro Gly Gly Ser
                 100                 105                 110

Gly Gly Arg Pro Ser Asp Thr Tyr Gly Ala Pro Gly Gly Asn Gly
            115                 120                 125

Asn Gly Asn Gly Gly Arg Pro Ser Ser Ser Tyr Gly Ala Pro Gly Gln
        130                 135                 140

Gly Gln Gly Asn Gly Asn Ser Gly Arg Pro Ser Ser Tyr Gly Ala
145                 150                 155                 160

Pro Gly Ala Gly Asn Gly Gly Arg Pro Ser Asp Thr Tyr Gly Ala Pro
                165                 170                 175

Gly Gly Gly Asn Gly Arg Pro Ser Ser Tyr Gly Ala Pro Gly
            180                 185                 190

Ala Gly Asn Gly Asn Gly Gly Arg Pro Ser Asp Thr Tyr Gly Ala
        195                 200                 205

Pro Gly Gly Gly Asn Gly Asn Gly Asn Gly Asn Gly Ser Gly
    210                 215                 220

Gly Arg Pro Ser Ser Ser Tyr Gly Ala Pro Gly Gln Gly Gln Gly Gly
225                 230                 235                 240

Phe Gly Gly Arg Pro Ser Asp Ser Tyr Gly Ala Pro Gly Gln Asn Gln
                245                 250                 255

Lys Pro Ser Asp Ser Tyr Gly Ala Pro Gly Ser Gly Ser Gly Ser Gly
                260                 265                 270

Asn Gly Asn Gly Gly Arg Pro Ser Ser Tyr Gly Ala Pro Gly Ser
        275                 280                 285

Gly Pro Gly Gly Arg Pro Ser Asp Ser Tyr Gly Pro Pro Ala Ser Gly
        290                 295                 300

Ser Gly Ala Gly Gly Ala Gly Ser Gly Pro Gly Ala Asp Tyr
305                 310                 315                 320

Asp Asn Asp Ile Val Glu Tyr Glu Ala Asp Gln Gln Gly Tyr Arg Pro
                325                 330                 335

Gln Ile Arg Tyr Glu Gly Asp Ala Asn Asp Gly Ser Gly Pro Ser Gly
            340                 345                 350

Pro Gly Gly Gln Asn Leu Gly Ala Asp Gly Tyr Ser Ser Gly Arg Pro
            355                 360                 365

Gly Asn Gly Asn Gly Asn Gly Asn Gly Gly Tyr Ser Gly Gly Arg Pro
        370                 375                 380

Gly Gly Gln Asp Leu Gly Pro Ser Gly Tyr Ser Gly Gly Arg Pro Gly
385                 390                 395                 400

Gly Gln Asp Leu Gly Ala Gly Gly Tyr Ser Asn Gly Arg Pro Gly Gly
            405                 410                 415

Gln Asp Leu Gly Pro Ser Gly Tyr Gly Gly Arg Pro Gly Gly Gln
        420                 425                 430

Asp Leu Gly Pro Ser Gly Tyr Ser Gly Arg Pro Gly Gly Gln Asp
        435                 440                 445

Leu Gly Ala Gly Gly Tyr Ser Asn Gly Arg Pro Gly Gly Asn Gly Asn
    450                 455                 460

Gly Asn Gly Gly Ala Asp Gly Gly Arg Val Ile Ile Gly Gly Arg Val
465                 470                 475                 480

Ile Gly Gly Gln Asp Gly Gly Asp Gly Tyr Ser Gly Gly Arg Pro
            485                 490                 495

Gly Gly Gln Asp Leu Gly Arg Asp Gly Tyr Ser Ser Gly Arg Pro Gly
                500                 505                 510
```

Gly Arg Pro Gly Ala Asn Gly Gln Asp Asn Gln Asp Gly Gln Gly Tyr
            515                 520                 525

Ser Ser Gly Arg Ser Gly Lys Gly Gly Arg Asn Ser Phe Gly Pro Gly
    530                 535                 540

Gly Gln Asn Gly Asp Asn Asp Gly Ser Gly Tyr Arg Tyr
545                 550                 555

<210> SEQ ID NO 28
<211> LENGTH: 796
<212> TYPE: PRT
<213> ORGANISM: Lutzomyia longipalpis

<400> SEQUENCE: 28

Arg Pro Glu Pro Pro Ala Asn Thr Tyr Leu Pro Pro Ser Ser Ser Tyr
1               5                   10                  15

Ala Ala Pro Gly Gln Gln Gly Gly Ser Gly Phe Gly Gly Gly Gly Gly
            20                  25                  30

Ser Gly Gly Ser Gly Gly Phe Gly Gln Pro Gly Ala Phe Gly Arg Pro
    35                  40                  45

Ser Ser Ser Tyr Gly Pro Pro Ser Gln Gly Gly Ala Gly Gly Gly Phe
50                  55                  60

Gly Ser Asp Ser Gln Phe Gly Gly Phe Gly Gly Ala Gly Gly
65                  70                  75                  80

Phe Gly Ser Gly Gly Ser Gly Ala Pro Gly Ala Ser Gln Arg Pro Ser
                85                  90                  95

Ser Ser Tyr Gly Pro Pro Gly Gln Thr Gly Gly Gly Phe Gly Ala
            100                 105                 110

Gln Gly Ala Pro Gly Ser Ser Phe Gly Pro Gly Gly Phe Gly Gly
            115                 120                 125

Gly Ser Pro Gly Gln Ala Gly Ser Pro Gly Phe Gln Arg Pro Ser Ser
    130                 135                 140

Ser Tyr Gly Pro Pro Gly Gln Ser Pro Gly Gly Gly Phe Ser Gln Gln
145                 150                 155                 160

Gly Gly Ala Pro Gly Ala Ser Gln Arg Pro Ser Ser Thr Tyr Gly Ala
                165                 170                 175

Pro Gly Gln Gly Ala Gly Gly Phe Gly Gln Gly Gly Ser Gly Gly Phe
            180                 185                 190

Gly Gly Thr Gly Gly Ser Val Ala Ile Gly Gly Arg Pro Ser Ser Ser
            195                 200                 205

Tyr Gly Ala Pro Gly Gln Gly Ser Ser Gly Gly Phe Gly Gly Gly Ser
    210                 215                 220

Gly Gly Phe Gly Ser Gln Ala Pro Ser Thr Ser Tyr Gly Ala Pro Gly
225                 230                 235                 240

Gln Gly Ser Pro Gly Gly Gly Phe Gly Ser Gln Gly Gly Pro Gly Gly
                245                 250                 255

Gln Pro Gly Ser Pro Gly Phe Gly Gly Ser Gln Arg Pro Ser Ser Ser
            260                 265                 270

Tyr Gly Pro Pro Gly Gln Gly Gly Ala Pro Gly Gln Gly Gly Ser Pro
    275                 280                 285

Gly Phe Gly Ala Ser Ser Arg Ser Gly Gly Ala Gly Gly Phe Gly Ala
            290                 295                 300

Ser Gln Gln Pro Ser Ser Ser Tyr Gly Pro Pro Gly Gln Gly Ala Gly
305                 310                 315                 320

Ser Gly Phe Gln Gly Thr Gly Gly Gly Phe Gly Gly Pro Gly Gln Arg

```
                    325                 330                 335
Pro Gly Phe Gly Gly Ser Gln Thr Pro Ala Thr Ser Tyr Gly Ala Pro
                340                 345                 350
Gly Gln Ala Gly Gly Ala Ser Gly Gly Phe Gly Gly Ala Gly Ala Gln
                355                 360                 365
Arg Pro Ser Ser Ser Tyr Gly Pro Pro Gly Gln Ala Ser Gly Phe Gly
                370                 375                 380
Gly Gly Ser Ser Gly Gly Phe Gly Gly Ser Ser Gly Gly Phe
385                 390                 395                 400
Gly Gly Asn Gln Gly Gly Phe Gly Gly Asn Gln Gly Gly Phe Gly Gly
                405                 410                 415
Ser Gln Thr Pro Ser Ser Tyr Gly Ala Pro Ser Phe Gly Ser Gly
                420                 425                 430
Gly Ser Pro Gly Ala Ala Gly Gly Ala Gly Gly Phe Gly Gln Gly Gly
                435                 440                 445
Val Gly Gly Ser Gly Gln Pro Gly Gly Phe Gly Gly Asp Gln Gly
                450                 455                 460
Tyr Pro Pro Arg Gly Gly Pro Gly Phe Gly Pro Gly Ser Gly Gly
465                 470                 475                 480
Ser Gly Ala Gly Gly Pro Ile Ala Gly Ser Gly Ser Gly Tyr Pro
                485                 490                 495
Gly Gly Ser Asp Ser Gly Ser Asn Glu Pro Ala Lys Tyr Asp Phe Ser
                500                 505                 510
Tyr Gln Val Asp Asp Pro Ala Ser Gly Thr Ser Phe Gly His Ser Glu
                515                 520                 525
Gln Arg Asp Gly Asp Tyr Thr Ser Gly Gln Tyr Asn Val Leu Leu Pro
                530                 535                 540
Asp Gly Arg Lys Gln Ile Val Glu Tyr Glu Ala Asp Leu Gly Gly Tyr
545                 550                 555                 560
Arg Pro Gln Ile Lys Tyr Glu Gly Gly Ser Ser Gly Ala Gly Gly
                565                 570                 575
Tyr Pro Ser Gly Gly Pro Gly Ser Gln Gly Gly Ala Gly Gly Tyr Pro
                580                 585                 590
Ser Gly Gly Pro Gly Gly Pro Gly Ser Pro Gly Gly Ala Gly Gly Tyr
                595                 600                 605
Gln Ser Gly Ala Ala Gly Gly Ala Gly Gly Tyr Pro Ser Gly Gly Pro
                610                 615                 620
Gly Gly Pro Gly Ala Gly Gly Tyr Pro Ser Gly Gly Pro Gly Gly Pro
625                 630                 635                 640
Gly Ser Gln Ala Gly Gly Phe Ser Gly Gly Phe Gly Gly Gly Ser Asp
                645                 650                 655
Gly Ala Phe Gly Gly Ala Gly Gly Phe Ser Gln Gly Gly Ala Gly Gly
                660                 665                 670
Gly Asp Ala Gly Tyr Pro Arg Gly Gly Pro Gly Gly Phe Gly Gly Ala
                675                 680                 685
Gly Ser Pro Gly Phe Gly Gly Ser Ser Pro Gly Phe Gly Gly Ser
                690                 695                 700
Gly Ser Pro Gly Ala Gln Gly Ser Ser Gly Phe Gly Gly Thr Gly Gly
705                 710                 715                 720
Gly Phe Gly Gly Gly Ala Asp Gly Tyr Pro Arg Gly Gly Pro Gly Ala
                725                 730                 735
Gly Gln Ser Gly Phe Gln Asp Gly Arg Gly Ala Thr Gly Gly Ala Gly
                740                 745                 750
```

Gln Pro Gly Gly Arg Gly Ser Phe Gly Arg Pro Gly Ser Ala Arg Gly
            755                 760                 765

Gly Ser Ser Asn Gly Tyr Ala Asn Gly Gly Ala Glu Gly Tyr Pro
    770                 775                 780

Arg Asp Asn Pro Gln Asn Arg Gly Ser Gly Tyr Ser
785                 790                 795

<210> SEQ ID NO 29
<211> LENGTH: 1051
<212> TYPE: PRT
<213> ORGANISM: Rhodnius prolixus

<400> SEQUENCE: 29

Lys Arg Asp Asp Pro Leu Arg Arg Phe Leu Ala Pro Leu Val Gly Gly
1               5                   10                  15

Gly Asn Gly Ser Gly Gly Gly Gly Gly Tyr Asn Tyr Asn Lys Pro
            20                  25                  30

Ala Asn Gly Leu Ser Leu Pro Gly Gly Gly Ala Leu Pro Pro Ala
        35                  40                  45

Thr Ser Tyr Gly Val Pro Asp Arg Pro Ala Pro Val Pro Ser Ser Pro
50                  55                  60

Pro Ser Ser Ser Tyr Gly Ala Pro Gln Pro Ser Pro Asn Tyr Gly Ala
65                  70                  75                  80

Pro Ser Ser Ser Tyr Gly Ala Pro Ser Gln Gln Pro Ser Arg Ser Tyr
                85                  90                  95

Gly Ala Pro Ser Gln Gly Pro Ser Thr Ser Tyr Ser Gln Arg Pro Ser
            100                 105                 110

Ser Ser Tyr Gly Ala Pro Ala Pro Gln Thr Pro Ser Ser Tyr Gly
        115                 120                 125

Ala Pro Ala Gln Gln Pro Ser Gly Ser Tyr Gly Ala Pro Ser Gly Gly
    130                 135                 140

Gly Gly Ser Ser Gly Tyr Thr Gly Gly Ala Gln Arg Pro Ser Gly Ser
145                 150                 155                 160

Tyr Gly Ala Pro Ser Gln Gly Gly Pro Ser Gly Asn Tyr Gly Pro Pro
                165                 170                 175

Ser Gln Gln Pro Ser Ser Asn Tyr Gly Ala Pro Ser Gln Thr Pro Ser
            180                 185                 190

Ser Asn Tyr Gly Ala Pro Ala Gln Arg Pro Ser Thr Ser Tyr Gly Ala
        195                 200                 205

Pro Ser Gln Pro Pro Ser Ser Ser Tyr Gly Ser Pro Pro Gln Arg Ala
    210                 215                 220

Ser Gly Tyr Pro Ser Ser Ser Gly Pro Ser Asn Gly Tyr Ser Pro
225                 230                 235                 240

Pro Ala Gln Arg Pro Ser Ser Tyr Gly Pro Ser Gln Gln Pro
                245                 250                 255

Ala Ser Ser Tyr Gly Ala Pro Ser Gln Thr Pro Ser Ser Asn Tyr Gly
            260                 265                 270

Pro Pro Ala Pro Ile Pro Ser Ser Asn Tyr Gly Ala Pro Ser Gln Pro
        275                 280                 285

Pro Ser Lys Pro Ser Ala Pro Ser Ser Tyr Gly Thr Pro Ser Gln
    290                 295                 300

Thr Pro Ser Thr Ser Tyr Gly Ala Pro Ser Gln Ala Pro Ser Ser Ser
305                 310                 315                 320

Tyr Gly Ala Pro Ser Arg Pro Ser Pro Pro Ser Ser Ser Tyr Gly Ala

```
                325                 330                 335
Pro Ser Gln Gly Pro Ser Ser Tyr Gly Pro Ser Arg Pro Ser
            340                 345                 350
Gln Pro Ser Ser Pro Ser Ser Gly Tyr Gly Ala Pro Ser Gln Gly Pro
            355                 360                 365
Ser Ser Ser Tyr Gly Ala Pro Ser Arg Pro Ser Ser Pro Ser Ser Ser
    370                 375                 380
Tyr Gly Ala Pro Pro Ser Ser Tyr Gly Ala Pro Ser Arg Pro Ser
385                 390                 395                 400
Pro Pro Ser Ser Tyr Gly Ala Pro Ser Gln Gly Pro Ser Ser Ser
                405                 410                 415
Tyr Gly Pro Pro Ser Arg Pro Ser Gln Pro Ser Ser Pro Ser Ser Gly
            420                 425                 430
Tyr Gly Ala Pro Ser Gln Gly Pro Ser Ser Ser Tyr Gly Ala Pro Ser
            435                 440                 445
Arg Pro Ser Ser Pro Ser Ser Ser Tyr Gly Ala Pro Pro Ser Ser Ser
    450                 455                 460
Tyr Gly Ala Pro Ser Arg Pro Ser Pro Pro Ser Ser Ser Tyr Gly Ala
465                 470                 475                 480
Pro Ser Gln Gly Pro Ser Ser Tyr Gly Pro Pro Ser Arg Pro Ser
                485                 490                 495
Gln Pro Ser Ser Pro Ser Ser Ser Tyr Gly Ala Pro Ser Gln Gly Pro
            500                 505                 510
Ser Ser Ser Tyr Gly Ala Pro Ser Arg Pro Ser Pro Pro Ser Ser Ser
    515                 520                 525
Tyr Gly Ala Pro Ser Gln Gly Pro Ser Ser Ser Tyr Gly Pro Pro Ser
    530                 535                 540
Arg Pro Ser Gln Pro Ser Ser Thr Tyr Gly Val Pro Ser Gly Gly Arg
545                 550                 555                 560
Pro Ser Thr Pro Ser Ser Ser Tyr Gly Ala Pro Pro Gln Ala Leu Ser
                565                 570                 575
Ser Thr Tyr Gly Ala Pro Ser Gly Arg Pro Gly Ala Pro Ser Gln Lys
            580                 585                 590
Pro Ser Ser Ser Tyr Gly Ala Pro Ser Leu Gly Gly Asn Ala Ser Arg
            595                 600                 605
Gly Pro Lys Ser Ser Pro Pro Ser Ser Tyr Gly Ala Pro Ser Val
    610                 615                 620
Gly Thr Ser Val Ser Ser Tyr Ala Pro Ser Gln Gly Ala Gly Gly
625                 630                 635                 640
Phe Gln Ser Ser Arg Pro Ser Ser Tyr Gly Ala Pro Ser Thr Gly
                645                 650                 655
Pro Ser Ser Thr Tyr Gly Pro Pro Ser Gln Pro Pro Ser Ser Ser Tyr
            660                 665                 670
Gly Val Pro Ser Gln Pro Pro Ser Ser Asn Tyr Gly Val Pro Ser Gln
            675                 680                 685
Gly Val Ser Gly Ser Val Gly Ser Ser Pro Ser Ser Ser Tyr Gly
            690                 695                 700
Ala Pro Ser Gln Ile Pro Ser Ser Tyr Gly Ala Pro Ser Gln Ser
705                 710                 715                 720
Ser Ile Gly Gly Phe Gly Ser Ser Arg Pro Ser Ser Tyr Gly Ala
                725                 730                 735
Pro Pro Gln Ala Pro Ser Ser Tyr Ser Ala Pro Leu Arg Ala Pro
                740                 745                 750
```

Ser Thr Ser Tyr Gly Ala Pro Ser Gly Gly Ser Gly Ser Asn Phe Gly
            755                 760                 765

Ser Lys Pro Ser Thr Asn Tyr Gly Ala Pro Ser Gln Pro Pro Ser Thr
    770                 775                 780

Asn Tyr Gly Pro Pro Ser Gln Pro Pro Ser Ser Tyr Gly Thr Pro
785                 790                 795                 800

Ser Arg Ala Pro Ser Pro Thr Tyr Ser Thr Pro Gln Ser Ser Gly Thr
                805                 810                 815

Ser Phe Gly Ser Arg Pro Ser Ser Tyr Gly Val Pro Ser Gln Pro
                820                 825                 830

Thr Thr Asn Tyr Gly Ala Pro Ser Gln Thr Pro Ser Ser Asn Tyr Gly
            835                 840                 845

Ala Pro Pro Ala Ser Ser Ala Pro Ser Ser Thr Tyr Gly Arg Pro Ser
850                 855                 860

Gln Ser Pro Ser Ser Ser Tyr Gly Ala Pro Ser Pro Ser Ser Ser
865                 870                 875                 880

Ser Ser Tyr Glu Ser Pro Ser Gln Pro Pro Ser Ser Tyr Gly Ala
                885                 890                 895

Pro Ser Gln Gly Pro Ser Ser Tyr Gly Ala Pro Ser Arg Pro Ser
                900                 905                 910

Ser Thr Tyr Gly Ala Pro Ser Pro Ser Ser Pro Ser Thr Asn Tyr Gly
            915                 920                 925

Ala Pro Ala Pro Ser Ser Asn Tyr Gly Thr Pro Ala Gln Asp Leu Thr
            930                 935                 940

Gly Ser Tyr Ala Ala Pro Ser Gln Pro Pro Ser Ala Gly Tyr Gly Ala
945                 950                 955                 960

Pro Ser Gly Gln Pro Ser Ser Gly Gly Lys Gln Asn Phe Gln Val Lys
                965                 970                 975

Asn Pro Phe Ala Gly Gln Thr His Gln Val Tyr Pro Ala Val Ser Ser
                980                 985                 990

Ile Ser Phe Gly Leu Pro Ser Gln  Ser Phe Asn Thr Ala  Ile Gln Gly
            995                 1000                 1005

Gln Glu  Pro Ser Gln Ser Tyr  Gly Ala Pro Thr Ala  Ser Ser Pro
       1010                 1015                 1020

Ser Ser  Ser Tyr Gly Ala Pro  Thr Gly Thr Gly Ser  Ser Gln Pro
       1025                 1030                 1035

Gly Gln  Ser Tyr Ala Ser Asn  Gly Gly Tyr Ser Tyr  Ser
       1040                 1045                 1050

<210> SEQ ID NO 30
<211> LENGTH: 506
<212> TYPE: PRT
<213> ORGANISM: Rhodnius prolixus

<400> SEQUENCE: 30

Gln Pro Pro Phe Asn His Tyr Leu Pro Ala Ala Arg Gly Ser Gly Ser
1               5                   10                  15

Asn Ser Ala Gln Tyr Thr Ala Pro Ser Ser Lys Phe Gly Thr Ser Thr
            20                  25                  30

Gly Gln Tyr Gly Gln Pro Pro Ser Glu Val Pro Arg Gly Leu Gln Gln
        35                  40                  45

Gly Ser Tyr Ala Glu Asp Val His Ser Ser Arg Ser Val Asn Pro Ser
    50                  55                  60

Ser Gln Asn Gly Ile Pro Ser Gly His Phe Ser Ser Leu Ser Ser Asn

```
                65                  70                  75                  80
Tyr Gly Ala Pro Ser Ser Asp Tyr Ser Arg Ser Phe Leu Arg Tyr Gly
                    85                  90                  95

Thr Leu Ser Asn Lys Tyr Gly Val Pro Asn Ser Ala Leu Gly Ser Leu
                100                 105                 110

Ser Ser Arg Asn Asn Lys Thr Pro Ala Thr Gln Leu Ser Tyr Gln Pro
            115                 120                 125

Ser Ser His Tyr Asp Ser Arg Ser Thr Ser Glu Asp Gln Phe Ile Ser
        130                 135                 140

Ser Arg Val Ser Asp Ser Gln Tyr Gly Ala Ser Ser Val Arg Arg Phe
145                 150                 155                 160

Leu Pro Ser Ser Gln Tyr Ser Thr Pro Ser Ser Gln Tyr Gly Thr Pro
                165                 170                 175

Ser Ser Gln Tyr Gly Thr Pro Ser Ser Gln Tyr Gly Thr Pro Ser Ser
            180                 185                 190

Gln Tyr Gly Thr Pro Ser Ser Gln Tyr Gly Thr Pro Ser Ser Gln Tyr
        195                 200                 205

Gly Thr Pro Ser Ser Gln Tyr Gly Thr Pro Ser Ser Gln Tyr Gly Thr
    210                 215                 220

Pro Ser Ser Gln Tyr Gly Thr Pro Ser Ser Gln Tyr Gly Thr Pro Ser
225                 230                 235                 240

Ser Pro Pro Ser Gln Tyr Gly Pro Tyr Ser Met Arg Thr Ser Ala
                245                 250                 255

Pro Asn Ser Gln Tyr Gly Thr Pro Ser Ser Phe Arg Thr Ser Pro Ser
                260                 265                 270

Ser Gln Phe Gly Ser Ser Ser Ala His Ser Ser Ser Leu Ser Lys Phe
            275                 280                 285

Arg Ser Val Pro Ser Ser Pro Tyr Gly Thr Leu Ser Ala Ile Arg Ser
        290                 295                 300

Thr His Ser Ser Gln Tyr Gly Thr Pro Ser Ser Phe Ser Asp Ser Thr
305                 310                 315                 320

Ser Ser Ser His Asn Gly Leu Pro Ser His Tyr Pro Gly Ser Gly Phe
                325                 330                 335

Ser Gly Ser Ser Val Asn Asp Gln Lys Ser Tyr Thr Gly Asn Val Phe
            340                 345                 350

Gly Gln Ser His Ser Arg Val Ala Asn Gly Asp Gln His Ala Arg Ser
        355                 360                 365

Tyr Thr Leu Ala Gly Gly Asn Glu Ile Ser Glu Pro Ala Lys Tyr Asp
    370                 375                 380

Phe Asn Tyr Asp Val Ser Asp Gly Glu Gln Gly Val Glu Phe Gly Gln
385                 390                 395                 400

Glu Glu Ser Arg Asp Gly Glu Glu Thr Asn Gly Ser Tyr His Val Leu
                405                 410                 415

Leu Pro Asp Gly Arg Arg Gln Arg Val Gln Tyr Thr Ala Gly Gln Tyr
            420                 425                 430

Gly Tyr Lys Pro Thr Ile Ser Tyr Glu Asn Thr Gly Thr Leu Thr Thr
        435                 440                 445

Gly Arg Gln Gln Phe Ser Asn Gly Phe Tyr Asn Val Gln Gln Ser Gly
    450                 455                 460

Ser Glu Ser Gln Glu His Leu Gly Arg Ser Thr Gly Gln Asn Ser Tyr
465                 470                 475                 480

Gly Gly Ser Asn Gly Tyr Glu Ser Gly Val Gly Tyr Gln Ser Gly Val
                485                 490                 495
```

```
Gly Arg Arg Ser Arg Pro Ala Gly Ser Tyr
            500                 505

<210> SEQ ID NO 31
<211> LENGTH: 551
<212> TYPE: PRT
<213> ORGANISM: Solenopsis invicta

<400> SEQUENCE: 31

Arg Ser Glu Pro Pro Ile Asn Ser Tyr Leu Pro Pro Arg Ala Gly Ser
1               5                   10                  15

Ser Gly Ala Asn Gly Gly Arg Thr Asp Leu Thr Thr Gln Tyr Gly Ala
            20                  25                  30

Pro Asp Phe Asn Asn Gly Gly Ala Thr Ser Phe Ser Gly Asn Gly
            35                  40                  45

Ala Gly Asp Gly Pro Ser Lys Leu Tyr Asp Val Pro Val Arg Gly Asn
50              55                  60

Ala Gly Gly Asn Gly Leu Gly Arg Gly Asn Gly Phe Gly Gly Gly Gln
65                  70                  75                  80

Pro Ser Ser Ser Tyr Gly Ala Pro Asn Gly Gly Ser Asn Glu Asn Arg
                85                  90                  95

Gly Asn Gly Gly Arg Pro Ser Thr Ser Tyr Gly Val Pro Gly Ala Asn
            100                 105                 110

Gly Asn Asn Gly Gly Gly Phe Gly Asn Gly Gly Asp Lys Gly Arg Pro
            115                 120                 125

Ser Thr Ser Tyr Gly Val Pro Asp Ala Ser Gly Ser Ser Gln Gly Ser
130                 135                 140

Phe Gly Asn Val Gly Asn Gly Gly Arg Pro Ser Thr Asn Tyr Gly Val
145                 150                 155                 160

Pro Gly Ala Asn Gly Asn Gly Gly Phe Gly Asn Ala Ala Asn Glu
            165                 170                 175

Gly Lys Pro Ser Thr Ser Tyr Gly Val Pro Gly Ala Asn Gly Asn Ser
            180                 185                 190

Gln Gly Gly Phe Gly Asn Gly Gly Arg Pro Ser Thr Gly Tyr Gly Val
            195                 200                 205

Pro Gly Ala Asn Gly Asn Asn Gly Gly Phe Gly Gly Arg Pro Ser
210                 215                 220

Thr Ser Tyr Gly Ala Pro Gly Ala Asn Gly Asn His Arg Gly Gly Asn
225                 230                 235                 240

Gly Gly Asn Ala Ser Pro Ser Thr Asn Tyr Gly Val Pro Gly Gly Asn
            245                 250                 255

Asn Gly Asn Thr Asn Gly Lys Gly Arg Phe Asn Gly Gly Asn Ser Gly
            260                 265                 270

Gly Gly Pro Ser Asn Asn Tyr Gly Val Pro Asn Glu Asn Ala Phe Gly
            275                 280                 285

Gly Gly Leu Ser Thr Ser Tyr Gly Pro Pro Ser Arg Gly Gly Asn Gly
            290                 295                 300

Asn Ser Gly Tyr Pro Ser Gly Gly Ser Asn Gly Gly Ser Phe Val Asn
305                 310                 315                 320

Asn Gly Ala Asn Gly Tyr Pro Ser Gly Gly Pro Asn Gly Asn Ala Gly
            325                 330                 335

Asn Phe Gly Asp Gly Arg Gly Gly Lys Gly Gly Gly Ser Ser Gly Glu
            340                 345                 350

Gly Tyr Asn Asp Asn Ala Gln Glu Gly Ser Thr Glu Pro Ala Lys Tyr
```

355                 360                 365
Glu Phe Ser Tyr Lys Val Lys Asp Gln Gln Thr Gly Ser Glu Tyr Ser
370                 375                 380

His Thr Glu Thr Arg Asp Gly Asp Arg Ala Gln Gly Glu Phe Asn Val
385                 390                 395                 400

Leu Leu Pro Asp Gly Arg Lys Gln Ile Val Glu Tyr Glu Ala Asp Gln
                405                 410                 415

Asp Gly Phe Lys Pro Gln Ile Arg Tyr Glu Gly Glu Ala Asn Ala Gly
            420                 425                 430

Gly Gly Tyr Ser Ser Gly Gly Ser Asn Asp Asn Asn Asp Gly Tyr Ser
        435                 440                 445

Ser Gly Arg Pro Gly Ser Glu Ala Gly Gly Phe Ala Asn Asn Ser Gly
    450                 455                 460

Phe Asn Gly Ser Gly Thr Asn Gly Gly Arg Ser Ser Gly Gly Pro Gly
465                 470                 475                 480

Asp Gly Asn Pro Gly Gly Phe Asn Ser Gly Gly Gly Gly Tyr Gln
                485                 490                 495

Ser Gly Arg Pro Ala Gly Gln Ser Phe Gly Arg Asp Asn Asp Gly Gly
            500                 505                 510

Leu Ser Gly Asp Ile Gly Gly Tyr Phe Ala Asn Ser Pro Ser Asn Asn
        515                 520                 525

Ile Gly Gly Ser Asp Ser Ala Asn Val Gly Ser Asn Arg Gln Asn Gly
    530                 535                 540

Gly Asn Gly Gly Tyr Gln Tyr
545                 550

<210> SEQ ID NO 32
<211> LENGTH: 382
<212> TYPE: PRT
<213> ORGANISM: Culex quinquefasciatus

<400> SEQUENCE: 32

Lys Arg Glu Ala Pro Leu Pro Gly Gly Ser Tyr Leu Pro Pro Ser Asn
1               5                   10                  15

Gly Gly Gly Ala Gly Gly Tyr Pro Ala Ala Gly Pro Pro Ser Gly Ser
            20                  25                  30

Tyr Gly Pro Pro Ser Asn Gly Asn Gly Asn Gly Ala Gly Gly
        35                  40                  45

Tyr Pro Ser Ala Pro Ser Gln Gln Tyr Gly Ala Pro Ala Gly Gly Ala
    50                  55                  60

Pro Ser Gln Gln Tyr Gly Ala Pro Ser Asn Gly Asn Gly Gly Ala Gly
65                  70                  75                  80

Gly Tyr Pro Ser Ala Pro Ser Gln Gln Tyr Gly Ala Pro Asn Gly Asn
            85                  90                  95

Gly Asn Gly Gly Phe Gly Gly Arg Pro Gln Ala Pro Ser Gln Gln Tyr
        100                 105                 110

Gly Ala Pro Ser Asn Gly Asn Gly Gly Ala Arg Pro Ser Gln Gln Tyr
    115                 120                 125

Gly Ala Pro Asn Gly Gly Asn Gly Asn Gly Arg Pro Gln Thr Pro Ser
130                 135                 140

Ser Gln Tyr Gly Ala Pro Ser Gly Gly Ala Pro Ser Ser Gln Tyr Gly
145                 150                 155                 160

Ala Pro Ser Gly Gly Ala Pro Ser Gln Gln Tyr Gly Ala Pro Asn Gly
            165                 170                 175

Gly Asn Gly Asn Gly Arg Pro Gln Thr Pro Ser Ser Gln Tyr Gly Ala
            180                 185                 190

Pro Ser Gly Gly Ala Pro Ser Gln Gln Tyr Gly Ala Pro Asn Gly Gly
        195                 200                 205

Asn Gly Asn Gly Arg Pro Gln Thr Pro Ser Ser Gln Tyr Gly Ala Pro
        210                 215                 220

Ser Gly Gly Ala Pro Ser Ser Gln Tyr Gly Ala Pro Ser Gly Gly Ala
225                 230                 235                 240

Pro Ser Ser Gln Tyr Gly Ala Pro Ala Gly Gly Ala Pro Ser Ser Gln
            245                 250                 255

Tyr Gly Ala Pro Ala Gly Gly Ala Pro Ser Ser Gln Tyr Gly Ala Pro
            260                 265                 270

Ala Gly Gly Ala Pro Ser Ser Gln Tyr Gly Ala Pro Ala Gly Gly Ala
            275                 280                 285

Pro Ser Ser Gln Tyr Gly Ala Pro Ala Gly Gly Ala Pro Ser Ser Gln
            290                 295                 300

Tyr Gly Ala Pro Ser Ser Gln Tyr Gly Ala Pro Ala Gly Gly Ala Pro
305                 310                 315                 320

Ser Ser Gln Tyr Gly Ala Pro Ala Gly Gly Ala Pro Ser Ser Gln Tyr
            325                 330                 335

Gly Ala Pro Ser Gly Gly Ala Pro Ser Ser Gln Tyr Gly Ala Pro Ser
            340                 345                 350

Gly Gly Ala Pro Ser Ser Gln Tyr Gly Ala Pro Ala Gly Gly Ala Pro
            355                 360                 365

Ser Ser Gln Tyr Gly Ala Pro Ser Gly Gly Ala Pro Ser Ser
            370                 375                 380

<210> SEQ ID NO 33
<211> LENGTH: 491
<212> TYPE: PRT
<213> ORGANISM: Bactrocera cucurbitae

<400> SEQUENCE: 33

Arg Pro Glu Pro Pro Val Asn Ser Tyr Leu Pro Pro Ser Ala Asn Gly
1               5                   10                  15

Asn Gly Asn Gly Gly Gly Arg Pro Ser Ser Gln Tyr Gly Ala Pro Gly
            20                  25                  30

Leu Gly Ser Asn Ser Asn Gly Asn Gly Asn Gly Asn Gly Gly Gly Arg
            35                  40                  45

Pro Ser Ser Gln Tyr Gly Val Pro Gly Leu Gly Asn Gly Asn Gly Asn
        50                  55                  60

Asn Gly Asn Gly Gly Gly Gly Arg Pro Ser Ser Tyr Gly Ala
65                  70                  75                  80

Pro Gly Leu Gly Gly Asn Gly Asn Gly Asn Gly Asn Gly Gly Gly Arg
            85                  90                  95

Pro Ser Ser Gln Tyr Gly Val Pro Gly Leu Gly Asn Gly Asn Gly
            100                 105                 110

Asn Gly Asn Gly Asn Gly Gly Gly Arg Pro Ser Ser Thr Tyr Gly Ala
        115                 120                 125

Pro Gly Leu Arg Gly Asn Gly Asn Gly Asn Gly Asn Gly Asn Gly Arg
            130                 135                 140

Pro Ser Ser Thr Tyr Gly Ala Pro Gly Leu Gly Gly Asn Gly Asn Gly
145                 150                 155                 160

Asn Gly Asn Gly Asn Gly Arg Pro Ser Ser Thr Tyr Gly Ala Pro Gly
            165                 170                 175

-continued

Leu Gly Gly Asn Gly Asn Gly Asn Gly Asn Gly Arg Pro Ser
                180             185             190

Ser Thr Tyr Gly Ala Pro Gly Leu Asn Gly Asn Gly Leu Gly Gly Gly
            195                 200             205

Gln Lys Pro Ser Asp Ser Tyr Gly Pro Pro Ala Ser Gly Asn Gly Asn
210                 215                 220

Gly Tyr Ser Asn Gly Asn Gly Asn Gly Asn Gly Gly Arg Pro
225                 230             235                 240

Gly Gln Glu Tyr Leu Pro Pro Gly Arg Asn Gly Asn Gly Asn Gly Asn
                245             250             255

Gly Gly Arg Gly Asn Gly Asn Gly Gly Ala Asn Gly Tyr Asp Tyr
            260             265             270

Ser Gln Gly Gly Ser Asp Ser Gly Glu Ser Gly Ile Val Asp Tyr Glu
    275             280             285

Ala Asp Gln Gly Gly Tyr Arg Pro Gln Ile Arg Tyr Glu Gly Glu Ala
290                 295             300

Asn Asn Gly Ala Gly Gly Leu Gly Gly Ala Gly Gly Ala Asn Gly
305             310             315             320

Tyr Asp Tyr Glu Gln Asn Gly Asn Gly Leu Gly Gly Asn Gly Tyr
            325             330             335

Ser Asn Gly Gln Asp Leu Gly Ser Asn Gly Tyr Ser Ser Gly Arg Pro
        340             345             350

Asn Gly Asn Gly Asn Gly Asn Gly Asn Gly Asn Gly Tyr Ser
            355             360             365

Gly Arg Asn Gly Lys Gly Arg Asn Gly Asn Gly Gln Gly Leu
    370             375             380

Gly Arg Asn Gly Tyr Ser Asp Gly Arg Pro Ser Gly Gln Asp Leu Gly
385             390             395             400

Asp Asn Gly Tyr Ala Ser Gly Arg Pro Gly Gly Asn Gly Asn Gly Asn
            405             410             415

Gly Gly Asn Gly Asn Gly Tyr Ser Asn Gly Asn Gly Tyr Ser Asn Gly
            420             425             430

Asn Gly Asn Gly Thr Gly Asn Gly Gly Gln Tyr Asn Gly Asn Gly
            435             440             445

Asn Gly Tyr Ser Asp Gly Arg Pro Gly Gly Gln Asp Asn Leu Asp Gly
450                 455             460

Gln Gly Tyr Ser Ser Gly Arg Pro Asn Gly Phe Gly Pro Gly Gly Gln
465             470             475             480

Asn Gly Asp Asn Asp Gly Asn Gly Tyr Arg Tyr
            485             490

<210> SEQ ID NO 34
<211> LENGTH: 770
<212> TYPE: PRT
<213> ORGANISM: Trichogramma pretiosum

<400> SEQUENCE: 34

Arg Pro Glu Pro Pro Val Asn Ser Tyr Leu Pro Pro Gly Gln Gly Gly
1               5                   10                  15

Gln Gly Gly Phe Gly Gly Ser Gly Arg Pro Gly Gly Ser Pro
            20                  25                  30

Ser Asn Gln Tyr Gly Pro Pro Asn Phe Gln Asn Gly Gly Gln Asn
        35                  40                  45

Gly Gly Ser Gly Phe Gly Gly Asn Gly Asn Gly Asn Ser Phe Gly Pro

```
                50                  55                  60
Pro Ser Asn Ser Tyr Gly Pro Pro Glu Phe Gly Ser Pro Gly Ala Gly
 65                  70                  75                  80

Ser Phe Gly Gly Gly Arg Pro Gln Asp Thr Tyr Gly Pro Pro Ser Asn
                     85                  90                  95

Gly Asn Gly Asn Gly Asn Gly Phe Gly Gly Asn Gly Asn Gly Gly Gly
                100                 105                 110

Arg Pro Ser Ser Arg Pro Ser Asp Ser Tyr Gly Pro Pro Ser Ser Gly
                115                 120                 125

Asn Gly Phe Gly Gly Gly Asn Ser Gly Arg Pro Ser Glu Ser Tyr Gly
                130                 135                 140

Pro Pro Gln Asn Gly Gly Ser Gly Asn Gly Asn Gln Gly Gly Gly
145                 150                 155                 160

Asn Gly Phe Gly Asn Gly Gly Arg Gly Gln Gly Lys Pro Ser
                165                 170                 175

Asp Ser Tyr Gly Pro Pro Asn Ser Gly Asn Arg Pro Gly Ser Ser Asn
                180                 185                 190

Gly Gly Gly Gln Gln Gln Asn Gly Phe Gly Gly Asn Gly Gly Arg
                195                 200                 205

Pro Ser Asn Thr Tyr Gly Pro Pro Gly Gly Gly Asn Gly Gly Gly Arg
                210                 215                 220

Pro Gly Gly Ser Gly Gly Phe Gly Gly Gln Asn Gly Gly Arg Pro
225                 230                 235                 240

Ser Asp Ser Tyr Gly Pro Pro Ser Asn Gly Asn Gly Asn Gly Arg
                245                 250                 255

Pro Ser Asn Asn Tyr Gly Pro Pro Asn Ser Gly Gly Asn Gly Asn
                260                 265                 270

Gly Phe Gly Gly Ser Asn Gly Lys Pro Ser Asn Ser Tyr Gly Pro Pro
                275                 280                 285

Ser Asn Gly Asn Gly Gly Phe Gly Gly Ser Asn Gly Arg Pro Ser
290                 295                 300

Asn Ser Tyr Gly Pro Pro Ser Gly Asn Gly Gly Phe Gly Gly
305                 310                 315                 320

Ser Ser Ala Val Gly Arg Pro Gly Asn Ser Gly Ser Pro Ser Ser Ser
                325                 330                 335

Gly Ser Gly Phe Gly Gly Asn Gly Gly Ala Ser Arg Pro Ser Ser Ser
                340                 345                 350

Tyr Gly Pro Pro Ser Asn Gly Gly Phe Gly Asn Gly Gly Ser
                355                 360                 365

Asn Gly Arg Pro Ser Ser Tyr Gly Pro Pro Asn Ser Gly Ser Asn
370                 375                 380

Gly Gly Gly Phe Gly Gly Gln Asn Gly Asn Arg Gln Asn Gly Asn
385                 390                 395                 400

Asn Gly Gln Gly Gly Phe Gly Gln Pro Ser Ser Ser Tyr Gly Pro
                405                 410                 415

Pro Ser Asn Gly Asn Gly Phe Gly Gly Gly Gly Ser Asn Gly Tyr
                420                 425                 430

Pro Gln Asn Ser Gln Gly Gly Asn Gly Asn Gly Phe Gly Gln Gly Ser
                435                 440                 445

Gly Gly Arg Pro Ser Ser Tyr Gly Pro Ser Asn Gly Gly Gly
450                 455                 460

Gly Gly Asp Asn Gly Tyr Ser Ser Gly Gly Pro Gly Gly Phe Gly Gly
465                 470                 475                 480
```

Gln Pro Gln Asp Ser Tyr Gly Pro Pro Ser Gly Ala Val Asp Gly
                485                 490                 495

Asn Asn Gly Phe Ser Ser Gly Ser Ser Gly Asp Asn Asn Gly Tyr
                500                 505                 510

Ser Ser Gly Gly Pro Gly Gly Asn Gly Phe Glu Asp Gly Asn Asp Glu
                515                 520                 525

Pro Ala Lys Tyr Glu Phe Ser Tyr Glu Val Lys Asp Glu Gln Ser Gly
                530                 535                 540

Ser Ser Phe Gly His Thr Glu Met Arg Asp Gly Asp Arg Ala Gln Gly
545                 550                 555                 560

Glu Phe Asn Val Leu Leu Pro Asp Gly Arg Lys Gln Ile Val Glu Tyr
                565                 570                 575

Glu Ala Asp Gln Asp Gly Phe Lys Pro Gln Ile Arg Tyr Glu Gly Glu
                580                 585                 590

Ala Asn Thr Gly Gly Ala Gly Gly Tyr Pro Ser Gly Gly Pro Gly Gly
                595                 600                 605

Gln Gly Gly Asn Gly Asn Gly Gly Tyr Pro Ser Gly Gly Pro Ser Asn
                610                 615                 620

Gly Gly Phe Gly Gly Gln Asn Gly Gly Asn Gly Gly Tyr Pro Ser
625                 630                 635                 640

Gly Gly Pro Ser Gly Gly Gly Phe Gly Gly Gln Asn Gly Gly Ser Gly
                645                 650                 655

Gly Tyr Pro Ser Gly Gly Pro Ser Gly Gly Gly Phe Gly Gly Gln Gly
                660                 665                 670

Gly Phe Gly Gly Gln Asn Ser Gly Gly Asn Gly Gly Tyr Ser Ser Gly
                675                 680                 685

Gly Pro Ala Ser Gly Gly Phe Gly Gly Gln Asn Gly Gly Asn Gly Gly
                690                 695                 700

Tyr Pro Ser Gly Gly Pro Ser Gly Gly Gly Phe Gly Gly Gln Gly Gly
705                 710                 715                 720

Phe Gly Gly Gln Asn Ser Gly Gly Asn Gly Gly Tyr Pro Ser Gly Gly
                725                 730                 735

Pro Ser Ser Gly Gly Phe Gly Gly Gln Asn Gly Gly Gly Gly Asn
                740                 745                 750

Tyr Pro Ala Gly Ser Gly Gly Asp Ala Glu Ala Asn Gly Gly Tyr Gln
                755                 760                 765

Tyr Ser
770

<210> SEQ ID NO 35
<211> LENGTH: 280
<212> TYPE: PRT
<213> ORGANISM: Drosophila sechellia

<400> SEQUENCE: 35

Gln Ser Gly Ala Gly Gly Arg Pro Ser Asp Thr Tyr Gly Ala Pro Gly
1               5                   10                  15

Gly Gly Asn Gly Gly Arg Pro Ser Asp Ser Tyr Gly Ala Pro Gly Gln
                20                  25                  30

Gly Gln Gly Gln Gly Gln Gly Gly Tyr Gly Gly Lys Pro Ser
                35                  40                  45

Asp Ser Tyr Gly Ala Pro Gly Gly Asn Gly Asn Gly Gly Arg Pro
                50                  55                  60

Ser Ser Ser Tyr Gly Ala Pro Gly Gly Gly Asn Gly Gly Arg Pro Ser

```
                65                  70                  75                  80
Asp Thr Tyr Gly Ala Pro Gly Gly Asn Gly Gly Arg Pro Ser Asp
                    85                  90                  95

Thr Tyr Gly Ala Pro Gly Gly Gly Asn Gly Asn Gly Gly Arg Pro
            100                 105                 110

Ser Ser Ser Tyr Gly Ala Pro Gly Gln Gly Gln Gly Asn Gly Asn
            115                 120                 125

Gly Arg Pro Ser Ser Ser Tyr Gly Ala Pro Gly Gly Asn Gly Gly
        130                 135                 140

Arg Pro Ser Asp Thr Tyr Gly Ala Pro Gly Gly Gly Asn Gly Gly Arg
145                 150                 155                 160

Pro Ser Asp Thr Tyr Gly Ala Pro Gly Gly Asn Asn Gly Gly Arg
                165                 170                 175

Pro Ser Ser Ser Tyr Gly Ala Pro Gly Gly Asn Gly Arg Pro
            180                 185                 190

Ser Asp Thr Tyr Gly Ala Pro Gly Gly Asn Gly Asn Gly Ser Gly
                195                 200                 205

Gly Arg Pro Ser Ser Ser Tyr Gly Ala Pro Ala Gln Gly Gln Gly Gly
        210                 215                 220

Phe Gly Gly Arg Pro Ser Asp Ser Tyr Gly Ala Pro Gly Gln Asn Gln
225                 230                 235                 240

Lys Pro Ser Asp Ser Tyr Gly Ala Pro Gly Ser Gly Asn Gly Ser Ala
                245                 250                 255

Gly Arg Pro Ser Ser Ser Tyr Gly Ala Pro Gly Ser Gly Pro Gly Gly
        260                 265                 270

Arg Pro Ser Asp Ser Tyr Gly Pro
        275                 280

<210> SEQ ID NO 36
<211> LENGTH: 280
<212> TYPE: PRT
<213> ORGANISM: Drosophila sechellia

<400> SEQUENCE: 36

Gln Ser Gly Ala Gly Gly Arg Pro Ser Asp Thr Tyr Gly Ala Pro Gly
1               5                   10                  15

Gly Gly Asn Gly Gly Arg Pro Ser Asp Ser Tyr Gly Ala Pro Gly Gln
            20                  25                  30

Gly Gln Gly Gln Gly Gln Gly Gln Gly Gly Tyr Gly Gly Lys Pro Ser
        35                  40                  45

Asp Ser Tyr Gly Ala Pro Gly Gly Gly Asn Gly Asn Gly Gly Arg Pro
    50                  55                  60

Ser Ser Ser Tyr Gly Ala Pro Gly Gly Gly Asn Gly Gly Arg Pro Ser
65                  70                  75                  80

Asp Thr Tyr Gly Ala Pro Gly Gly Gly Asn Gly Gly Arg Pro Ser Asp
                85                  90                  95

Thr Tyr Gly Ala Pro Gly Gly Gly Asn Gly Asn Gly Gly Arg Pro
            100                 105                 110

Ser Ser Ser Tyr Gly Ala Pro Gly Gln Gly Gln Gly Asn Gly Asn
            115                 120                 125

Gly Arg Pro Ser Ser Ser Tyr Gly Ala Pro Gly Gly Asn Gly Gly
        130                 135                 140

Arg Pro Ser Asp Thr Tyr Gly Ala Pro Gly Gly Gly Asn Gly Gly Arg
145                 150                 155                 160
```

```
Pro Ser Asp Thr Tyr Gly Ala Pro Gly Gly Asn Asn Gly Gly Arg
              165                 170                 175

Pro Ser Ser Ser Tyr Gly Ala Pro Gly Gly Asn Gly Gly Arg Pro
        180                 185                 190

Ser Asp Thr Tyr Gly Ala Pro Gly Gly Asn Gly Asn Gly Ser Gly
            195                 200                 205

Gly Arg Pro Ser Ser Tyr Gly Ala Pro Ala Gln Gly Gln Gly Gly
    210                 215                 220

Phe Gly Gly Arg Pro Ser Asp Ser Tyr Gly Ala Pro Gly Gln Asn Gln
225                 230                 235                 240

Lys Pro Ser Asp Ser Tyr Gly Ala Pro Gly Ser Gly Asn Gly Ser Ala
                245                 250                 255

Gly Arg Pro Ser Ser Ser Tyr Gly Ala Pro Gly Ser Gly Pro Gly Gly
        260                 265                 270

Arg Pro Ser Asp Ser Tyr Gly Pro
        275             280

<210> SEQ ID NO 37
<211> LENGTH: 280
<212> TYPE: PRT
<213> ORGANISM: Drosophila sechellia

<400> SEQUENCE: 37

Gln Ser Gly Ala Gly Gly Arg Pro Ser Asp Thr Tyr Gly Ala Pro Gly
1               5                   10                  15

Gly Gly Asn Gly Gly Arg Pro Ser Asp Ser Tyr Gly Ala Pro Gly Gln
            20                  25                  30

Gly Gln Gly Gln Gly Gln Gly Gly Tyr Gly Lys Pro Ser
        35                  40                  45

Asp Ser Tyr Gly Ala Pro Gly Gly Gly Asn Gly Asn Gly Arg Pro
    50                  55                  60

Ser Ser Ser Tyr Gly Ala Pro Gly Gly Gly Asn Gly Gly Arg Pro Ser
65                  70                  75                  80

Asp Thr Tyr Gly Ala Pro Gly Gly Gly Asn Gly Gly Arg Pro Ser Asp
                85                  90                  95

Thr Tyr Gly Ala Pro Gly Gly Gly Asn Gly Asn Gly Arg Pro
            100                 105                 110

Ser Ser Ser Tyr Gly Ala Pro Gly Gln Gly Gln Gly Asn Gly Asn Gly
            115                 120                 125

Gly Arg Pro Ser Ser Ser Tyr Gly Ala Pro Gly Gly Gly Asn Gly Gly
    130                 135                 140

Arg Pro Ser Asp Thr Tyr Gly Ala Pro Gly Gly Gly Asn Gly Arg
145                 150                 155                 160

Pro Ser Asp Thr Tyr Gly Ala Pro Gly Gly Asn Asn Gly Gly Arg
                165                 170                 175

Pro Ser Ser Ser Tyr Gly Ala Pro Gly Gly Gly Asn Gly Gly Arg Pro
        180                 185                 190

Ser Asp Thr Tyr Gly Ala Pro Gly Gly Gly Asn Gly Asn Gly Ser Gly
            195                 200                 205

Gly Arg Pro Ser Ser Ser Tyr Gly Ala Pro Ala Gln Gly Gln Gly Gly
    210                 215                 220

Phe Gly Gly Arg Pro Ser Asp Ser Tyr Gly Ala Pro Gly Gln Asn Gln
225                 230                 235                 240

Lys Pro Ser Asp Ser Tyr Gly Ala Pro Gly Ser Gly Asn Gly Ser Ala
                245                 250                 255
```

```
Gly Arg Pro Ser Ser Tyr Gly Ala Pro Gly Ser Gly Pro Gly Gly
            260                 265                 270

Arg Pro Ser Asp Ser Tyr Gly Pro
            275                 280

<210> SEQ ID NO 38
<211> LENGTH: 280
<212> TYPE: PRT
<213> ORGANISM: Drosophila sechellia

<400> SEQUENCE: 38

Gln Ser Gly Ala Gly Gly Arg Pro Ser Asp Thr Tyr Gly Ala Pro Gly
1               5                   10                  15

Gly Gly Asn Gly Gly Arg Pro Ser Asp Ser Tyr Gly Ala Pro Gly Gln
            20                  25                  30

Gly Gln Gly Gln Gly Gln Gly Gln Gly Gly Tyr Gly Lys Pro Ser
        35                  40                  45

Asp Ser Tyr Gly Ala Pro Gly Gly Asn Gly Asn Gly Gly Arg Pro
    50                  55                  60

Ser Ser Ser Tyr Gly Ala Pro Gly Gly Asn Gly Gly Arg Pro Ser
65                  70                  75                  80

Asp Thr Tyr Gly Ala Pro Gly Gly Asn Gly Gly Arg Pro Ser Asp
                85                  90                  95

Thr Tyr Gly Ala Pro Gly Gly Gly Asn Gly Asn Gly Gly Arg Pro
                100                 105                 110

Ser Ser Ser Tyr Gly Ala Pro Gly Gln Gly Gln Gly Asn Gly Asn Gly
            115                 120                 125

Gly Arg Pro Ser Ser Ser Tyr Gly Ala Pro Gly Gly Gly Asn Gly Gly
            130                 135                 140

Arg Pro Ser Asp Thr Tyr Gly Ala Pro Gly Gly Gly Asn Gly Arg
145                 150                 155                 160

Pro Ser Asp Thr Tyr Gly Ala Pro Gly Gly Gly Asn Asn Gly Gly Arg
                165                 170                 175

Pro Ser Ser Ser Tyr Gly Ala Pro Gly Gly Gly Asn Gly Gly Arg Pro
            180                 185                 190

Ser Asp Thr Tyr Gly Ala Pro Gly Gly Gly Asn Gly Asn Gly Ser Gly
            195                 200                 205

Gly Arg Pro Ser Ser Ser Tyr Gly Ala Pro Ala Gln Gly Gln Gly Gly
            210                 215                 220

Phe Gly Gly Arg Pro Ser Asp Ser Tyr Gly Ala Pro Gly Gln Asn Gln
225                 230                 235                 240

Lys Pro Ser Asp Ser Tyr Gly Ala Pro Gly Ser Gly Asn Gly Ser Ala
                245                 250                 255

Gly Arg Pro Ser Ser Tyr Gly Ala Pro Gly Ser Gly Pro Gly Gly
            260                 265                 270

Arg Pro Ser Asp Ser Tyr Gly Pro
            275                 280

<210> SEQ ID NO 39
<211> LENGTH: 162
<212> TYPE: PRT
<213> ORGANISM: Drosophila sechellia

<400> SEQUENCE: 39

Tyr Ser Ser Gly Arg Pro Gly Asn Gly Asn Gly Asn Gly Asn Gly Gly
1               5                   10                  15
```

Tyr Ser Ser Gly Arg Pro Gly Gly Gln Asp Leu Gly Pro Ser Gly Tyr
            20                  25                  30

Ser Gly Gly Arg Pro Gly Gly Gln Asp Leu Gly Ala Gly Gly Tyr Ser
        35                  40                  45

Asn Val Lys Pro Gly Gly Gln Asp Leu Gly Pro Gly Gly Tyr Ser Gly
    50                  55                  60

Gly Arg Pro Gly Gly Gln Asp Leu Gly Arg Asp Gly Tyr Ser Gly Gly
65                  70                  75                  80

Arg Pro Gly Gly Gln Asp Leu Gly Ala Gly Ala Tyr Ser Asn Gly Arg
                85                  90                  95

Pro Gly Gly Asn Gly Asn Gly Ser Asp Gly Gly Arg Val Ile Ile
            100                 105                 110

Gly Gly Arg Val Ile Gly Gly Gln Asp Gly Gly Asp Gln Gly Tyr Ser
        115                 120                 125

Gly Gly Arg Pro Gly Gly Gln Asp Leu Gly Arg Asp Gly Tyr Ser Ser
    130                 135                 140

Gly Arg Pro Gly Gly Arg Pro Gly Gly Asn Gly Gln Asp Ser Gln Asp
145                 150                 155                 160

Gly Gln

<210> SEQ ID NO 40
<211> LENGTH: 162
<212> TYPE: PRT
<213> ORGANISM: Drosophila sechellia

<400> SEQUENCE: 40

Tyr Ser Ser Gly Arg Pro Gly Asn Gly Asn Gly Asn Gly Asn Gly Gly
1               5                   10                  15

Tyr Ser Ser Gly Arg Pro Gly Gly Gln Asp Leu Gly Pro Ser Gly Tyr
            20                  25                  30

Ser Gly Gly Arg Pro Gly Gly Gln Asp Leu Gly Ala Gly Gly Tyr Ser
        35                  40                  45

Asn Val Lys Pro Gly Gly Gln Asp Leu Gly Pro Gly Gly Tyr Ser Gly
    50                  55                  60

Gly Arg Pro Gly Gly Gln Asp Leu Gly Arg Asp Gly Tyr Ser Gly Gly
65                  70                  75                  80

Arg Pro Gly Gly Gln Asp Leu Gly Ala Gly Ala Tyr Ser Asn Gly Arg
                85                  90                  95

Pro Gly Gly Asn Gly Asn Gly Ser Asp Gly Gly Arg Val Ile Ile
            100                 105                 110

Gly Gly Arg Val Ile Gly Gly Gln Asp Gly Gly Asp Gln Gly Tyr Ser
        115                 120                 125

Gly Gly Arg Pro Gly Gly Gln Asp Leu Gly Arg Asp Gly Tyr Ser Ser
    130                 135                 140

Gly Arg Pro Gly Gly Arg Pro Gly Gly Asn Gly Gln Asp Ser Gln Asp
145                 150                 155                 160

Gly Gln

<210> SEQ ID NO 41
<211> LENGTH: 162
<212> TYPE: PRT
<213> ORGANISM: Drosophila sechellia

<400> SEQUENCE: 41

Tyr Ser Ser Gly Arg Pro Gly Asn Gly Asn Gly Asn Gly Asn Gly Gly

```
                1               5                   10                  15
Tyr Ser Ser Gly Arg Pro Gly Gly Gln Asp Leu Gly Pro Ser Gly Tyr
                20                  25                  30

Ser Gly Gly Arg Pro Gly Gly Gln Asp Leu Gly Ala Gly Gly Tyr Ser
                35                  40                  45

Asn Val Lys Pro Gly Gly Gln Asp Leu Gly Pro Gly Gly Tyr Ser Gly
                50                  55                  60

Gly Arg Pro Gly Gly Gln Asp Leu Gly Arg Asp Gly Tyr Ser Gly Gly
65                  70                  75                  80

Arg Pro Gly Gly Gln Asp Leu Gly Ala Gly Ala Tyr Ser Asn Gly Arg
                85                  90                  95

Pro Gly Gly Asn Gly Asn Gly Ser Asp Gly Gly Arg Val Ile Ile
                100                 105                 110

Gly Gly Arg Val Ile Gly Gly Gln Asp Gly Gly Asp Gln Gly Tyr Ser
                115                 120                 125

Gly Gly Arg Pro Gly Gly Gln Asp Leu Gly Arg Asp Gly Tyr Ser Ser
                130                 135                 140

Gly Arg Pro Gly Gly Arg Pro Gly Gly Asn Gly Gln Asp Ser Gln Asp
145                 150                 155                 160

Gly Gln
```

<210> SEQ ID NO 42
<211> LENGTH: 162
<212> TYPE: PRT
<213> ORGANISM: Drosophila sechellia

<400> SEQUENCE: 42

```
Tyr Ser Ser Gly Arg Pro Gly Asn Gly Asn Gly Asn Gly Asn Gly Gly
1               5                   10                  15

Tyr Ser Ser Gly Arg Pro Gly Gly Gln Asp Leu Gly Pro Ser Gly Tyr
                20                  25                  30

Ser Gly Gly Arg Pro Gly Gly Gln Asp Leu Gly Ala Gly Gly Tyr Ser
                35                  40                  45

Asn Val Lys Pro Gly Gly Gln Asp Leu Gly Pro Gly Gly Tyr Ser Gly
                50                  55                  60

Gly Arg Pro Gly Gly Gln Asp Leu Gly Arg Asp Gly Tyr Ser Gly Gly
65                  70                  75                  80

Arg Pro Gly Gly Gln Asp Leu Gly Ala Gly Ala Tyr Ser Asn Gly Arg
                85                  90                  95

Pro Gly Gly Asn Gly Asn Gly Ser Asp Gly Gly Arg Val Ile Ile
                100                 105                 110

Gly Gly Arg Val Ile Gly Gly Gln Asp Gly Gly Asp Gln Gly Tyr Ser
                115                 120                 125

Gly Gly Arg Pro Gly Gly Gln Asp Leu Gly Arg Asp Gly Tyr Ser Ser
                130                 135                 140

Gly Arg Pro Gly Gly Arg Pro Gly Gly Asn Gly Gln Asp Ser Gln Asp
145                 150                 155                 160

Gly Gln
```

<210> SEQ ID NO 43
<211> LENGTH: 162
<212> TYPE: PRT
<213> ORGANISM: Drosophila sechellia

<400> SEQUENCE: 43

```
Tyr Ser Ser Gly Arg Pro Gly Asn Gly Asn Gly Asn Gly Gly
1               5                   10                  15

Tyr Ser Ser Gly Arg Pro Gly Gly Gln Asp Leu Gly Pro Ser Gly Tyr
            20                  25                  30

Ser Gly Gly Arg Pro Gly Gly Gln Asp Leu Gly Ala Gly Gly Tyr Ser
        35                  40                  45

Asn Val Lys Pro Gly Gly Gln Asp Leu Gly Pro Gly Gly Tyr Ser Gly
    50                  55                  60

Gly Arg Pro Gly Gly Gln Asp Leu Gly Arg Asp Gly Tyr Ser Gly Gly
65                  70                  75                  80

Arg Pro Gly Gly Gln Asp Leu Gly Ala Gly Ala Tyr Ser Asn Gly Arg
            85                  90                  95

Pro Gly Gly Asn Gly Asn Gly Gly Ser Asp Gly Gly Arg Val Ile Ile
            100                 105                 110

Gly Gly Arg Val Ile Gly Gly Gln Asp Gly Gly Asp Gln Gly Tyr Ser
            115                 120                 125

Gly Gly Arg Pro Gly Gly Gln Asp Leu Gly Arg Asp Gly Tyr Ser Ser
        130                 135                 140

Gly Arg Pro Gly Gly Arg Pro Gly Gly Asn Gly Gln Asp Ser Gln Asp
145                 150                 155                 160

Gly Gln
```

```
<210> SEQ ID NO 44
<211> LENGTH: 162
<212> TYPE: PRT
<213> ORGANISM: Drosophila sechellia

<400> SEQUENCE: 44

Tyr Ser Ser Gly Arg Pro Gly Asn Gly Asn Gly Asn Gly Gly
1               5                   10                  15

Tyr Ser Ser Gly Arg Pro Gly Gly Gln Asp Leu Gly Pro Ser Gly Tyr
            20                  25                  30

Ser Gly Gly Arg Pro Gly Gly Gln Asp Leu Gly Ala Gly Gly Tyr Ser
        35                  40                  45

Asn Val Lys Pro Gly Gly Gln Asp Leu Gly Pro Gly Gly Tyr Ser Gly
    50                  55                  60

Gly Arg Pro Gly Gly Gln Asp Leu Gly Arg Asp Gly Tyr Ser Gly Gly
65                  70                  75                  80

Arg Pro Gly Gly Gln Asp Leu Gly Ala Gly Ala Tyr Ser Asn Gly Arg
            85                  90                  95

Pro Gly Gly Asn Gly Asn Gly Gly Ser Asp Gly Gly Arg Val Ile Ile
            100                 105                 110

Gly Gly Arg Val Ile Gly Gly Gln Asp Gly Gly Asp Gln Gly Tyr Ser
            115                 120                 125

Gly Gly Arg Pro Gly Gly Gln Asp Leu Gly Arg Asp Gly Tyr Ser Ser
        130                 135                 140

Gly Arg Pro Gly Gly Arg Pro Gly Gly Asn Gly Gln Asp Ser Gln Asp
145                 150                 155                 160

Gly Gln
```

```
<210> SEQ ID NO 45
<211> LENGTH: 25
<212> TYPE: PRT
<213> ORGANISM: Artificial Sequence
<220> FEATURE:
<223> OTHER INFORMATION: Description of Artificial Sequence: Synthetic
```

```
                        peptide

<400> SEQUENCE: 45

Gly Asp Tyr Lys Asp Asp Asp Asp Lys Asp Tyr Lys Asp Asp Asp
1               5                   10                  15

Lys Asp Tyr Lys Asp Asp Asp Asp Lys
                20                  25

<210> SEQ ID NO 46
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg
                85

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Glu Ala Glu Ala
1

<210> SEQ ID NO 48
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Gly
1

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
```

```
<220> FEATURE:
<221> NAME/KEY: MOD_RES
<222> LOCATION: (6)..(6)
<223> OTHER INFORMATION: Any amino acid

<400> SEQUENCE: 49

Ser Xaa Xaa Tyr Gly Xaa Pro
1               5

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Gly Gly Gly
1

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asn Gly Asn Gly
1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Gln Gly Gly
1

<210> SEQ ID NO 53
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Gln Gly Asn
1

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Gln Gly Gln
1
```

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Gln Gly Gln Gly
1               5

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Pro Gly Gly Gln
1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Pro Gly Gly Asn
1               5

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Gly Ser Phe
1

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Asn Gly Gly
1

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 60

Gly Gly Ala Gly Gly
1               5

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Any amino acid

<400> SEQUENCE: 61

Xaa Xaa Glu Pro Pro Val Ser Tyr Leu Pro Pro Ser
1               5                   10

<210> SEQ ID NO 62
<211> LENGTH: 4
<212> TYPE: PRT
<213> ORGANISM: Drosophila sechellia

<400> SEQUENCE: 62

Gly Arg Pro Glu
1

<210> SEQ ID NO 63
<211> LENGTH: 722
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Gly Arg Pro Glu Pro Pro Val
                85                  90                  95

Asn Ser Tyr Leu Pro Pro Ser Asp Ser Tyr Gly Ala Pro Gly Gln Ser
            100                 105                 110

Gly Ala Gly Gly Arg Pro Ser Asp Thr Tyr Gly Ala Pro Gly Gly Gly
        115                 120                 125

Asn Gly Gly Arg Pro Ser Asp Ser Tyr Gly Ala Pro Gly Gln Gly Gln
    130                 135                 140

Gly Gln Gly Gln Gly Gln Gly Tyr Gly Gly Lys Pro Ser Asp Ser
145                 150                 155                 160

Tyr Gly Ala Pro Gly Gly Asn Gly Asn Gly Arg Pro Ser Ser
                165                 170                 175

-continued

Ser Tyr Gly Ala Pro Gly Gly Gly Asn Gly Gly Arg Pro Ser Asp Thr
            180                 185                 190

Tyr Gly Ala Pro Gly Gly Gly Asn Gly Gly Arg Pro Ser Asp Thr Tyr
            195                 200                 205

Gly Ala Pro Gly Gly Gly Asn Gly Asn Gly Gly Arg Pro Ser Ser
    210                 215                 220

Ser Tyr Gly Ala Pro Gly Gln Gly Gln Gly Asn Gly Asn Gly Gly Arg
225                 230                 235                 240

Pro Ser Ser Ser Tyr Gly Ala Pro Gly Gly Asn Gly Gly Arg Pro
                245                 250                 255

Ser Asp Thr Tyr Gly Ala Pro Gly Gly Gly Asn Gly Gly Arg Pro Ser
        260                 265                 270

Asp Thr Tyr Gly Ala Pro Gly Gly Gly Asn Asn Gly Gly Arg Pro Ser
        275                 280                 285

Ser Ser Tyr Gly Ala Pro Gly Gly Gly Asn Gly Gly Arg Pro Ser Asp
        290                 295                 300

Thr Tyr Gly Ala Pro Gly Gly Gly Asn Gly Asn Gly Ser Gly Gly Arg
305                 310                 315                 320

Pro Ser Ser Ser Tyr Gly Ala Pro Ala Gln Gly Gln Gly Gly Phe Gly
                325                 330                 335

Gly Arg Pro Ser Asp Ser Tyr Gly Ala Pro Gly Gln Asn Gln Lys Pro
            340                 345                 350

Ser Asp Ser Tyr Gly Ala Pro Gly Ser Gly Asn Gly Ser Ala Gly Arg
        355                 360                 365

Pro Ser Ser Ser Tyr Gly Ala Pro Gly Ser Gly Pro Gly Gly Arg Pro
        370                 375                 380

Ser Asp Ser Tyr Gly Pro Pro Ala Ser Gly Ser Gly Ala Gly Ala
385                 390                 395                 400

Gly Gly Ser Gly Pro Gly Ala Asp Tyr Asp Asn Asp Glu Pro Ala
            405                 410                 415

Lys Tyr Glu Phe Asn Tyr Gln Val Glu Asp Ala Pro Ser Gly Leu Ser
            420                 425                 430

Phe Gly His Ser Glu Met Arg Asp Gly Asp Phe Thr Thr Gly Gln Tyr
        435                 440                 445

Asn Val Leu Leu Pro Asp Gly Arg Lys Gln Ile Val Glu Tyr Glu Ala
        450                 455                 460

Asp Gln Gln Gly Tyr Arg Pro Gln Ile Arg Tyr Glu Gly Asp Ala Asn
465                 470                 475                 480

Asp Gly Ser Gly Pro Ser Gly Pro Ser Gly Pro Gly Gly Pro Gly Gly
            485                 490                 495

Gln Asn Leu Gly Ala Asp Gly Tyr Ser Ser Gly Arg Pro Gly Asn Gly
            500                 505                 510

Asn Gly Asn Gly Asn Gly Gly Tyr Ser Ser Gly Arg Pro Gly Gly Gln
        515                 520                 525

Asp Leu Gly Pro Ser Gly Tyr Ser Gly Gly Arg Pro Gly Gly Gln Asp
        530                 535                 540

Leu Gly Ala Gly Gly Tyr Ser Asn Val Lys Pro Gly Gly Gln Asp Leu
545                 550                 555                 560

Gly Pro Gly Gly Tyr Ser Gly Gly Arg Pro Gly Gly Gln Asp Leu Gly
            565                 570                 575

Arg Asp Gly Tyr Ser Gly Gly Arg Pro Gly Gly Gln Asp Leu Gly Ala
        580                 585                 590

Gly Ala Tyr Ser Asn Gly Arg Pro Gly Gly Asn Gly Asn Gly Gly Ser

```
                     595                 600                 605
Asp Gly Gly Arg Val Ile Ile Gly Gly Arg Val Ile Gly Gly Gln Asp
            610                 615                 620
Gly Gly Asp Gln Gly Tyr Ser Gly Gly Arg Pro Gly Gly Gln Asp Leu
625                 630                 635                 640
Gly Arg Asp Gly Tyr Ser Ser Gly Arg Pro Gly Gly Arg Pro Gly Gly
                645                 650                 655
Asn Gly Gln Asp Ser Gln Asp Gly Gln Gly Tyr Ser Ser Gly Arg Pro
            660                 665                 670
Gly Gln Gly Gly Arg Asn Gly Phe Gly Pro Gly Gly Gln Asn Gly Asp
            675                 680                 685
Asn Asp Gly Ser Gly Tyr Arg Tyr Ser Gly Asp Tyr Lys Asp Asp Asp
            690                 695                 700
Asp Lys Asp Tyr Lys Asp Asp Asp Asp Lys Asp Tyr Lys Asp Asp Asp
705                 710                 715                 720
Asp Lys
```